United States Patent
Gerlach et al.

(10) Patent No.: US 12,115,157 B2
(45) Date of Patent: Oct. 15, 2024

(54) 3-PHENOXYAZETIDIN-1-YL-HETEROARYL PYRROLIDINE DERIVATIVES AND THE USE THEREOF AS MEDICAMENT

(71) Applicants: Boehringer Ingelheim International GmbH, Ingelheim Am Rhein (DE); Arena Pharmaceuticals, Inc., New York, NY (US)

(72) Inventors: Kai Gerlach, Mlttelbiberach (DE); Daniela Gavina Berta, Milan (IT); Marco Ferrara, San Donato Milanese (IT); Kirsten Gutsche, Laupheim (DE); Ursula Mueller-Vieira, Biberach an der Riß (DE); Scott Hobson, Mittelbiberach (DE); Frank Runge, Biberach an der Riß (DE); Graeme Semple, San Diego, CA (US); Viktor Vintonyak, Warthausen (DE); Yifeng Xiong, San Diego, CA (US)

(73) Assignees: Boehringer Ingelheim International GmbH, Ingelheim Am Rhein (DE); Arena Pharmaceuticals, Inc., San Diego, CA (US)

( * ) Notice: Subject to any disclaimer, the term of this patent is extended or adjusted under 35 U.S.C. 154(b) by 47 days.

(21) Appl. No.: 17/941,860

(22) Filed: Sep. 9, 2022

(65) Prior Publication Data
US 2023/0131465 A1    Apr. 27, 2023

Related U.S. Application Data

(60) Provisional application No. 63/243,776, filed on Sep. 14, 2021.

(51) Int. Cl.
| | |
|---|---|
| A61K 31/497 | (2006.01) |
| A61K 31/433 | (2006.01) |
| A61K 45/06 | (2006.01) |
| C07D 403/14 | (2006.01) |
| C07D 417/14 | (2006.01) |
| C07D 487/08 | (2006.01) |

(52) U.S. Cl.
CPC .......... *A61K 31/497* (2013.01); *A61K 31/433* (2013.01); *A61K 45/06* (2013.01); *C07D 403/14* (2013.01); *C07D 417/14* (2013.01); *C07D 487/08* (2013.01); *C07B 2200/05* (2013.01); *C07B 2200/09* (2013.01)

(58) Field of Classification Search
CPC ........................... A61K 31/497; A61K 31/433
See application file for complete search history.

(56) References Cited

U.S. PATENT DOCUMENTS

| | | | |
|---|---|---|---|
| 11,780,827 B2 | 10/2023 | Gerlach et al. | |
| 2022/0402917 A1* | 12/2022 | Wu | ........................ A61P 35/00 |

FOREIGN PATENT DOCUMENTS

| | | |
|---|---|---|
| EP | 2 253 618 A1 | 11/2010 |
| EP | 2 649 061 A1 | 10/2013 |
| WO | 2010/043052 A1 | 4/2010 |
| WO | 2016/176571 A1 | 11/2016 |
| WO | 2021/216705 A1 | 10/2021 |

OTHER PUBLICATIONS

International Search Report and Written Opinion, mailed May 19, 2021 for International Application No. PCT/EP2021/058099.
International Search Report and Written Opinion, mailed Jan. 24, 2023 for International Application No. PCT/EP2022/075107.

* cited by examiner

*Primary Examiner* — John S Kenyon
*Assistant Examiner* — Rehana Ismail
(74) *Attorney, Agent, or Firm* — Wolf, Greenfield & Sacks, P.C.

(57) ABSTRACT

The invention relates to 3-phenoxyazetidin-1-yl-heteroaryl pyrrolidine derivatives of general formula (I) which are agonists of GPR52, useful in treating central nervous system diseases and other diseases.
In addition, the invention relates to the 3-phenoxyazetidin-1-yl-heteroaryl pyrrolidine derivatives of general formula (I) for use as a medicament, pharmaceutical compositions comprising at least a compound of general formula (I) and processes for preparing pharmaceutical compositions as well as processes for manufacture the compounds according to the invention.

15 Claims, No Drawings

3-PHENOXYAZETIDIN-1-YL-HETEROARYL PYRROLIDINE DERIVATIVES AND THE USE THEREOF AS MEDICAMENT

CROSS REFERENCE TO RELATED APPLICATION

This application claims priority to U.S. Provisional Application Ser. No. 63/243,776, filed Sep. 14, 2021, the contents of which are incorporated herein by reference in its entirety.

FIELD OF THE INVENTION

The invention relates to 3-phenoxyazetidin-1-yl-heteroaryl pyrrolidine derivatives of general formula (I) which are agonists of GPR52, useful in treating central nervous system diseases and other diseases.

In addition, the invention relates to the 3-phenoxyazetidin-1-yl-heteroaryl pyrrolidine derivatives of general formula (I) for use as a medicament, pharmaceutical compositions comprising the 3-phenoxyazetidin-1-yl-heteroaryl pyrrolidine derivatives of general formula (I) and processes for preparing pharmaceutical compositions as well as processes for manufacture the compounds according to the invention.

BACKGROUND OF THE INVENTION

Human GPR52 is a G protein-coupled receptor (GPCR). The highest expression levels within the human central nervous system (CNS) are found in the striatum (WO2016/176571). Lower but significant expression levels are found in many other structures in the CNS, including the cortex. GPR52 co-localizes almost exclusively with the D2 receptor in the human and rodent striatum, and with the D1 receptor in the human and rodent cortex (WO2016/176571).

D1 receptors are generally Gs-coupled, and as such stimulate the production of the second messenger cAMP and the activity of PKA. In contrast, D2 receptors are generally Gi-coupled, and as such negatively regulate the production of cAMP and result in a decrease in PKA activity.

Since GPR52 co-localizes with the D1 receptor in the cortex and because both GPR52 and D1 receptors are Gs-coupled, a GPR52 agonist should functionally resemble a D1 agonist and therefore exhibit effects on cortical function and hypofrontality. Several compounds are known to function as D1 agonists in the cortex, where they increase cortical function and resolve hypofrontality.

The efficacy of existing antipsychotic agents is reportedly mediated by D2 antagonist activity on medium spiny neurons (MSNs) in the striatum. However, D2 antagonists produce side effects, such as motor symptoms and hyperprolactinemia. Since GPR52 co-localizes almost exclusively with the D2 receptor in the striatum and because GPR52 is Gs-coupled and D2 is Gi-coupled, a GPR52 agonist should functionally resemble a D2 antagonist and therefore exhibit antipsychotic efficacy. Further, because many of the side effects associated with D2 antagonists are mediated by the D2 receptor, GPR52 agonists could avoid the side effects associated with existing D2 antagonists.

Based on the expression pattern, co-localization, intracellular signaling, and functional properties, it is suggested that GPR52 is a significant modulator of brain function with relevance for the treatment of several neurological and psychiatric disorders, including those described below:

(1) Hypofrontality

Decreased blood flow in the prefrontal cortex (hypofrontality) is symptomatic of several neurological conditions, including the cognitive and negative symptoms associated with schizophrenia, attention deficit hyperactivity disorder (ADHD), bipolar disorder, major depressive disorder, and hypofrontality associated with substance abuse. Dopaminergic transmission in the prefrontal cortex is mainly mediated by D1 receptors, and D1 dysfunction has been linked to cognitive impairment and negative symptoms in schizophrenia (Goldman-Rakic P S, Castner S A, Svensson T H, Siever L I, Williams G V (2004) *Targeting the dopamine D1 receptor in schizophrenia: insights for cognitive dysfunction. Psychopharmacology* 174, 3-16). Increasing function in the prefrontal cortex with a GPR52 agonist is therefore useful for the treatment of symptoms associated with hypofrontality.

(2) Movement Disorders

The striatum is involved in the control of movement. Pathology of the striatum is associated with many movement disorders, including hyperkinetic movement disorders characterized by excessive abnormal involuntary movements (known as hyperkinesias). Examples of hyperkinetic movement disorders include tremors, dystonia, chorea, ballism, athetosis, tics/Tourette's syndrome, Huntington's disease, myoclonus and startle syndromes, stereotypies, and akathisia. In the striatum, GPR52 is almost exclusively expressed on neurons of the indirect striatal pathway. Hyperkinesias are associated with the dysfunction of inhibitory, D2-expressing neurons of this pathway. This dysfunction leads to the inability to inhibit movement, resulting in tics, chorea, vocalizations, tremors, and other hyperkinetic symptoms. For example, early hyperkinetic motor symptoms in Huntington's disease are the result of selective damage to the indirect, D2-containing pathway (Albin R L, Reiner A, Anderson K D, Penney J B, Young A B. (1990) *Striatal and nigral neuron subpopulations in rigid Huntington's disease: implications for the functional anatomy of chorea and rigidity-akinesia. Ann Neurol.* 27, 357-365). Further, D2 receptor binding in striatum is associated with the severity of Tourette syndrome symptoms (Wolf S S, Jones D W, Enable M B, Gorey J G, Lee K S, Hyde T M, Coppola R, Weinberger D R (1996) *Tourette syndrome: prediction of phenotypic variation in monozygotic twins by caudate nucleus D2 receptor binding. Science* 273, 1225-1227).

The stimulation of GPR52 with agonists activates the indirect striatal pathway, leading to more inhibitory control over movement and the resolution of hyperkinetic symptoms. The GPR52 agonists disclosed herein are therefore useful for the treatment of such symptoms.

(3) Psychotic Disorders

The psychotic symptoms of schizophrenia result from overactive presynaptic dopamine activity in the striatum (Howes O D, Kapur S (2009) *The dopamine hypothesis of schizophrenia: version III—the final common pathway. Schizophr Bull.* 35, 549-562). The clinical efficacy of existing antipsychotic drugs for treating psychotic symptoms is dependent on blockade of the D2 receptor. All known antipsychotic drugs with efficacy for the treatment of psychosis are either antagonists or partial agonists at the dopamine D2 receptor (Remington G, Kapur S (2010) *Antipsychotic dosing: how much but also how often? Schizophr Bull.* 36, 900-903). While these antipsychotic drugs can treat the positive (or psychotic) symptoms of schizophrenia, they do not treat other aspects of schizophrenia, such as the negative symptoms or cognitive impairment. Based on the co-expression of the GPR52 and the dopamine D2 receptor, GPR52 agonists should treat the psychotic symptoms associated with schizophrenia. Additionally, since the mechanism of action of GPR52 agonists is unique to known D2 receptor associated antipsychotic drugs, it would be anticipated that GPR52 agonists augment the anti-psychotic efficacy of known neuroleptics. This should result not only in improved anti-psychotic efficacy but could be used to lower the dose of anti-psychotic drugs, thereby lowering their associated side effects. Increased serum prolactin levels is one of the prominent side effect profiles of known D2R antagonist anti-psychotics, whereas GPR52 agonists have been demonstrated to lower serum prolactin levels, therefore, co-application of GPR52 agonists with D2R antagonist anti-psychotics may normalize serum prolactin levels, thereby lowering the side effects associated with the D2R antagonist anti-psychotic. In addition, GPR52 agonists should treat the psychotic symptoms associated with various psychiatric indications, including schizoaffective disorder, schizotypal disorder, schizophreniform disorder, treatment resistant schizophrenia, drug-induced psychotic disorder, bipolar disorder, autism-spectrum disorder, and attenuated psychosis syndrome. Furthermore, GPR52 agonists should treat the psychotic and neuropsychiatric symptoms associated with various neurodegenerative indications, including Parkinson's disease, Alzheimer's disease, frontotemporal dementia, vascular cognitive impairment, and dementia with Lewy Bodies. These antipsychotic drugs are also associated with significant side effect profiles, including weight gain, metabolic syndrome, diabetes, hyperlipidemia, hyperglycemia, insulin resistance, extrapyramidal symptoms, hyperprolactinemia, and tardive dyskinesia. Because GPR52 agonists should functionally resemble D2 antagonists, the GPR52 agonists disclosed herein are useful for the treatment of psychotic disorders.

(4) Other D1-Related Disorders

Several neurological and psychiatric drugs are known to function as D1 agonists, including A-86929, dinapsoline, doxanthrine, SKF-81297, SKF-82958, SKF-38393, fenoldopam, 6-Br-APB, and stepholoidine. Because GPR52 agonists should functionally resemble D1 agonists (and are co-localized), the GPR52 agonists disclosed herein are useful for the treatment of disorders treatable by D1 agonists, including but not limited to addiction (e.g., cocaine addiction), hypertension, restless leg syndrome, Parkinson's disease, and depression. Furthermore, based on its expression pattern and functional coupling, GPR52 agonists are useful for the treatment of the cognitive deficits associated with schizophrenia, schizophreniform disorder, treatment resistant schizophrenia attenuated psychosis syndrome and schizotypal disorder, bipolar disease, autism-spectrum disorder, Alzheimer's disease, Parkinson's disease, frontotemporal dementia (Pick's disease), Lewy-body dementia, vascular dementia, post-stroke dementia, and Creutzfeldt-Jakob disease.

(5) Other D2-Related Disorders

Several neurological disorders, such as obsessive-compulsive disorder and impulse control disorders are associated with alterations in dopamine receptor signaling, therefore GPR52 agonists are useful from the treatment of these indications (Lopez A M, Weintraub D, Claassen D O (2017) *Impulse control disorders and related complications of Parkinson's Disease Therapy. Semin Neurol.* 37, 186-192) (Koo M S, Kim E J, Roh D, Kim C H (2014) *Role of dopamine in the pathophysiology and treatment of obsessive-compulsive disorder. Exp. Rev. Neurotherap.* 10, 275-290). Additionally, several neurological and psychiatric drugs are known to function as D2 antagonists, including atypical antipsychotics (e.g., aripiprazole, clozapine, olanzapine, and ziprasidone), domperidone, eticlopride, fallypride, desmethoxyfallypride, L-741,626, raclopride, hydroxyzine, itopride, SV 293, typical antipsychotics, yohimibine, amisulpride, and UH-232. Because GPR52 agonists should functionally resemble D2 antagonists, the GPR52 agonists disclosed herein are useful for the treatment of disorders treatable by D2 antagonists, including but not limited to psychotic disorders, detachment, anxiety, anxiety/tension associated with psychoneurosis, acute mania, agitation, mania in bipolar disorder, dysthymia, nausea, vomiting, gastrointestinal conditions, dyspepsia, and addiction (e.g., cocaine addiction, amphetamine addiction, etc.).

Therefore, it is believed that GPR52 agonists are promising candidates for treating diseases of the central nervous system.

There is thus a need to develop compounds that would have an agonistic effect on GPR52 for preventing and/or treating mental disorders.

Particularly, there is a need to develop compounds that would have an agonistic effect on GPR52 and optimized drug properties that would be useful as pharmaceutical agents for preventing and/or treating mental disorders such as schizophrenia.

WO2009/157196, WO2009/107391, WO2011/078360, WO2011/093352, WO2011/145735, WO2012/020738, WO2016/176571 as well as WO2021/090030, WO2021/198149 and WO2021/216705 disclose GPR52 modulating compounds for treating diseases of the central nervous system and other diseases.

AIM OF THE INVENTION

It has now been found that compounds of the present invention according to general formula (I), or pharmaceutically acceptable salt thereof, are effective agonists of GPR52.

In addition to the agonistic property toward GPR52, the compounds of the present invention provide further advantageous properties as to be viable for human therapy, such as low plasma protein binding, high stability in human hepatocytes, a drug metabolism extended to a non-CYP enzyme metabolism such as a hydrolase-mediated pathway, low hERG channel inhibition (or interaction), and/or an adequate aqueous solubility for compounds that are to be used as drugs.

Compounds of the present invention according to general formula (I) are metabolically stable in human hepatocytes. Therefore, compounds of the present invention are expected to have a favorable in vivo clearance and thus the desired duration of action in humans. The primary site of metabolism for many drugs is the liver, thus, hepatocytes represent a model system for studying drug metabolism in vitro. Enhanced stability in human hepatocytes is associated with several pharmacokinetic advantages, including increased bioavailability and/or longer half-life which can enable lower and/or less frequent dosing of patients. A lower and/or less frequent efficacious dose of a compound for disease treatment minimize the potential side effects. Thus, enhanced metabolic stability in human hepatocytes is a favourable characteristic for compounds that are to be used as drugs.

Furthermore, compounds of the present invention according to general formula (I) show low plasma protein binding and as a consequence high fraction unbound in plasma, which translates into adequate low efficacious doses of the compounds for disease treatment and as a consequence in further potential advantages such as minimization of side effects. Consequently, compounds of the present invention are viable for human therapy, particularly compounds of general formula (I) having both a high to moderate metabolic stability and a low plasma protein binding.

The compounds of the present invention according to general formula (I), with the proviso that the group $R^6$ is a $C_{1-3}$-alkylcarbonyl moiety, show a non-CYP enzyme metabolism, particularly a hydrolase-mediated metabolism, which contributes to a diversified overall metabolism and leads to a reduced risk for pharmacokinetic drug-drug interactions via cytochrome P450 enzymes.

Drug-drug interactions refer to the influence of one drug upon another, typically occurring if a drug affects the function or expression of a metabolic enzyme or a transporter. The most serious pharmacokinetic interactions are those in which the second drug changes the clearance of the first one. An example is the inhibition of metabolism of one drug by a co-administered drug: there will be an increase in the plasma concentration of the first drug that could result in a clinically relevant increase of the therapeutic response or increased toxicity.

Drug metabolism primarily occurs in the liver and intestine. These organs express a wide variety of drug metabolizing enzymes and are responsible for the biotransformation of many drugs. Phase I oxidative metabolism occurs primarily through the cytochrome P450 (CYP) family of enzymes located in the hepatic endoplasmic reticulum but can also be mediated by non-CYP enzymes such as the hydrolase enzymes. These functionalizing reactions are often followed by conjugation reactions (Phase II) in order to increase the excretability of the xenobiotic.

Cytochrome P450 (CYP) enzymes are considered the major enzyme family capable of catalyzing oxidative biotransformation (phase 1 metabolism) of most drugs and other lipophilic xenobiotics, whereas drug metabolism mediated through non-CYP enzyme mediated pathways is less prominent. If CYP-independent pathways are involved in the oxidation, hydrolysis or conjugation of a drug, aldehyde oxidase, esterases/hydrolases, and uridine diphosphoglucuronosyl transferases (UGTs) are major enzymes catalyzing such metabolism, respectively. For example, the main enzymes responsible for amide hydrolysis, resulting in N-deacylation of the drug, are the serine hydrolases such as arylacetamide deacetylase.

Liver microsomes provide an excellent in vitro tool to identify such non-CYP metabolic pathways including elucidation of major metabolites.

In clinical psychiatry, combination pharmacotherapy is commonly used to treat patients with comorbid psychiatric or physical illnesses, to control the side effects of a specific drug or to augment a medication effect. However, said polypharmacy approaches involve a high risk for CYP-mediated drug-drug interactions. Therefore, the use of drugs with low potential for drug-drug interactions is desirable, especially for elderly patients who are more likely to take multiple medications concurrently (Spina E, de Leon, J. (2007) *Metabolic Drug Interactions with Newer Antipsychotics: A Comparative Review. Basic Clin. Pharmacol. Toxicol.* 100, 4-22).

Therefore, the additional contribution to overall metabolic clearance through non-CYP enzyme dependent pathways, e.g. via hydrolase-mediated metabolism, leading to a more diversified metabolism and a reduced risk for drug-drug interactions such as shown by the compounds of the present invention according to general formula (I) wherein group $R^6$ is a $C_{1-3}$-alkylcarbonyl moiety, is highly desirable. Consequently, compounds of the present invention are viable for human therapy.

Inhibition of the hERG channel and subsequent delayed cardiac repolarization is associated with an increased risk for a specific polymorphic ventricular tachyarrhythmia, torsade de pointes, as established by Sanguinetti et al. (1995, *Cell*, 81 (2): 299-307) and subsequent evidence. To minimize this risk, screening against hERG channel inhibition in an in vitro system using heterologous expression of the hERG channel is common practice and an important part of later preclinical profiling as recommended by the ICH guideline S 7 B (*International Conference on Harmonization* (2005): *ICH Topic S 7 B; The nonclinical Evaluation of the Potential for delayed Ventricular Repolarization (QT Interval Prolongation) by Human Pharmaceuticals*). Therefore, low to moderate hERG channel inhibition or interaction, such as shown by the compounds of the present invention, is highly desirable. Consequently, compounds of the present invention are viable for human therapy.

Compounds of the present invention according to formula (I) show an acceptable aqueous solubility for compounds that are to be used as drugs. Enhanced solubility of a compound leads to an improved drug product developability. Moreover, as is known in the art, poorly soluble compounds may suffer from poor human exposure.

Accordingly, one aspect of the invention refers to compounds according to general formula (I) or salts thereof, preferably pharmaceutically acceptable salts thereof, as agonists of GPR52.

Another aspect of the invention refers to compounds according to general formula (I) or salts thereof, preferably pharmaceutically acceptable salts thereof, as agonists of GPR52 with high to moderate human hepatocyte stability.

Another aspect of the invention refers to compounds according to general formula (I) or salts thereof, preferably pharmaceutically acceptable salts thereof, as agonists of GPR52 with low to moderate human plasma protein binding.

Another aspect of the invention refers to compounds according to general formula (I) wherein group $R^6$ is a $C_{1-3}$-alkylcarbonyl moiety or salts thereof, preferably pharmaceutically acceptable salts thereof, as agonists of GPR52 with a diversified metabolism including a non-CYP enzyme dependent metabolic pathway such as a hydrolase-mediated metabolism.

Another aspect of the invention refers to compounds according to general formula (I) or salts thereof, preferably pharmaceutically acceptable salts thereof, as agonists of GPR52 with low to moderate hERG channel inhibition.

Another aspect of the invention refers to compounds according to general formula (I) or salts thereof, preferably pharmaceutically acceptable salts thereof, as agonists of GPR52 with adequate aqueous solubility for compounds that are to be used as drugs.

Another aspect of the invention refers to compounds according to general formula (I) or salts thereof as agonists of GPR52 with high to moderate human hepatocyte stability and low to moderate human plasma protein binding.

Another aspect of the invention refers to compounds according to general formula (I) or salts thereof as agonists of GPR52 with high to moderate human hepatocyte stability, low to moderate human plasma protein binding, and a diversified metabolism including a non-CYP enzyme dependent metabolic pathway such as a hydrolase-mediated metabolism.

Another aspect of the invention refers to compounds according to general formula (I) or salts thereof as agonists of GPR52 with high to moderate human hepatocyte stability, low to moderate human plasma protein binding, a diversified metabolism including a non-CYP enzyme dependent metabolism such as a hydrolase-mediated metabolism (only for compounds wherein group $R^6$ is a $C_{1-3}$- alkylcarbonyl moiety), a low to moderate hERG channel inhibition and, optionally, an adequate aqueous solubility for compounds that are to be used as drugs.

In a further aspect this invention relates to pharmaceutical compositions containing at least one compound according to general formula (I), or pharmaceutically acceptable salts thereof, optionally together with one or more inert adjuvant, diluent and/or carrier.

A further aspect of the present invention relates to compounds according to general formula (I) or pharmaceutically acceptable salts thereof, or pharmaceutical compositions comprising compounds according to formula (I) or pharmaceutically acceptable salts thereof, for the use in the prevention and/or treatment of disorders related to insufficient GPR52 activity.

Another aspect of the invention relates to processes of manufacture of the compounds of the present invention according to general formula (I) or salts thereof, particularly pharmaceutically acceptable salts.

Other aims of the present invention will become apparent to the skilled man directly from the foregoing and following remarks.

DETAILED DESCRIPTION

In a first aspect the present invention relates to compounds of general formula (I)

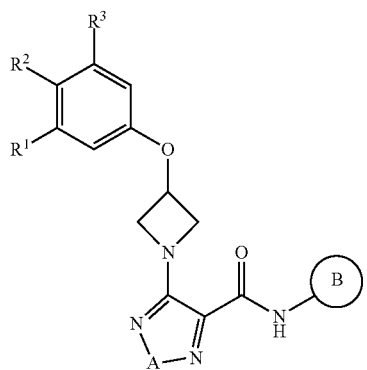

(I)

wherein
A is selected from the group $A^a$ consisting of
—CH=CH— and —S—;
B is selected from the group $B^a$ consisting of

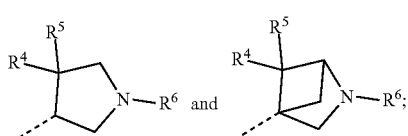

$R^1$ is selected from the group $R^{1a}$ consisting of
H— and F—;

$R^2$ is selected from the group $R^{2a}$ consisting of
H— and F—;
$R^3$ is selected from the group $R^{3a}$ consisting of
F—, Cl—, $F_2HCO$—, $F_3CO$—, $F_2HC$— and $F_3C$—;
$R^4$ is selected from the group $R^{4a}$ consisting of
H— and F—;
$R^5$ is selected from the group $R^{5a}$ consisting of
H— and F—;
$R^6$ is selected from the group $R^{6a}$ consisting of
H—, $C_{1-3}$-alkylcarbonyl- and $C_{1-3}$-alkylsulfonyl-,
wherein the $C_{1-3}$-alkylcarbonyl-group and $C_{1-3}$-alkylsulfonyl-group are optionally substituted with 1 to 5 (e.g. 2, 3 or 4) substituents independently selected from the group consisting of fluorine and deuterium;
or a salt thereof, preferably a pharmaceutically acceptable salt.

Unless otherwise stated, the groups, residues, and substituents, particularly A, B, $R^1$, $R^2$, $R^3$, $R^4$, $R^5$ and $R^6$ are defined as above and hereinafter. If residues, substituents, or groups occur several times in a compound they may have the same or different meanings. Some preferred meanings of groups and substituents of the compounds according to the invention will be given hereinafter.

In a further embodiment of the present invention
B is selected from the group $B^b$ consisting of

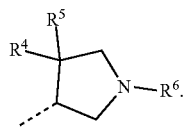

In a further embodiment of the present invention
B is selected from the group $B^c$ consisting of

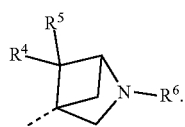

A further embodiment of the present invention relates to compounds of general formula (I.I)

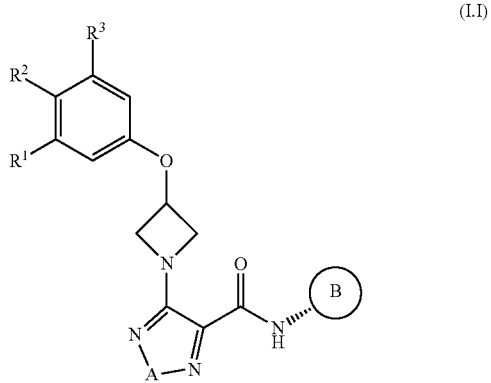

(I.I)

wherein
A, B, $R^1$, $R^2$, $R^3$, $R^4$, $R^5$ and $R^6$ are substituents as described in the present invention, and characterized in that the compound of general formula (I.I) is a single enantiomer or a couple of diastereoisomers or a single diastereoisomer according to the meaning of the groups B, $R^4$ and $R^5$.

The general formula (I.I) encompasses the general formula (I.I.B$^b$) and (I.I.B$^c$)

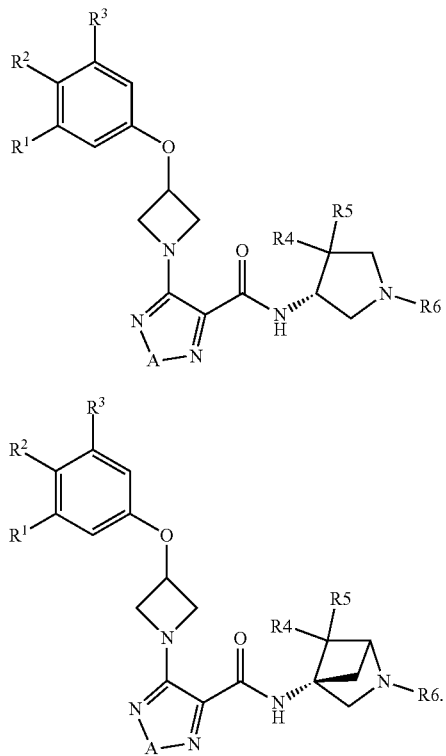

(I.I. B$^b$)

(I.I. B$^c$)

A further embodiment of the present invention relates to compounds of general formula (I.II)

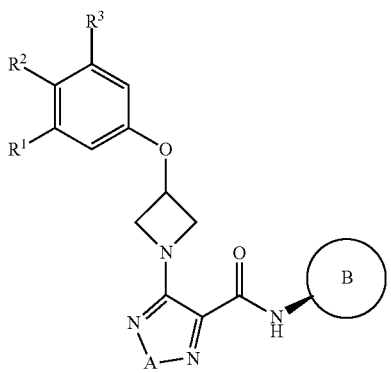

(I.II)

wherein

A, B, $R^1$, $R^2$, $R^3$, $R^4$, $R^5$ and $R^6$ are substituents as described in the present invention, and characterized in that the compound of general formula (I.II) is a single enantiomer or a couple of diastereoisomers or a single diastereoisomer according to the meaning of the groups B, $R^4$ and $R^5$.

The general formula (I.II) encompasses the general formula (I.II.B$^b$) and (I.II.B$^c$)

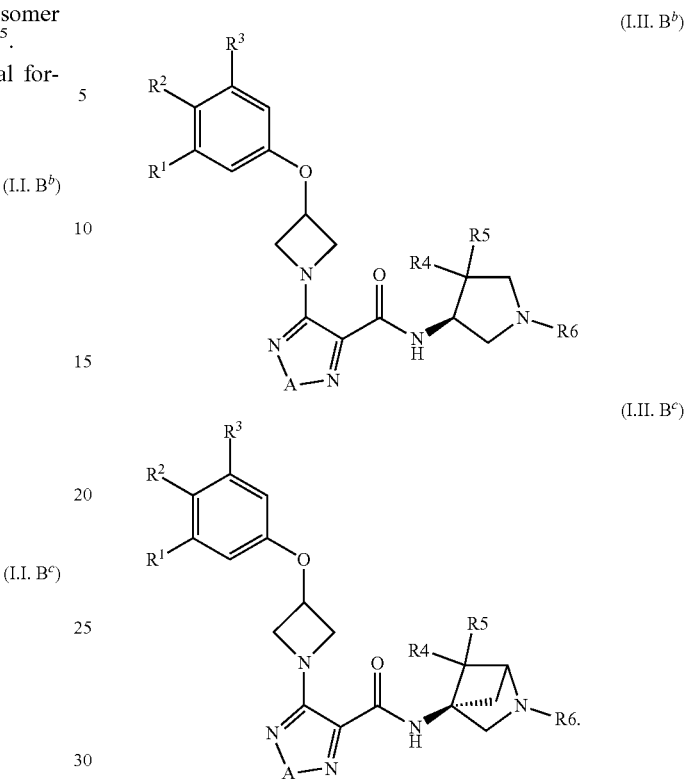

(I.II. B$^b$)

(I.II. B$^c$)

It will be understood from those skilled in the art that general formula (I.I) (e.g. general formula (I.I.B$^b$) or (I.I.B$^c$) encompasses a single enantiomer or a couple of diastereoisomers or a single diastereoisomer according to the meaning of the groups B, $R^4$ and $R^5$ and, when applicable, to the configuration of the chiral carbon atom bearing $R^4$ and $R^5$. The same applies to general formula (I.II) (e.g. general formula (I.II.B$^b$) or (I.II.B$^c$).

For example, general formula (I.I.B$^b$) encompasses one single enantiomer when $R^4$ and $R^5$ have the same meaning (e.g. $R^4$ and $R^5$ are both H— or $R^4$ and $R^5$ are both F—). The same applies to general formula (I.II.B$^b$).

For example, general formula (I.I.B$^b$) encompasses a couple of diastereoisomers when $R^4$ and $R^5$ have a different meaning (e.g. $R^4$ is H— and $R^5$ is F—). The same applies to general formula (I.II.B$^b$).

For example, general formula (I.I.B$^b$) encompasses a single diastereoisomer when $R^4$ and $R^5$ have a different meaning (e.g. $R^4$ is H— and $R^5$ is F—) and the chiral carbon atom bearing $R^4$ and $R^5$ has a defined configuration (i.e. (S) or (R)). The same applies to general formula (I.II.B$^b$).

A further embodiment of the present invention relates to compounds of general formula (I.I.B$^b$).

A further embodiment of the present invention relates to compounds of general formula (I.II.B$^b$).

In a further embodiment of the present invention

A is selected from the group $A^b$ consisting of —CH=CH—.

In a further embodiment of the present invention

A is selected from the group $A^c$ consisting of —S—.

In a further embodiment of the present invention $R^3$ is selected from the group $R^{3b}$ consisting of F—, Cl—, and $F_2$HC—.

In a further embodiment of the present invention R$^3$ is selected from the group R$^{3c}$ consisting of F—.

In a further embodiment of the present invention R$^6$ is selected from the group R$^{6b}$ consisting of C$_{1-3}$-alkylcarbonyl-,
  wherein the C$_{1-3}$-alkylcarbonyl-group is optionally substituted with 1 to 5 (e.g. 2, 3 or 4) deuterium.

In a further embodiment of the present invention R$^6$ is selected from the group R$^{6c}$ consisting of acetyl,
  wherein the acetyl-group is optionally substituted with 1, 2 or 3 deuterium.

Each A$^x$, B$^x$, R$^{1x}$, R$^{2x}$, R$^{3x}$, R$^{4x}$, R$^{5x}$ and R$^{6x}$ represents a characterized, individual embodiment for the corresponding substituent as described above. Thus given the above definitions, individual embodiments of the first aspect of the invention are fully characterized by the term (A$^x$, B$^x$, R$^{1x}$, R$^{2x}$, R$^{3x}$, R$^{4x}$, R$^{5x}$ and R$^{6x}$), wherein for each index 'x' an individual FIGURE is given that ranges from 'a' to the highest letter given above. All individual embodiments described by the term in parentheses with full permutation of the indices 'x', referring to the definitions above, shall be comprised by the present invention.

The following table 1 shows such embodiments E-1 to E-50 of the compound of general formula (I) or a salt thereof, preferably a pharmaceutically acceptable salt, that are considered preferred. Embodiments E-8, E-9, E-26, E-27, E-45, and E-46 in table 1 are more preferred embodiments. All the embodiments E-1 to E-50 in table 1 may have a configuration according to general formula (I.I) or general formula (I.II), for example according to general formula (I.I.B$^b$), (I.I.B$^c$), (I.II.B$^b$) or (I.II.B$^c$), preferably according to general formula (I.I).

TABLE 1

Embodiments E-1 to E-50 of the invention

| | A$^x$ | B$^x$ | R$^{1x}$ | R$^{2x}$ | R$^{3x}$ | R$^{4x}$ | R$^{5x}$ | R$^{6x}$ |
|---|---|---|---|---|---|---|---|---|
| E-1 | A$^a$ | B$^a$ | R$^{1a}$ | R$^{2a}$ | R$^{3a}$ | R$^{4a}$ | R$^{5a}$ | R$^{6a}$ |
| E-2 | A$^a$ | B$^a$ | R$^{1a}$ | R$^{2a}$ | R$^{3a}$ | R$^{4a}$ | R$^{5a}$ | R$^{6b}$ |
| E-3 | A$^a$ | B$^a$ | R$^{1a}$ | R$^{2a}$ | R$^{3a}$ | R$^{4a}$ | R$^{5a}$ | R$^{6c}$ |
| E-4 | A$^a$ | B$^a$ | R$^{1a}$ | R$^{2a}$ | R$^{3b}$ | R$^{4a}$ | R$^{5a}$ | R$^{6a}$ |
| E-5 | A$^a$ | B$^a$ | R$^{1a}$ | R$^{2a}$ | R$^{3b}$ | R$^{4a}$ | R$^{5a}$ | R$^{6b}$ |
| E-6 | A$^a$ | B$^a$ | R$^{1a}$ | R$^{2a}$ | R$^{3b}$ | R$^{4a}$ | R$^{5a}$ | R$^{6c}$ |
| E-7 | A$^a$ | B$^a$ | R$^{1a}$ | R$^{2a}$ | R$^{3c}$ | R$^{4a}$ | R$^{5a}$ | R$^{6a}$ |
| E-8 | A$^a$ | B$^a$ | R$^{1a}$ | R$^{2a}$ | R$^{3c}$ | R$^{4a}$ | R$^{5a}$ | R$^{6b}$ |
| E-9 | A$^a$ | B$^a$ | R$^{1a}$ | R$^{2a}$ | R$^{3c}$ | R$^{4a}$ | R$^{5a}$ | R$^{6c}$ |
| E-10 | A$^b$ | B$^a$ | R$^{1a}$ | R$^{2a}$ | R$^{3a}$ | R$^{4a}$ | R$^{5a}$ | R$^{6a}$ |
| E-11 | A$^b$ | B$^a$ | R$^{1a}$ | R$^{2a}$ | R$^{3a}$ | R$^{4a}$ | R$^{5a}$ | R$^{6b}$ |
| E-12 | A$^b$ | B$^a$ | R$^{1a}$ | R$^{2a}$ | R$^{3a}$ | R$^{4a}$ | R$^{5a}$ | R$^{6c}$ |
| E-13 | A$^b$ | B$^a$ | R$^{1a}$ | R$^{2a}$ | R$^{3b}$ | R$^{4a}$ | R$^{5a}$ | R$^{6a}$ |
| E-14 | A$^b$ | B$^a$ | R$^{1a}$ | R$^{2a}$ | R$^{3b}$ | R$^{4a}$ | R$^{5a}$ | R$^{6b}$ |
| E-15 | A$^b$ | B$^a$ | R$^{1a}$ | R$^{2a}$ | R$^{3b}$ | R$^{4a}$ | R$^{5a}$ | R$^{6c}$ |
| E-16 | A$^b$ | B$^a$ | R$^{1a}$ | R$^{2a}$ | R$^{3c}$ | R$^{4a}$ | R$^{5a}$ | R$^{6a}$ |
| E-17 | A$^b$ | B$^a$ | R$^{1a}$ | R$^{2a}$ | R$^{3c}$ | R$^{4a}$ | R$^{5a}$ | R$^{6b}$ |
| E-18 | A$^b$ | B$^a$ | R$^{1a}$ | R$^{2a}$ | R$^{3c}$ | R$^{4a}$ | R$^{5a}$ | R$^{6c}$ |
| E-19 | A$^b$ | B$^b$ | R$^{1a}$ | R$^{2a}$ | R$^{3a}$ | R$^{4a}$ | R$^{5a}$ | R$^{6a}$ |
| E-20 | A$^b$ | B$^b$ | R$^{1a}$ | R$^{2a}$ | R$^{3a}$ | R$^{4a}$ | R$^{5a}$ | R$^{6b}$ |
| E-21 | A$^b$ | B$^b$ | R$^{1a}$ | R$^{2a}$ | R$^{3a}$ | R$^{4a}$ | R$^{5a}$ | R$^{6c}$ |
| E-22 | A$^b$ | B$^b$ | R$^{1a}$ | R$^{2a}$ | R$^{3b}$ | R$^{4a}$ | R$^{5a}$ | R$^{6a}$ |
| E-23 | A$^b$ | B$^b$ | R$^{1a}$ | R$^{2a}$ | R$^{3b}$ | R$^{4a}$ | R$^{5a}$ | R$^{6b}$ |
| E-24 | A$^b$ | B$^b$ | R$^{1a}$ | R$^{2a}$ | R$^{3b}$ | R$^{4a}$ | R$^{5a}$ | R$^{6c}$ |
| E-25 | A$^b$ | B$^b$ | R$^{1a}$ | R$^{2a}$ | R$^{3c}$ | R$^{4a}$ | R$^{5a}$ | R$^{6a}$ |
| E-26 | A$^b$ | B$^b$ | R$^{1a}$ | R$^{2a}$ | R$^{3c}$ | R$^{4a}$ | R$^{5a}$ | R$^{6b}$ |
| E-27 | A$^b$ | B$^b$ | R$^{1a}$ | R$^{2a}$ | R$^{3c}$ | R$^{4a}$ | R$^{5a}$ | R$^{6c}$ |
| E-28 | A$^b$ | B$^c$ | R$^{1a}$ | R$^{2a}$ | R$^{3a}$ | R$^{4a}$ | R$^{5a}$ | R$^{6b}$ |
| E-29 | A$^b$ | B$^c$ | R$^{1a}$ | R$^{2a}$ | R$^{3b}$ | R$^{4a}$ | R$^{5a}$ | R$^{6b}$ |
| E-30 | A$^b$ | B$^c$ | R$^{1a}$ | R$^{2a}$ | R$^{3c}$ | R$^{4a}$ | R$^{5a}$ | R$^{6b}$ |
| E-31 | A$^b$ | B$^c$ | R$^{1a}$ | R$^{2a}$ | R$^{3c}$ | R$^{4a}$ | R$^{5a}$ | R$^{6c}$ |
| E-32 | A$^c$ | B$^a$ | R$^{1a}$ | R$^{2a}$ | R$^{3a}$ | R$^{4a}$ | R$^{5a}$ | R$^{6a}$ |
| E-33 | A$^c$ | B$^a$ | R$^{1a}$ | R$^{2a}$ | R$^{3a}$ | R$^{4a}$ | R$^{5a}$ | R$^{6b}$ |
| E-34 | A$^c$ | B$^a$ | R$^{1a}$ | R$^{2a}$ | R$^{3a}$ | R$^{4a}$ | R$^{5a}$ | R$^{6c}$ |
| E-35 | A$^c$ | B$^a$ | R$^{1a}$ | R$^{2a}$ | R$^{3b}$ | R$^{4a}$ | R$^{5a}$ | R$^{6a}$ |
| E-36 | A$^c$ | B$^a$ | R$^{1a}$ | R$^{2a}$ | R$^{3b}$ | R$^{4a}$ | R$^{5a}$ | R$^{6b}$ |
| E-37 | A$^c$ | B$^a$ | R$^{1a}$ | R$^{2a}$ | R$^{3b}$ | R$^{4a}$ | R$^{5a}$ | R$^{6c}$ |
| E-38 | A$^c$ | B$^a$ | R$^{1a}$ | R$^{2a}$ | R$^{3c}$ | R$^{4a}$ | R$^{5a}$ | R$^{6a}$ |
| E-39 | A$^c$ | B$^a$ | R$^{1a}$ | R$^{2a}$ | R$^{3c}$ | R$^{4a}$ | R$^{5a}$ | R$^{6b}$ |
| E-40 | A$^c$ | B$^a$ | R$^{1a}$ | R$^{2a}$ | R$^{3c}$ | R$^{4a}$ | R$^{5a}$ | R$^{6c}$ |
| E-41 | A$^c$ | B$^b$ | R$^{1a}$ | R$^{2a}$ | R$^{3a}$ | R$^{4a}$ | R$^{5a}$ | R$^{6b}$ |
| E-42 | A$^c$ | B$^b$ | R$^{1a}$ | R$^{2a}$ | R$^{3a}$ | R$^{4a}$ | R$^{5a}$ | R$^{6c}$ |
| E-43 | A$^c$ | B$^b$ | R$^{1a}$ | R$^{2a}$ | R$^{3b}$ | R$^{4a}$ | R$^{5a}$ | R$^{6b}$ |
| E-44 | A$^c$ | B$^b$ | R$^{1a}$ | R$^{2a}$ | R$^{3b}$ | R$^{4a}$ | R$^{5a}$ | R$^{6c}$ |
| E-45 | A$^c$ | B$^b$ | R$^{1a}$ | R$^{2a}$ | R$^{3c}$ | R$^{4a}$ | R$^{5a}$ | R$^{6b}$ |
| E-46 | A$^c$ | B$^b$ | R$^{1a}$ | R$^{2a}$ | R$^{3c}$ | R$^{4a}$ | R$^{5a}$ | R$^{6c}$ |
| E-47 | A$^c$ | B$^c$ | R$^{1a}$ | R$^{2a}$ | R$^{3a}$ | R$^{4a}$ | R$^{5a}$ | R$^{6b}$ |
| E-48 | A$^c$ | B$^c$ | R$^{1a}$ | R$^{2a}$ | R$^{3b}$ | R$^{4a}$ | R$^{5a}$ | R$^{6b}$ |
| E-49 | A$^c$ | B$^c$ | R$^{1a}$ | R$^{2a}$ | R$^{3c}$ | R$^{4a}$ | R$^{5a}$ | R$^{6b}$ |
| E-50 | A$^c$ | B$^c$ | R$^{1a}$ | R$^{2a}$ | R$^{3c}$ | R$^{4a}$ | R$^{5a}$ | R$^{6c}$ |

Accordingly, for example E-2 covers compounds of general formula (I),
wherein
A is selected from the group A$^a$ consisting of —CH=CH— and —S—;
B is selected from the group B$^a$ consisting of

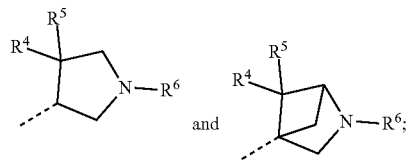

and

R$^1$ is selected from the group R$^{1a}$ consisting of H— and F—;
R$^2$ is selected from the group R$^{2a}$ consisting of H— and F—;
R$^3$ is selected from the group R$^{3a}$ consisting of F—, Cl—, F$_2$HCO—, F$_3$CO—, F$_2$HC— and F$_3$C—;
R$^4$ is selected from the group R$^{4a}$ consisting of H— and F—;
R$^5$ is selected from the group R$^{5a}$ consisting of H— and F—;
R$^6$ is selected from the group R$^{6b}$ consisting of C$_{1-3}$-alkylcarbonyl-,
  wherein the C$_{1-3}$-alkylcarbonyl-group is optionally substituted with 1 to 5 deuterium;
or a salt thereof, preferably a pharmaceutically acceptable salt.

Accordingly, for example E-26 covers compounds of general formula (I),
wherein
A is selected from the group A$^b$ consisting of —CH=CH—;
B is selected from the group B$^b$ consisting of

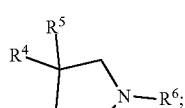

R$^1$ is selected from the group R$^{1a}$ consisting of H— and F—;

$R^2$ is selected from the group $R^{2a}$ consisting of H— and F—;
$R^3$ is selected from the group $R^{3c}$ consisting of F—;
$R^4$ is selected from the group $R^{4a}$ consisting of H— and F—;
$R^5$ is selected from the group $R^{5a}$ consisting of H— and F—;
$R^6$ is selected from the group $R^{6b}$ consisting of $C_{1-3}$-alkylcarbonyl-,
  wherein the $C_{1-3}$-alkylcarbonyl-group is optionally substituted with 1 to 5 deuterium;
or a salt thereof, preferably a pharmaceutically acceptable salt.

Accordingly, for example E-45 covers compounds of general formula (I), wherein
A is selected from the group $A^c$ consisting of —S—;
B is selected from the group $B^b$ consisting of

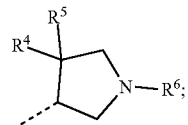

$R^1$ is selected from the group $R^{1a}$ consisting of H— and F—;
$R^2$ is selected from the group $R^{2a}$ consisting of H— and F—;
$R^3$ is selected from the group $R^{3c}$ consisting of F—;
$R^4$ is selected from the group $R^{4a}$ consisting of H— and F—;
$R^5$ is selected from the group $R^{5a}$ consisting of H— and F—;
$R^6$ is selected from the group $R^{6b}$ consisting of $C_{1-3}$-alkylcarbonyl-,
  wherein the $C_{1-3}$-alkylcarbonyl-group is optionally substituted with 1 to 5 deuterium;
or a salt thereof, preferably a pharmaceutically acceptable salt.

Further preferred are the following compounds listed in table 2 or salt thereof or stereoisomers thereof (the No. refers to the No. assigned to the compound in the experimental section). Each compound of table 2 is represented without indicating the stereochemistry thereof, if any. Specific information concerning stereochemical properties of compounds of table 2 can be taken from the experimental section. In case the final compounds according of said experimental section are salt forms, they can be converted into the neutral compound by conventional methods.

TABLE 2-continued

| No. | Structure |
|-----|-----------|
| 6 | (structure) |
| 7 | (structure) |
| 8 | (structure) |
| 9 | (structure) |
| 10 | (structure) |
| 11 | (structure) |
| 12 | (structure) |
| 13 | (structure) |

TABLE 2-continued

| No. | Structure |
|---|---|
| 14 | (structure) |
| 15 | (structure) |
| 16 | (structure) |
| H-1 | (structure) |
| H-2 | (structure) |
| H-3 | (structure) |
| H-4 | (structure) |

A further embodiment of the present invention covers the compounds of general formula (I), particularly the compounds listed in table 2, in form of their pharmaceutically acceptable salts.

A further embodiment of the present invention refers to pharmaceutical compositions comprising at least one compound according to formula (I), or pharmaceutically acceptable salts thereof, optionally together with at least one inert adjuvant, diluent and/or carrier.

In a further embodiment, the present invention relates to a compound of the present invention or a pharmaceutically acceptable salt thereof, or a pharmaceutical composition comprising at least one compound according to general formula (I) or pharmaceutically acceptable salts thereof, for use as a medicament.

In a further embodiment, the present invention relates to compounds according to general formula (I) or pharmaceutically acceptable salts thereof, or pharmaceutical compositions comprising compounds according to general formula (I) or pharmaceutically acceptable salts thereof, for use in the prevention and/or treatment of diseases or conditions which can be influenced by activation of GPR52.

Used Terms and Definitions

Some terms used above and hereinafter to describe the compounds according to the invention will now be defined more closely.

Terms not specifically defined herein should be given the meanings that would be given to them by one skilled in the art in light of the disclosure and the context. As used in the specification, however, unless specified to the contrary, the following terms have the meaning indicated and the following conventions are adhered to.

The term "$C_{1-3}$-alkyl", either alone or in combination with another radical, denotes an acyclic, cyclic, saturated, branched or linear hydrocarbon radical with 1, 2 or 3 C atoms. For example, the term $C_{1-3}$-alkyl embraces the radicals $H_3C-$, $H_3C-CH_2-$, $H_3C-CH_2-CH_2-$, $H_3C-CH(CH_3)-$, $(CH_2)_2-CH-$.

In general, for groups comprising two or more subgroups, the last named subgroup is the radical attachment point, for example, the substituent "$C_{1-3}$-alkyl-carbonyl-" means an $C_{1-3}$-alkyl group which is bound to a carbonyl-group, the latter of which is bound to the core molecule or to the group to which the substituent is attached. The same apply to the substituent "$C_{1-3}$-alkyl-sulfonyl-". For example, the "$C_{1-3}$-alkylcarbonyl-" group is selected from the group consisting of acetyl (i.e. $CH_3C(O)-$), ethanecarbonyl (i.e. $CH_3CH_2C(O)-$), propanecarbonyl (i.e. $CH_3(CH_2)_2C(O)-$), isopropanecarbonyl (i.e. $CH_3CH(CH_3)C(O)-$), and cyclopropanecarbonyl (i.e. $(CH_2)_2CHC(O)-$), For example, the "$C_{1-3}$-alkylsulfonyl-group" is selected from the group consisting of methanesulfonyl (i.e. $CH_3S(O)_2-$), ethanesulfonyl (i.e. $CH_3CH_2S(O)_2-$), propanesulfonyl (i.e. $CH_3(CH_2)_2S(O)_2-$), isopropanesulfonyl (i.e. $CH_3CH(CH_3)S(O)_2-$), and cyclopropanesulfonyl (i.e. $(CH_2)_2CHS(O)_2-$).

The term "substituted" as used herein means that any one or more hydrogens on the designated atom/group is replaced with a selection from the indicated group, provided that the designated atom's viable valence number is not exceeded, and that the substitution results in a stable compound. Moreover, the term "substituted with 1 to 5 substituents" as used herein means that 1, 2, 3, 4 or 5 substituents can be present on the designed atom/group.

Many of the terms given above may be used repeatedly in the definition of a formula or group and in each case have one of the meanings given above, independently of one another.

In case a compound of the present invention is depicted in form of a chemical name and as a formula in case of any discrepancy the formula shall prevail.

A dotted line is used in sub-formulas to indicate the bond or attachment point, which is connected to the core molecule, rest of the molecule or to the substituent to which it is bound as defined.

Unless specifically indicated, throughout the specification and the appended claims, a given chemical formula (e.g. all the compounds of table 2) or name shall encompass rotamers, tautomers and all stereo, optical and geometrical isomers (e.g. diastereomers, enantiomers, E/Z, trans/cis isomers etc., according to general formula (I.I) or (I.II)) and racemates thereof as well as mixtures in different proportions of the separate enantiomers, mixtures of diastereomers, or mixtures of any of the foregoing forms where such isomers exist, as well as solvates thereof such as for instance hydrates. For example, it will be understood from those skilled in the art that compound No. 1 of table 2 encompasses two enantiomers, as mixture (e.g. racemic mixture) or as a single enantiomer (e.g. (S) or (R)).

Moreover, it will be understood from those skilled in the art that compound No. 3 (or No. 14 or No. H-2) of table 2 encompasses two cis-stereoisomers and two trans-stereoisomers, as a mixture of two or four stereoisomers (e.g. a cis-racemic mixture and/or a trans-racemic mixture) or as a single stereoisomer.

Unless specifically indicated, also "pharmaceutically acceptable salts" as defined in more detail below shall encompass solvates thereof such as for instance hydrates.

As used herein, "pharmaceutically acceptable salt" refers to derivatives of the disclosed compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid. Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above, which for example are useful for purifying or isolating the compounds of the present invention (e.g. trifluoro acetate salts), also comprise a part of the invention.

The phrase "pharmaceutically acceptable adjuvant, diluent and/or carrier" is employed herein to refer to those materials which are, within the scope of sound medical judgment, suitable for use in contact with the tissues of human beings without excessive toxicity, irritation, allergic response, or other problem or complication, and commensurate with a reasonable benefit/risk ratio.

Preparation

The compounds according to the invention may be obtained using methods of synthesis known in principle. Preferably, the compounds are obtained by the following methods according to the invention which are described in more detail hereinafter.

The following Schemes illustrate generally how to manufacture the compounds of the present invention by way of example. The abbreviated substituents may be as defined above if not defined otherwise within the context of the schemes.

The invention also provides a process for making compounds of formula (I). Unless specified otherwise, A, B, $R^1$, $R^2$, $R^3$, $R^4$, $R^5$ and $R^6$ in the formulas below shall have the meaning as defined for formula (I) in the detailed description of the invention above.

Optimum reaction conditions and reaction times may vary depending on reactants used. Unless otherwise specified, solvents, temperatures, pressures, and other reaction conditions may be readily selected by one of ordinary skill in the art. Specific procedures are provided in the Experimental section. Typically, reaction progress may be monitored by thin layer chromatography (TLC), liquid chromatography-mass spectrometry (LC-MS) if desired, and intermediates and products may be purified by chromatography and/or by recrystallization.

The examples which follow are illustrative and, as recognized by one skilled in the art, particular reagents or conditions could be modified as needed for individual compounds without undue experimentation. Starting materials and intermediates used, in the methods below, are either commercially available or easily prepared from commercially available materials by those skilled in the art.

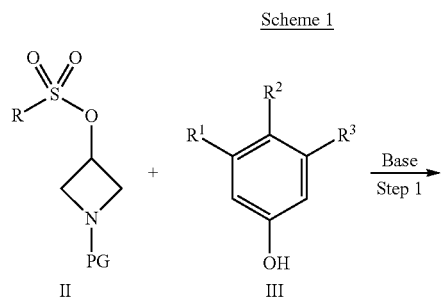

Scheme 1

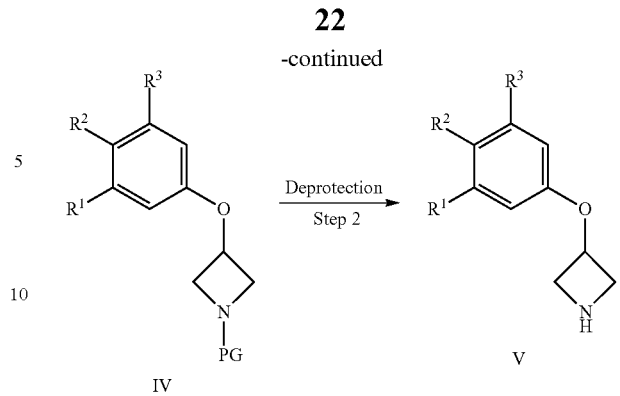

Scheme 1 illustrates the synthesis of amines (V) as intermediates for the synthesis of compounds (I). In a first step, a suitably protected (PG is protecting group e.g., $CO_2tBu$ (BOC), $CO_2Bn$) and suitably activated (sulfonylester, substituent R, e.g., methyl, $CF_3$ or tolyl) azetidine (II) is reacted with a phenol (III) using an appropriate solvent like dimethyl acetamide, dimethyl formamide, N-methyl-pyrrolidinone, acetonitrile, DMSO, dichloromethane, toluene or the like and an appropriate base like cesium carbonate, potassium carbonate, potassium tert-butoxide, sodium hydroxide, N-ethyl-diisopropylamine, pyridine or the like to form 3-phenoxyazetidines (IV). These intermediates are deprotected in a second step to give amines (V). Deprotection may be achieved by using a mineral acid like hydrochloric acid on BOC-protected intermediates (IV) or by catalytic hydrogenation using a catalyst like palladium on charcoal under an atmosphere of hydrogen on benzyloxy-carbonyl-protected intermediates (IV). Additional deprotection reactions are described in 'Protective Groups in Organic Synthesis', 3' edition, T. W. Greene and P. G. M. Wuts, Wiley-Interscience (1999). Depending on reaction conditions and work-up amines (V) may be obtained as salts.

Scheme 2

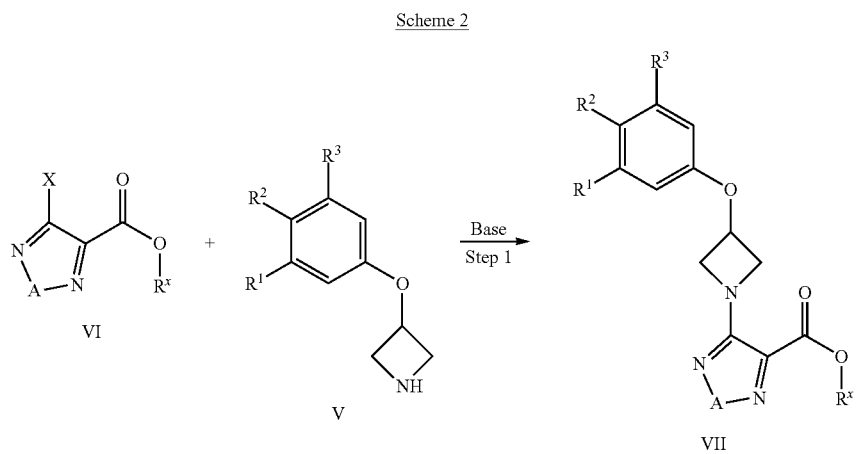

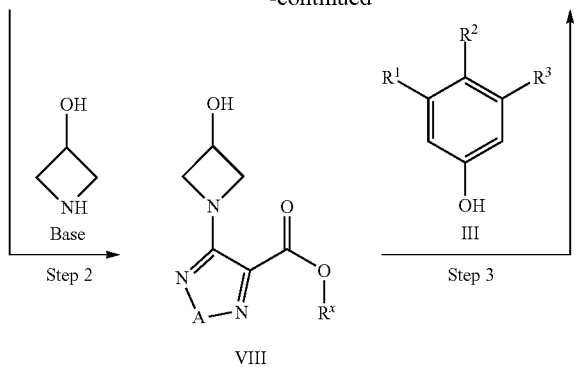

VIII

As shown in scheme 2, reacting the amine of formula (V) with a halo ester (VI) (X=halide, $R^X$=alkyl) in a nucleophilic aromatic substitution reaction (step 1), in a suitable solvent such as dioxane, THF, DMA or DMF and in the presence of a suitable base such as potassium tert-butoxide or NaH, provides ester compounds of formula (VII). Additionally, Buchwald-Hartwig-type cross coupling conditions may be used to form compounds (VII). For example, compounds (IV) (X=Cl, Br, I; $R^X$=alkyl) may be reacted with amines (V) in a suitable solvent such as toluene in the presence of a suitable catalyst such as palladium(II) acetate and a suitable ligand such as butyl-di-1-adamantyl-phosphine and a suitable base such as cesium carbonate to provide compounds of the general formula (VII).

Alternatively, halo ester (VI) may be reacted with hydroxy azetidine in a nucleophilic aromatic substitution reaction, in a suitable solvent such as DMA or the like and in the presence of a suitable base such as triethylamine, to give alcohols of the general formula (VIII). In a subsequent step, alcohols (VIII) may be converted into a phenyl ether compound of formula (VII) using the "Mitsunobu" method (see for examples *Tet. Lett.* 1994, 35, 2819 or *Synlett* 2005, 18, 2808): trialkyl or triaryl phosphine (such as tributyl phosphine or triphenyl phosphine) or solid-supported analogues such as polymer-bound triphenyl phosphine and a suitable dialkyl azadicarboxylate (e.g. DIAD, DEAD) are added to a compound of general formula (VIII) in the presence of an appropriate phenol (III) in a suitable solvent (e.g. THF or toluene) to generate aryl ether of the general formula (VII).

Scheme 3

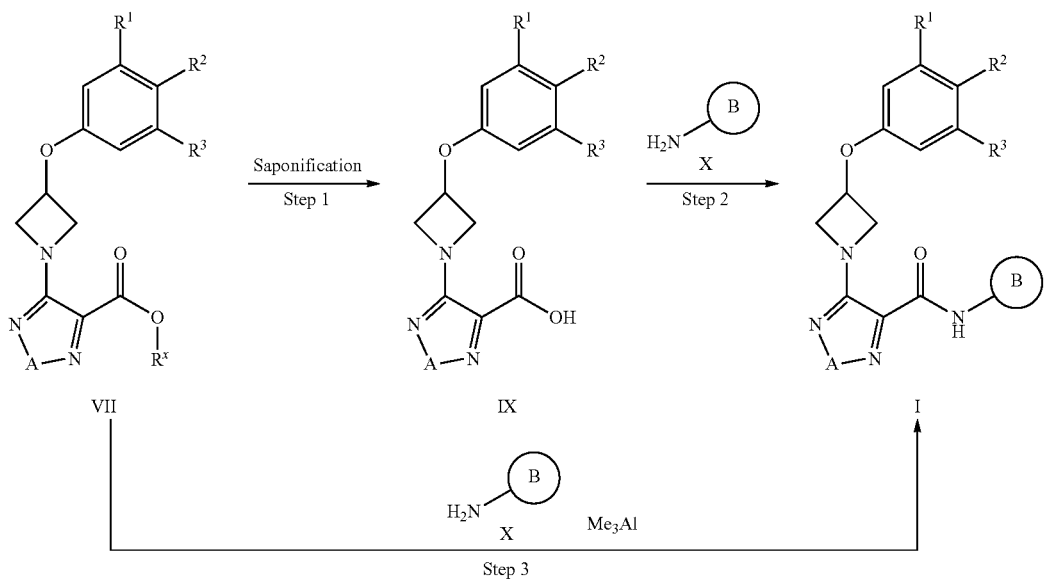

The preparation of compounds of general formula (I) is illustrated in scheme 3. In a first step carboxylic acid esters (VII) can be hydrolyzed with the appropriate hydroxide base (e.g., lithium hydroxide, sodium hydroxide, potassium hydroxide, barium hydroxide or the like) in solvent/water mixtures such as acetone/water, 1,4-dioxane/water, THF/water to form the corresponding carboxylic acids (IX) upon acidification.

Peptide coupling reactions known to the person skilled in the art (see for example M. Bodanszky, 1984, The Practice of Peptide Synthesis, Springer-Verlag) can be applied to react an amine of formula (X) with a carboxylic acid (IX) to yield a compound of general formula (I). For example, an amine (x) and a carboxylic acid (IX) in a suitable solvent such as acetonitrile, NMP, DMA or DMF in the presence of a suitable base such as DIPEA or 1-methyl-imidazole yields upon treatment with the coupling agent 2-chloro-4,5-di-hydro-1,3-dimethyl-1H-imidazolium hexafluorophosphate (CIP), Mukaiyama's reagent, chloro-N,N,N',N'-tetramethyl-formamidinium hexafluorophosphate (TCFH) or 1-[bis(di-methylamino)methylene]-1H-1,2,3-triazolo[4,5-b]pyri-dinium 3-oxid hexafluorophosphate (HATU) form a compound of formula (I).

Alternatively, a carboxylic acid (IX) in a suitable solvent such as DCM, DMF or toluene upon treatment with 1-chloro-N,N-2-trimethylpropenylamine, thionyl chloride or oxalyl chloride yields an intermediate acid chloride, which is then treated with an amine of formula (X), in a suitable solvent such as DCM, THF or DMF, in the presence of a suitable base such as TEA, to provide a compound of formula (I).

Alternatively, amines (X), pre-activated with trimethyl aluminium, can be reacted directly with carboxylic acid esters (VII) in suitable solvent such as DCM, dichloroeth-ane, THF or toluene to yield amides of general formula (I).

upon treatment with the coupling agent 2-chloro-4,5-di-hydro-1,3-dimethyl-1H-imidazolium hexafluorophosphate (CIP), Mukaiyama's reagent, chloro-N,N,N',N'-tetramethyl-formamidinium hexafluorophosphate (TCFH) or 1-[bis(di-methylamino)methylene]-1H-1,2,3-triazolo[4,5-b]pyri-dinium 3-oxid hexafluorophosphate (HATU) form a halo amide of general formula (XII) (X=halide). Alternatively, a carboxylic acid (XI) (X=halide, Y=OH) in a suitable solvent such as DCM, DMF or toluene upon treatment with 1-chloro-N,N-2-trimethylpropenylamine, thionyl chloride or oxalyl chloride yields an intermediate acid chloride (XI) (Y=Cl), which is then treated with an amine of formula (X), in a suitable solvent such as DCM, THF or DMF, in the presence of a suitable base such as TEA, to provide a halo amide of general formula (XII) (X=halide). Alternatively, amines (X), pre-activated with trimethyl aluminium, can be reacted directly with carboxylic acid esters (XI) (X=halide, Y=alkyloxy) in suitable solvent such as DCM, dichloroeth-ane, THF or toluene to yield halo amides of general formula (XII) (X=halide).

In a second step an amine of formula (V) is reacted with a halo amide (XII) (X=halide) in a nucleophilic aromatic Scheme 4

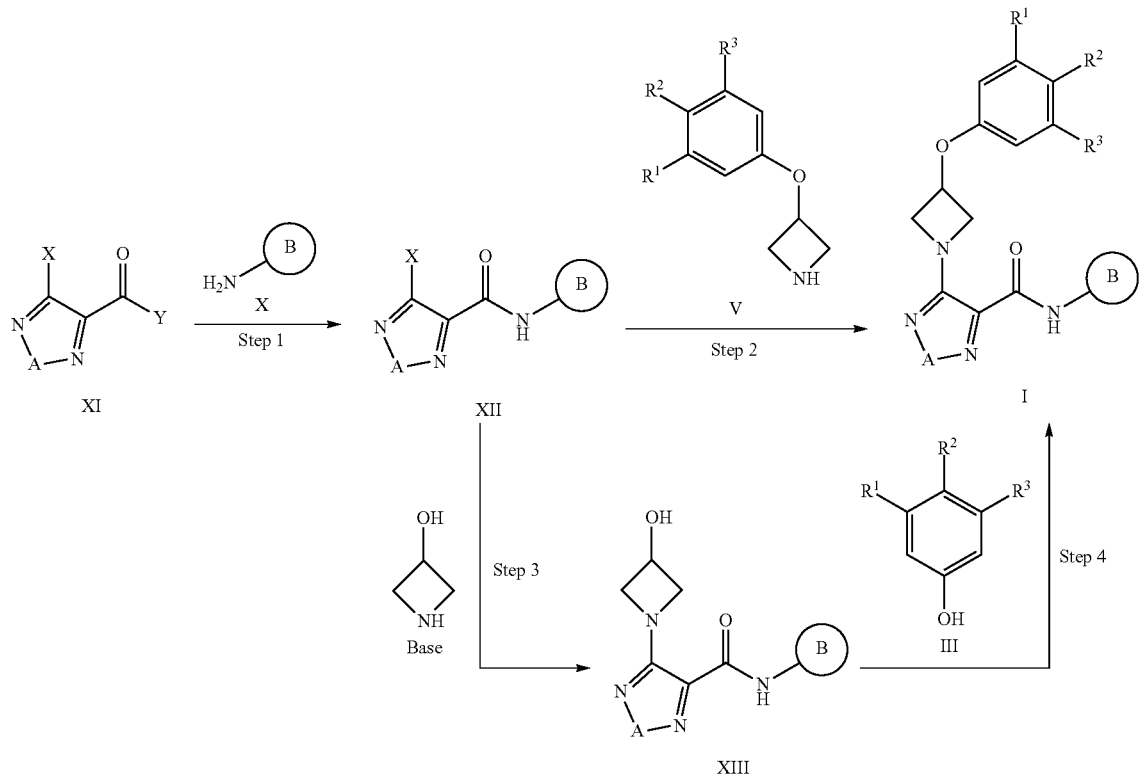

Alternatively, a compound of the general formula (I) can be synthesized as illustrated in scheme 4: peptide coupling reactions known to the person skilled in the art (see for example M. Bodanszky, 1984, The Practice of Peptide Synthesis, Springer-Verlag) can be applied in a first step to react an amine of formula (X) with a carboxylic acid (XI) (X=halide, Y=OH) to yield a halo amide of general formula (XII) (X=halide). For example, an amine (X) and a carbox-ylic acid (XI) (X=halide, Y=OH) in a suitable solvent such as acetonitrile, NMP, DMA or DMF in the presence of a suitable base such as DIPEA or 1-methyl-imidazole yields substitution reaction, in a suitable solvent such as 2-propa-nol, dioxane, THF, NMP, DMA, DMF or toluene/water mixture and in the presence of a suitable base such as potassium tert-butoxide, NaH, potassium carbonate, pyri-dine, triethylamine or N-ethyl-diisopropylamine to give compounds of general formula (I). Additionally, Buchwald-Hartwig-type cross coupling conditions may be used to form final compounds (I). For example, compounds (XII) (X=Cl, Br, I) may be reacted with amines (V) in a suitable solvent such as toluene in the presence of a suitable catalyst such as palladium(II) acetate and a suitable ligand such as butyl-di-1-adamantyl-phosphine and a suitable base such as cesium carbonate to provide compounds of the general formula (I).

Alternatively, halo amide (XII) may be reacted with hydroxy azetidine in a nucleophilic aromatic substitution reaction, in a suitable solvent such as DMA or the like and in the presence of a suitable base such as triethylamine, to give alcohols of the general formula (XIII). In a subsequent step, alcohols (XIII) may be converted into compound of general formula (I) using the "Mitsunobu" method (see for examples *Tet. Lett.* 1994, 35, 2819 or *Synlett* 2005, 18, 2808): trialkyl or triaryl phosphine (such as tributyl phosphine or triphenyl phosphine) or solid-supported analogues such as polymer-bound triphenyl phosphine and a suitable dialkyl azadicarboxylate (e.g. DIAD, DEAD) are added to a compound of general formula (XIII) in the presence of an appropriate phenol (III) in a suitable solvent (e.g. THF or toluene) to generate compounds of the general formula (I).

Schemes 5 and 6 illustrate the synthesis of amines of general formula (X) as intermediates for the synthesis of compounds of general formula (I).

(XV). In a second step the alcohol (XV) is fluorinated with a fluorinating agent such as (diethylamino)sulfur trifluoride (DAST) or bis(2-methoxyethyl)aminosulfur trifluoride (Deoxo-Fluor) in a solvent like dichloromethane to give the corresponding trans-substituted azido fluoride. In a third step, reduction of azide (XVI) can be achieved by catalytic hydrogenation (for example, hydrogenation with hydrogen using palladium on charcoal in methanol or ethanol) or by addition of triphenyl phosphine (Staudinger reaction) and subsequent heating of the intermediate iminophosphorane with water in THF to provide racemic trans-substituted monofluoro amino pyrrolidines (XVII).

Corresponding cis-substituted monofluoro amino pyrrolidines (XXI) may be synthesized by an analogous sequence (steps 6 and 7) starting from racemic cis-substituted azido alcohols (XVIII) which can be prepared by inverting stereochemistry of the hydroxy group in compound (XV) using conventional techniques (e.g., activation as sulfonyl ester and subsequent nucleophilic displacement with potassium acetate (e.g., R=CH$_3$) followed by saponification; see, for example: *Tet. Asymm.* 2001, 12, 1793-1799).

Scheme 5

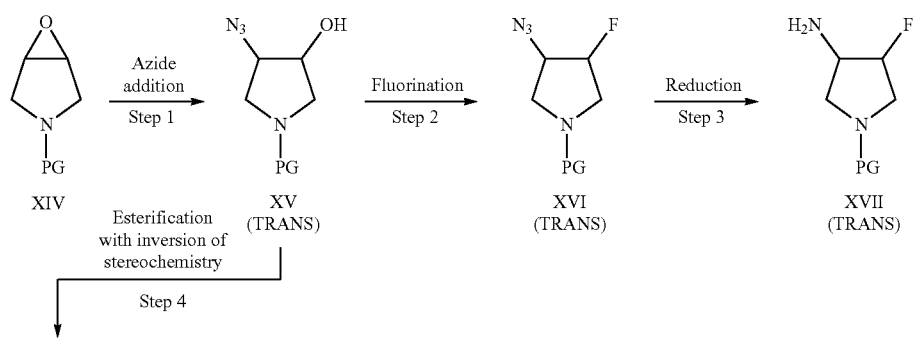

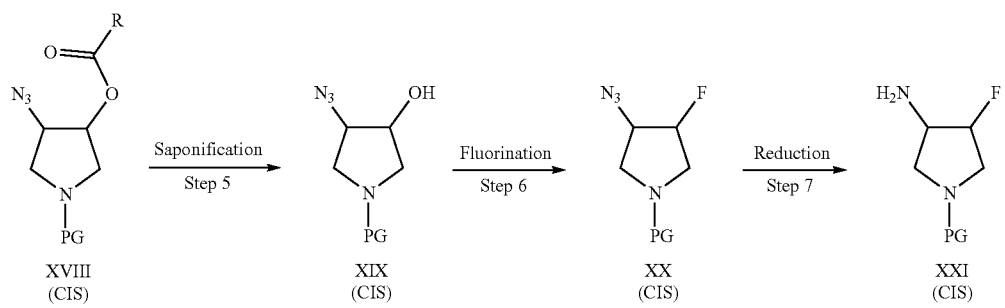

Mono-fluorinated amino pyrrolidines of the general formula (XVII) or (XXI) may be prepared as illustrated in scheme 5. An appropriately protected 6-oxa-3-azabicyclo[3.1.0]hexane (XIV) (PG=protecting group, e.g., CO$_2$tBu or acetyl) is reacted with an azide source such sodium azide or tetrabutyl ammonium azide in a suitable solvent like DMF or DMA to give racemic trans-substituted azido alcohol Enantioselective epoxide ring opening of 6-oxa-3-azabicyclo[3.1.0]hexane (XIV) with chiral metal salen complexes and trimethylsilyl azide (*J. Am. Chem. Soc.* 1995, 117, 5897) can provide access to trans-enantio-enriched precursors of general formula (XV), which can be converted into the respective chiral fluorinated amino pyrrolidines (XVII) and (XXI) (see, for example, *Synlett* 2019, 30, 1228-1230).

Scheme 6

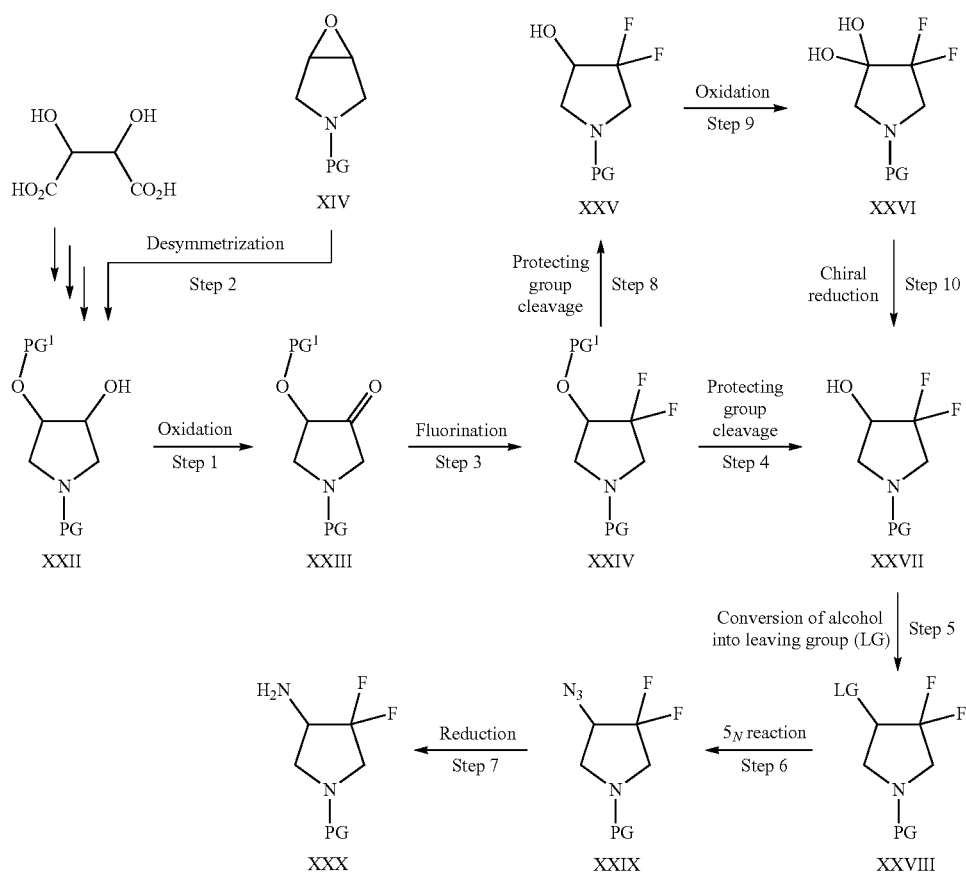

Difluorinated amino pyrrolidines of the general formula (XXX) may be prepared as illustrated in scheme 6. 6-Oxa-3-azabicyclo[3.1.0]hexane (XIV) (PG=protecting group, e.g., CO$_2$tBu (BOC) or acetyl) may be desymmetrized in a one- or two-step procedure giving mono-protected pyrrolidinediols of general formula (XXII). For example, nucleophilic epoxide opening with sodium benzyl alcoholate can produce racemic compounds of the general formula (XXII) (e.g., PG$^1$=benzyl) in a one-step process (see, for example, WO199964399, p 20). Alternatively, epoxide opening with a hydroxide source like sodium hydroxide will lead to an intermediate pyrrolidinediol, which can selectively be mono-protected using common protecting group strategies (for example, reaction with a stoichiometric amount of tert-butyl dimethyl silyl chloride in the presence of a base like imidazole in a solvent like DMF may yield racemic compounds (XXII) (PG$^1$=tert-butyldimethylsilyl). Alcohols of the general formula (XXII) can be converted to ketones of general formula (XXIII). For example, compounds (XXII) may be oxidized with Dess-Martin periodinane or by using a combination of oxalyl chloride and DMSO (Swern oxidation, see, for example, WO2010111057, p 28) in an inert solvent like dichloromethane. In a third step, ketones (XXIII) may be reacted with a deoxo-fluorinating agent like (diethylamino)sulfur trifluoride (DAST) or bis(2-methoxyethyl)aminosulfur trifluoride (Deoxo-Fluor, see, for example, W2014075392, p 72) in a solvent like dichloromethane to give the corresponding difluorides (XXIV). These intermediates are deprotected in a fourth step to give alcohols (XXVII). Deprotection may be achieved by using tetrabutylammonium fluoride on silyl-protected intermediates (XXIV) or by catalytic hydrogenation using a catalyst like palladium on charcoal under an atmosphere of hydrogen on benzyl-protected intermediates (XXIV). Additional deprotection reactions are described in 'Protective Groups in Organic Synthesis', 3' edition, T. W. Greene and P. G. M. Wuts, Wiley-Interscience (1999).

The hydroxy group of pyrrolidine (XXVII) can be converted into a suitably activated leaving group (e.g., LG=methylsulfonylate, trifluoromethylsulfonylate, p-tosylate) in a fifth step by reaction with a suitable sulfonyl acid derivative (e.g., methyl sulfonyl chloride, trifluoromethylsulfonyl acid anhydride, p-tosyl chloride or the like) in presence of base like triethylamine or pyridine in a solvent like dichloromethane, THF or the like to produce corresponding sulfonyl esters of general formula (XXVIII).

In a sixth step, the suitably activated pyrrolidines (XXVIII) can be reacted in a nucleophilic substitution with an azide source such as sodium azide or tetrabutylammonium azide in a suitable solvent like DMF or DMA to yield azido pyrrolidines (XXIX), which may be reduced in a subsequent step by catalytic hydrogenation (for example, hydrogenation with hydrogen using palladium on charcoal in methanol or ethanol) or by addition of triphenyl phosphine (Staudinger reaction) and subsequent heating of the intermediate iminophosphorane with water in THF to provide difluoro amino pyrrolidines of general formula (XXX).

Conventional techniques for the preparation/isolation of individual enantiomers include chiral synthesis from a suitable optically pure precursor. For example, a suitable optically pure precursor can be obtained from tartaric acid, which can be converted into chiral mono-protected pyrrolidinediols of general formula (XXII) (see, for example: *Tet. Asymm.* 2001, 12, 1793-1799 or *Org. Process Res. Dev.* 2019, 23, 1970-1978) and following the previously described reaction sequence can lead to chiral fluorinated amino pyrrolidines of general formula (XXX) or (XVII).

An alternative method to synthesize chiral amino pyrrolidines (XXX) may involve the chiral reduction of a ketone hydrate of general formula (XXVI) by asymmetric transfer hydrogenation using iridium-catalyzed conditions with N-(p-toluenesulfonyl)-1,2-diphenylethylenediamine as ligand and sodium formate as reductant (see, for example, *J. Org. Chem.* 2016, 81, 4359-4363), which can provide optically active alcohols of general formula (XXVII). Ketone hydrate precursors (XXVI) may be obtained by oxidation of alcohols (XXV) using potassium peroxymonosulfate (e.g. Oxone™) in presence of 2-iodoxybenzenesulfonic acid (see, for example, *J. Am. Chem. Soc.* 2009, 131, 251), by using Dess-Martin periodinane in dichloromethane (see, for example, *J. Org. Chem.* 2010, 75, 929-932), or by using sodium hypochlorite with TEMPO (2,2,6,6-tetramethylpiperidin-1-yl)oxyl) as catalyst (see, for example, *Org. Process Res. Dev.* 2015, 19, 270-283). Chiral alcohols (XXVII) may be converted into the corresponding chiral amines (XXX) following an analogous sequence of reaction steps as described in scheme 6.

A further alternative method to synthesize chiral amino pyrrolidines (XXX) may involve the chiral conversion of a ketone/hydrate form of general formula (XXVI) by asymmetric enzymatic reaction using for example a transaminase (see, for example, *Green Chem.* 2019, 21, 75-86).

Alternatively, the racemic amine(s) (or a racemic precursor thereof) may be reacted with a suitable optically active compound, for example, an acid such as phenyl succinic acid or di-benzoyltartaric acid in isopropanol or ethanol/water mixtures. The resulting diastereomeric mixture may be separated by chromatography and/or fractional crystallization and one or both diastereoisomers converted to the corresponding pure enantiomer(s) by means well known to a skilled person (see, for example, the resolution of amino pyrrolidines of general formula (XVII): US2015/141402, pag. 48).

Chiral compounds of the invention of general formula (I) (and chiral precursors thereof) may be obtained in enantiomerically-enriched form using chromatography, typically supercritical fluid chromatography (SFC), on a resin with an asymmetric stationary phase and with a mobile phase consisting of supercritical $CO_2$, containing for example 15% to 35% methanol (% v/v) and 20 mM concentrated aqueous ammonia. Concentration of the eluate affords the enriched mixture. Mixtures of stereoisomers may be separated by conventional techniques known to those skilled in the art [see, for example, "Stereochemistry of Organic Compounds" by E L Eliel (Wiley, New York, 1994)].

BIOLOGICAL ASSAYS AND DATA

The numbers in table 3 to 7 refer to the compounds of the invention (i.e. Example or Intermediate) disclosed in the experimental section below.

Homogeneous Time-Resolved Fluorescence (HTRF) Assay for Direct cAMP Measurement

HTRF cAMP assays were performed using commercially available assay kits according to the manufacturer's instructions (cAMP Dynamic 2 Assay Kit; #62AM4PEJ, Cisbio Bioassays, Bedford, MA). An aliquot of CHO-K1 cells stably expressing recombinant human GPR52 was thawed and resuspended in cell buffer (1×PBS (w/o $Ca^{2+}/Mg^{2+}$)) at a density of $4 \times 10^5$ cells per mL. Test compounds were solubilized in DMSO to 10 mM stock solutions and serially diluted in DMSO using 6-fold dilutions to generate 8-point dose response curves. These serially diluted samples were then diluted 1:50 in compound dilution buffer (1×PBS (w/o $Ca^{2+}/Mg^{2+}$) containing 0.5 mM IBMX, 0.1% BSA) to achieve a 4× stock. The diluted compounds were transferred (5 µL per well) in duplicate to the 384-well assay plate (Optiplate #6007290, PerkinElmer, Waltham, MA). Both a positive (reference compound) and negative (non-stimulated vehicle) control was included in each assay run in column 23. The cell suspension was subsequently dispensed into the 384-well assay plates at 15 µL per well (6000 cells) such that the compound was diluted to 1×. Column 24 on the plates did not receive cells and was reserved for a cAMP standard curve. After a one-hour incubation at room temperature, 10 µL of cAMP D2 reagent followed by 10 µL of cryptate reagent (provided in the Cisbio kit) was added to each well. Plates were then incubated at room temperature for one hour prior to reading. Time-resolved fluorescence measurements were collected on an EnVision® HTRF plate reader (PerkinElmer, Waltham, MA). Counts from the plate reader were fit to the cAMP standard curve included on each plate to determine the amount of cAMP in each test well. The % control was calculated based on the positive control set at 200% and the negative control set at 100%. Dose-response curves were generated from the cAMP data and analyzed using a nonlinear least squares curve-fitting program to obtain $EC_{50}$ values. Mean $EC_{50}$ values are provided in table 3.

TABLE 3

Activity of the examples (Ex.) and intermediates (Int.) compiled in the experimental part, based on the above described HTRF assay

| Ex./Int. | GPR52 $EC_{50}$ [µM] | Ex./Int. | GPR52 $EC_{50}$ [µM] | Ex./Int. | GPR52 $EC_{50}$ [µM] | Ex./Int. | GPR52 $EC_{50}$ [µM] |
|---|---|---|---|---|---|---|---|
| Ex. 1 | 0.015 | Ex. 2 | 0.024 | Ex. 3 | 0.092 | Ex. 4 | 0.018 |
| Ex. 5 | 0.027 | Ex. 6 | 0.054 | Ex. 7 | 0.102 | Ex. 8a | 1.091 |
| Ex. 8b | 0.007 | Ex. 9 | 0.019 | Ex. 10a | 0.014 | Ex. 10b | 1.329 |
| Ex. 11a | 1.280 | Ex. 11b | 0.010 | Ex. 12 | 0.024 | Ex. 13a | 0.595 |
| Ex. 13b | 0.003 | Ex. 14a | 1.173 | Ex. 14b | 0.011 | Ex. 15a | 0.020 |
| Ex. 15b | 0.168 | Ex. 16a | 0.011 | Ex. 16b | 0.210 | Int. H-3 | 0.378 |

In Vitro Metabolite Profiling

In vitro metabolite profiling to evaluate the involvement of non-CYP-enzyme-mediated metabolic pathways such as hydrolysis in addition to CYP-mediated pathways is based on the semiquantitative analysis of the formation of prototypic metabolites in incubations with liver microsomes (with and without beta-nicotinamide adenine dinucleotide phosphate, NADPH), primary human hepatocytes (with and without the pan-CYP inhibitor proadifen) and recombinant CYP enzymes.

The involvement of hydrolases, such as carboxylesterases or arylacetamide deacetylase, is assumed if the metabolite resulting from amide hydrolysis of a compound of the present invention of general formula (I) wherein $R^6$ is an acetyl-group, i.e. the deacetylated compound thereof, is not formed in presence of the relevant drug-metabolizing human recombinant CYP enzymes but is formed in human liver microsomes in the absence of NADPH. Hydrolases are highly abundant in liver microsomes; however, in contrast to CYP-related metabolic processes, the catalytic activity of hydrolases is independent of NADPH. As such, the deacetylated metabolite would be formed in incubations of human liver microsomes lacking NADPH.

A phenotyping assay was performed to identify the CYP enzymes responsible for metabolic conversion of the compound. The metabolic degradation of the test compound and the assessment of formation of metabolites was performed using Supersomes (human CYP expressed in baculovirus infected insect cells) and human liver microsomes, respectively. Compounds were tested specifically for their conversion by CYP isoenzymes 1A1, 1A2, 2B6, 2C8, 2C9, 2C19, 2D6, 3A4 and 3A5.

Incubations in TRIS buffer (0.1 M, pH 7.6, supplemented with 5 mM magnesium chloride) consisted of 200 pmol/ml of the respective protein from Supersomes or 4 mg/ml of a human liver microsomal preparation and 10 µM test compounds.

Following a short preincubation period for 15 min at 37° C., the reaction was initiated by addition of NADPH (reduced form, 1 mM). Additional incubations with human liver microsomes were conducted in the absence of NADPH. After 60 min at 37° C., the incubations were terminated by transferring an aliquot of sample into acetonitrile. Samples were analyzed for formation of putative metabolites by means of by liquid chromatography-high resolution mass spectrometry.

An additional measure to identify CYP-independent metabolic pathways is the use of the pan-CYP inhibitor proadifen in incubations of the test compound with human hepatocytes. In presence of proadifen, the CYP-related pathways are inhibited and metabolites would primarily be generated via non-CYP pathways.

The involvement of non-CYP-enzymes in metabolic transformations of the test compound was further investigated using primary human hepatocytes in suspension in presence or absence of the pan-CYP inhibitor proadifen (50 µM final incubation concentration). After recovery from cryopreservation, human hepatocytes were incubated in Dulbecco's modified eagle medium supplemented with 3.5 µg glucagon/500 ml, 2.5 mg insulin/500 ml and 3.75 mg/500 ml hydrocortisone containing 5% (v/v) human serum.

Following a 30 min preincubation in a cell culture incubator (37° C., 10% $CO_2$) with or without 50 µM proadifen, test compound solution was spiked into the hepatocyte suspension to obtain a final cell density of $1.0*10^6$ to $4.0*10^6$ cells/ml (depending on the metabolic turnover rate of the compound observed with primary human hepatocytes), a final test compound concentration of 1 µM, and a final DMSO concentration of 0.05% (v/v).

The cells were incubated for six hours (incubator, horizontal shaker) and samples were removed from the incubation after 0, 0.5, 1, 2, 4 or 6 hours, depending on the metabolic turnover rate. Samples were quenched with acetonitrile and pelleted by centrifugation. The supernatant was transferred to a 96-deepwell plate, evaporated under nitrogen, and resuspended prior to bioanalysis by liquid chromatography-high resolution mass spectrometry for identification of putative metabolites.

The contribution of hydrolysis was calculated based on the abundance of the respective deacetylated metabolite(s) of the compounds of the present invention relative to all metabolites observed in incubations with human hepatocytes.

TABLE 4

In vitro metabolite profiling of examples (Ex.) of the present invention.

| Ex. | % Parent of drug-related material[1] [%] | Main metabolites formed via amide hydrolysis[1, 2] | % Inhibition by 50 µM proadifen[1] [% untreated control] | Formation in human liver microsomal incubations in absence of NADPH[3] [yes/no] | Specific formation in human recombinant CYP enzymes[4] [yes/no] | Contribution of amide hydrolysis to metabolism[1] (incl. secondary metabolites) [%] |
|---|---|---|---|---|---|---|
| 8b | 84 | m411 | <0 | yes | no | 19 |
| 10a | 86 | m411 | <0 | yes | no | 51 |
|  |  | m425[5] | 87[5] | no[5] | no[5] |  |
|  |  | m405[5] | 91[5] | no[5] | no[5] |  |
| 11b | 82 | m429 | <0 | yes | no | 49 |
|  |  | m443[6] | 82[6] | no[6] | no |  |
| 13b | 70 | m417 | <0 | yes | no | 25 |
| 15a | 92 | m381 | not tested | yes | no | 6 |

[1]Based on incubations in primary human hepatocytes.
[2]Only metabolites shown for which amide hydrolysis occurs.
[3]"yes": Metabolite is formed in presence of human liver microsomes in the absence of cofactors as indication of a non-CYP-dependent pathway; "no": Metabolite is not detected in microsomal incubations.
[4]"yes": Metabolite is formed in presence of human recombinant CYP-enzymes; "no": Metabolite is not detected in presence of human recombinant CYP-enzymes as indication of a non-CYP-dependent pathway.
[5]m425 and m405 are secondary metabolites of m411; their formation involves an additional CYP-dependent metabolic component.
[6]m443 is a secondary metabolite of m429; its formation involves an additional CYP-dependent metabolic component.

hERG (Human Ether-à-go-go-Related Gene)-Channel Assay hERG Channel inhibition of compounds of the present invention was investigated as follows:

Cells:

HEK (human embryonic kidney) 293 cells were stably transfected with hERG cDNA. Cells determined for use in patch clamp experiments were cultivated without antibiotic.

Pipettes and Solutions:

Cells were superfused with a bath solution containing (mM): NaCl (137), KCl (4.0), MgCl$_2$ (1.0), CaCl$_2$(1.8), Glucose (10), HEPES (10), pH 7.4 with NaOH. Patch pipettes were made from borosilicate glass tubing using a pipette and filled with pipette solution containing (mM): K-aspartate (130), MgCl$_2$(5.0), EGTA (5.0), K2ATP (4.0), HEPES (10.0), pH 7.2 with KOH. Resistance of the microelectrodes was typically in the range between 2 MΩ and 5 MΩ.

Stimulation and Recording:

Membrane currents were recorded using an EPC-10 patch clamp amplifier (HEKA Electronics, Lambrecht, FRG) and PatchMaster software (HEKA). hERG-mediated membrane currents were recorded at typically 28° C., using the whole-cell configuration of the patch-clamp technique. Transfected HEK293 cells were clamped at a holding potential of −60 mV and hERG-mediated inactivating tail currents were elicited using a pulse pattern with fixed amplitudes (activation/inactivation: 40 mV for 2000 ms; recovery: 120 mV for 2 ms; ramp to 40 mV in 2 ms; inactivating tail current: 40 mV for 50 ms) repeated at 15 s intervals. During each inter-pulse interval 4 pulses scaled down by a factor of 0.2 were recorded for a P/n leak subtraction procedure. Rs compensation was employed up to a level that safely allows recording devoid of ringing. The remaining uncompensated Rs was recorded as well as actual temperature and holding current.

Compound Preparation and Application:

The concentrations of the test item were applied sequentially on each of the different cells investigated. A steady state level of baseline current was measured for at least 5 sweeps prior to the application of the first test article concentration. The test item was dissolved in DMSO to yield a stock solution of 1000-fold the highest final concentration. This stock was diluted further in DMSO to stock solutions of 1000-fold the remaining final concentrations. Final dilutions in extracellular buffer were prepared freshly from these stocks by a 1:1000 dilution step each before starting the experiments.

Data Analysis:

Peak current amplitudes were measured 3 ms after the ramp to +40 mV. For baseline and each concentration, the peak currents of the three last sweeps before application of the next concentration were averaged. Residual currents (I/I0) were calculated for each cell as the fraction of actual average peak current and average baseline peak current. Current inhibition was expressed as (1−I/I0)*100%. Current inhibition for all cells was reported as mean ±SD. If possible, from mean current inhibition data the IC$_{50}$ was estimated based on the Hill equation using a least squares procedure.

TABLE 5 hERG channel inhibition of examples of the present invention.

| Example | hERG IC$_{50}$ [µM] | Example | hERG IC$_{50}$ [µM] | Example | hERG IC$_{50}$ [µM] | Example | hERG IC$_{50}$ [µM] |
|---|---|---|---|---|---|---|---|
| 1 | >10 | 2 | 6.6 | 3 | >10 | 4 | >10 |
| 5 | >10 | 6 | >10 | 8b | >10 | 9 | >10 |
| 10a | >10 | 11b | >10 | 12 | >10 | 13b | >10 |
| 14b | >10 | 15a | >10 | 16a | >10 | 16b | >10 |

Human Plasma Protein Binding Assay

Equilibrium dialysis (ED) technique was used to determine the approximate in vitro fractional binding of test compounds to plasma proteins. Dianorm Teflon dialysis cells (micro 0.2) were used. Each dialysis cell consists of a donor and an acceptor chamber, separated by an ultrathin semipermeable membrane with a 5 kDa molecular weight cut-off. Stock solutions for each test compound were prepared in DMSO at 1 mM and serially diluted to obtain a final test concentration of 1 µM. The subsequent dialysis solutions were prepared in plasma (supplemented with NaEDTA as anticoagulant), and aliquots of 200 µL test compound dialysis solution in plasma were dispensed into the donor (plasma) chambers. Aliquots of 200 µL dialysis buffer (100 mM potassium phosphate, pH 7.4) were dispensed into the buffer (acceptor) chamber. Incubation was carried out for 2 hours under rotation at 37° C. for establishing equilibrium.

At the end of the dialysis period, aliquots obtained from donor and acceptor chambers, respectively, were transferred into reaction tubes, spiked with Internal Standard solution and processed for HPLC-MS/MS analysis. Analyte concentrations were quantified in aliquots of samples by HPLC-MS/MS against external calibration curves.

Percent bound was calculated using the formula:

% bound=(plasma concentration−buffer concentration/plasma concentration)×100

TABLE 6

Human plasma protein binding of examples (Ex.) and intermediates (Int.) of the present invention.

| Ex./Int. | Hu PPB [% bound] | Ex./Int. | Hu PPB [% bound] | Ex./Int. | Hu PPB [% bound] | Ex./Int. | Hu PPB [% bound] |
|---|---|---|---|---|---|---|---|
| Ex. 1 | 92.6 | Ex. 2 | 89.9 | Ex. 3 | 72.3 | Ex. 4 | 79.2 |
| Ex. 5 | 93.2 | Ex. 6 | 87.8 | Ex. 8b | 79.7 | Ex. 9 | 93.4 |
| Ex. 10a | 82.4 | Ex. 11b | 84.4 | Ex. 12 | 88.5 | Ex. 13b | 92.8 |
| Ex. 14b | 89.7 | Ex. 15a | 90.2 | Ex. 16a | 86.2 | Int. H-3 | 88.2 |

Metabolic Stability in Human Hepatocytes

The metabolic degradation of a test compound was assayed in a human hepatocyte suspension. After recovery from cryopreservation, human hepatocytes were diluted in Dulbecco's modified eagle medium (supplemented with 3.5 µg glucagon/500 mL, 2.5 mg insulin/500 mL, 3.75 mg hydrocortisone/500 mL, 5% human serum) to obtain a final cell density of $1.0 \times 10^6$ cells/mL or $4.0 \times 10^6$ cells/mL, depending on the metabolic turnover rate of the test compound.

Following a 30 minutes preincubation in a cell culture incubator (37° C., 10% $CO_2$), test compound solution was spiked into the hepatocyte suspension, resulting in a final test compound concentration of 1 µM and a final DMSO concentration of 0.05% (v/v).

The cell suspension was incubated at 37° C. (cell culture incubator, horizontal shaker) and samples were removed from the incubation after 0, 0.5, 1, 2, 4 and 6 hours. Samples were quenched with acetonitrile (containing internal standard) and pelleted by centrifugation. The supernatant was transferred to a 96-deepwell plate, and prepared for analysis of decline of parent compound by HPLC-MS/MS.

The percentage of remaining test compound was calculated using the peak area ratio (test compound/internal standard) of each incubation time point relative to the time point 0 peak area ratio. The log-transformed data were plotted versus incubation time, and the absolute value of the slope obtained by linear regression analysis was used to estimate in vitro half-life (T1/2).

In vitro intrinsic clearance (CLint) was calculated from in vitro T1/2 and scaled to whole liver using a hepatocellularity of $120 \times 10^6$ cells/g liver, a human liver per body weight of 25.7 g liver/kg as well as in vitro incubation parameters, applying the following equation:

CL_INTRINSIC_IN VIVO[mL/min/kg]=(CL_IN-TRINSIC[µL/min/$10^6$ cells]×hepatocellularity [$10^6$ cells/g liver]×liver factor[g/kg body weight])/1000

Hepatic in vivo blood clearance (CL) was predicted according to the well-stirred liver model considering an average liver blood flow (QH) of 20.7 mL/min/kg:

CL[mL/min/kg]=CL_INTRINSIC_IN VIVO[mL/min/kg]×hepatic blood flow[mL/min/kg]/(CL_INTRINSIC_IN VIVO[mL/min/kg]+hepatic blood flow[mL/min/kg])

Results were expressed as percentage of hepatic blood flow:

QH[%]=CL[mL/min/kg]/hepatic blood flow[mL/min/kg])

TABLE 7

Human hepatocyte stability of examples (Ex.) and intermediates (Int.) of the present invention.

| Ex./Int. | Human HepStab [% QH] | Ex./Int. | Human HepStab [% QH] | Ex./Int. | Human HepStab [% QH] | Ex./Int. | Human HepStab [% QH] |
|---|---|---|---|---|---|---|---|
| Ex. 1 | 11.1 | Ex. 2 | 21.3 | Ex. 3 | <4.1 | Ex. 4 | 8.5 |
| Ex. 5 | 17.0 | Ex. 6 | 4.8 | Ex. 7 | 15.4 | Ex. 8b | 9.2 |
| Ex. 9 | 5.8 | Ex. 10a | 15.3 | Ex. 11b | 11.4 | Ex. 12 | 5.0 |
| Ex. 13b | <4.1 | Ex. 14b | <4.1 | Ex. 15a | 6.4 | Ex. 16a | <4.1 |
| Int. H-3 | 27.7 | | | | | | |

Solubility Assessment

Solubility of compounds of the present invention were investigated by a high throughput solubility assay as follows.

Test compounds were solubilized in DMSO to 10 mM stock solutions and further diluted in acetonitrile/water (1:1 v/v) solution, McIlvaine buffer solution pH 2.2, McIlvaine buffer solution pH 4.5, and McIlvaine buffer solution pH 6.8 using 40-fold dilutions in a 96-well plate format (McIlvaine buffer is a citrate-phosphate buffer). The well plates with the diluted samples were sealed and shaken upside down for 24 hours at room temperature.

Undissolved particles were removed by centrifuge filtration and the resulting sample solutions were analyzed by automated UV-absorption on HPLC (default wavelength: 254 nm). If the absorption was too low, alternative wavelengths of 280 nm or 230 nm were used for improved detection. Analyte concentrations were quantified by HPLC-UV. Quantification was done via one-point calibration using the sample dissolved in acetonitrile/water as the calibration point. The solubility of some compounds of the present invention was also determined by a solid-state solubility assay as follow.

Saturated solutions were prepared in well plates (format depends on robot) by adding an appropriate volume of selected aqueous media (typically in the range of 0.25 ml-1.5 ml) into each well which contains a known quantity of solid drug substance (typically in the range 0.5 mg-5.0 mg). The wells were shaken or stirred for a predefined time period (typically in a range of 2 h-24 h) and then filtered using appropriate filter membranes (typically PTFE-filters with 0.45 µm pore size). Filter absorption was avoided by discarding the first few drops of filtrate. The amount of dissolved drug substance was determined by UV spectroscopy. In addition, the pH of the aqueous saturated solution was measured using a glass-electrode pH meter.

In view of their ability to activate GPR52, their low human protein binding and their high human hepatocyte stability which translate potentially into reasonably low efficacious doses of the compounds for disease treatment and as a consequence in a potential minimization of side effects, their low/moderate hERG channel inhibition, their diversified metabolism comprising a hydrolase-mediated pathway (where applicable) with subsequently reduced risk for CYP-mediated drug-drug-interactions, the compounds of general formula (I) according to the invention, or the pharmaceutically acceptable salts thereof, are suitable for the treatment and/or preventative treatment of all those diseases or conditions which can be influenced by activation of GPR52, preferably central nervous system diseases or conditions herein disclosed.

Use in Treatment/Method of Use

Therefore, compounds according to the invention or compositions comprising at least one compound of the invention, including the pharmacological acceptable salts thereof, are particularly suitable for use in the prevention and/or treatment of diseases which can be influenced by activation of GPR52, such as psychiatric disorders, psychotic disorders, cognitive disorders, depressive disorders, anxiety disorders, obsessive-compulsive disorder (OCD), impulse-control disorders, substance-related disorders, and motor and movement disorders.

In a further aspect, the present invention relates to compounds according to general formula (I) or pharmaceutically acceptable salts thereof, or pharmaceutical compositions comprising compounds according to general formula (I) or pharmaceutically acceptable salts thereof, for use in the prevention and/or treatment of diseases or conditions selected in the group consisting of: schizophrenia; positive symptoms associated with: schizophrenia, schizoaffective disorder, schizophreniform disorder, schizotypal disorder, treatment resistant schizophrenia, attenuated psychosis syndrome and autism-spectrum disorder; augmentation of antipsychotics to treat the positive symptoms associated with: schizophrenia, schizoaffective disorder, schizophreniform disorders, schizotypal disorder, treatment resistant schizophrenia, attenuated psychosis syndrome and autism-spectrum disorder, or to lower the dose (and thereby side effects) of antipsychotics; negative symptoms associated with: schizophrenia, schizoaffective disorder, schizophreniform disorder, schizotypal disorder, treatment resistant schizophrenia, attenuated psychosis syndrome and autism-spectrum disorder; cognitive impairment associated with: schizophrenia (CIAS), schizoaffective disorder, schizophreniform disorder, schizotypal disorder, treatment resistant schizophrenia, attenuated psychosis syndrome and autism-spectrum disorder; treatment resistant schizophrenia; schizoaffective disorder; schizophreniform disorder; schizotypal (personality) disorder; drug-induced psychosis; bipolar I and II disorder; attenuated psychosis syndrome; neuropsychiatric symptoms associated with: Alzheimer's Disease, Parkinson's Disease, vascular dementia, and frontotemporal dementia; autism spectral disorder (ASD); obsessive-compulsive disorder (OCD); impulse-control disorder (e.g. impulse control disorder induced by D2 receptor agonists); gambling disorder (e.g. gambling disorder induced by D2 receptor agonists); Tourette's syndrome; cognitive deficits associated with: Alzheimer's disease, Parkinson's disease, vascular dementia and frontotemporal dementia; depression; attention deficit hyperactivity disorder (ADHD); major depressive disorder (MDD); drug addiction; anxiety; mania in bipolar disorder; acute mania; agitation; detachment; hypothalamic disorders; prolactin-related disorders such as hyperprolactinemia; symptoms associated with hypofrontality (e.g. hypofrontality associated with drug abuse) and hyperkinetic symptoms.

Preferably the compounds according to the invention are suitable for the prevention or treatment of schizophrenia; positive symptoms associated with schizophrenia; augmentation of antipsychotics to treat the positive symptoms associated with schizophrenia or to lower the dose, and thereby side effects, of antipsychotics; negative symptoms associated with schizophrenia; cognitive impairment associated with schizophrenia (CIAS); treatment resistant schizophrenia; schizoaffective disorder; schizophreniform disorder; schizotypal disorder; drug-induced psychosis; bipolar I and II disorder; attenuated psychosis syndrome; neuropsychiatric symptoms associated with Alzheimer's Disease, Parkinson's Disease, vascular dementia, and frontotemporal dementia; autism spectral disorder (ASD); impulse control disorder (e.g. impulse control disorder induced by D2 receptor agonists); gambling disorder (e.g. gambling disorder induced by D2 receptor agonists); and prolactin-related disorders such as hyperprolactinemia.

In a further aspect the present invention relates to the use of a compound of general formula (I) for the preparation of a medicament for the treatment and/or prevention of above-mentioned diseases and conditions.

In a further aspect of the present invention the present invention relates to methods for the treatment and/or prevention of above mentioned diseases and conditions, which method comprises the administration of an effective amount of a compound of general formula (I), or the pharmaceutically acceptable salts thereof, to a human being.

The dose range of the compounds of general formula (I) applicable per day is usually from 0.1 mg to 1000 mg, preferably from 1 mg to 500 mg by oral route, in each case administered 1 to 4 times a day. Each dosage unit may conveniently contain from 0.1 mg to 500 mg, preferably 1 mg to 100 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Suitable preparations for administering the compounds of general formula (I), including the pharmaceutically acceptable salts thereof, will be apparent to those skilled in the art and include for example tablets, pills, capsules, suppositories, lozenges, troches, solutions, syrups, elixirs, sachets, injectables, inhalatives, powders, etc. The content of the pharmaceutically active compound(s) should be in the range from 0.1 to 95 wt.-%, preferably 5.0 to 90 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers.

For this purpose, the compounds of general formula (I) prepared according to the invention may be formulated, optionally together with other active substances, together with one or more inert conventional carriers and/or diluents, e.g. with corn starch, lactose, glucose, microcrystalline cellulose, magnesium stearate, citric acid, tartaric acid, water, polyvinylpyrrolidone, water/ethanol, water/glycerol, water/sorbitol, water/polyethylene glycol, propylene glycol, cetylstearyl alcohol, carboxymethylcellulose or fatty substances such as hard fat or suitable mixtures thereof.

Combination Therapy

Additionally, compounds according to the invention, are particularly suitable as a co-medication (i.e. combination, adjunctive therapy) with currently prescribed antipsychotics to treat in addition to the positive symptoms associated with schizophrenia also the cognitive and/or negative symptoms. Regarding treatment of the positive symptoms, the co-medication with antipsychotics may result not only in improved anti-psychotic efficacy (e.g. improvement in the treatment of positive symptoms associated with schizophrenia), but could also be combined with reduced doses of antipsychotic drugs, to lower their associated side effects, such as weight gain, metabolic syndrome, diabetes, extrapyramidal symptoms, hyperprolactinemia, insulin resistance, hyperlipidemia, hyperglycemia and/or tardive dyskinesia. Particularly, increased serum prolactin levels are a prominent side effect profile of antipsychotics, whereas activators of GPR52 have been demonstrated to lower serum prolactin levels. Therefore, a co-application of GPR52 agonists with antipsychotics may normalize serum prolactin levels, thereby lowering the side effects associated with antipsychotics.

Therefore, the compounds of general formula (I) according to the invention may be used in conjunction (e.g. as adjunctive therapy) with other active substances (i.e. combination partner), particularly for the treatment and/or prevention of the diseases and conditions mentioned above (i.e. paragraph Use in treatment/method of use). Other active substances which are suitable for such combination may be selected in the group consisting of: BACE inhibitors; amyloid aggregation inhibitors (e.g. ELND-005); directly or indirectly acting neuroprotective and/or disease-modifying substances; anti-oxidants (e.g. vitamin E or ginkolide); anti-inflammatory substances (e.g. COX inhibitors, NSAIDs additionally or exclusively having Abeta lowering properties); HMG-CoA reductase inhibitors (statins); acetylcholinesterase inhibitors (e.g., donepezil, rivastigmine, tacrine, galantamine); NMDA receptor antagonists (e.g. memantine, ketamine, esketamine, NR2b antagonists); AMPA receptor agonists; AMPA receptor positive modulators, AMPAkines, monoamine receptor reuptake inhibitors, substances modulating the concentration or release of neurotransmitters; substances inducing the secretion of growth hormone (e.g., ibutamoren mesylate and capromorelin); CB-1 receptor antagonists or inverse agonists; antibiotics (e.g., minocyclin or rifampicin); PDE1, PDE2, PDE4, PDE5, PDE9, PDE10 inhibitors, GABAA receptor agonists or positive modulators, GABAA receptor inverse agonists, GABAA receptor antagonists, nicotinic receptor agonists or partial agonists or positive modulators, alpha4beta2 nicotinic receptor agonists or partial agonists or positive modulators, alpha7 nicotinic receptor agonists or partial agonists or positive modulators; Somatostatin receptor 4 agonists or partial agonists or positive modulators, histamine H3 antagonists, 5HT-4 agonists or partial agonists, 5HT-6 antagonists, alpha2-adrenoreceptor antagonists, calcium antagonists, muscarinic receptor M1 agonists or partial agonists or positive modulators, muscarinic receptor M2 antagonists, muscarinic receptor M4 agonists or partial agonists or positive modulators, muscarinic receptor M4 antagonists, metabotropic glutamate-receptor 1 positive modulators, metabotropic glutamate-receptor 2 positive modulators, metabotropic glutamate-receptor 3 positive modulators, metabotropic glutamate-receptor 5 positive modulators, glycine transporter 1 inhibitors, antidepressants, such as citalopram, fluoxetine, paroxetine, sertraline and trazodone; anxiolytics, such as lorazepam and oxazepam; antipsychotics, such as aripiprazole, asenapine, clozapine, iloperidone, haloperidol, olanzapine, paliperidone, quetiapine, risperidone, ziprasidone, lurasidone, lumateperone, brexpiprazole and cariprazine; mood-stabilizers such as lithium and valproate, and other substances that modulate receptors or enzymes in a manner such that the efficacy and/or safety of the compounds according to the invention is increased and/or unwanted side effects are reduced. The compounds according to the invention may also be used in combination with immunotherapies (e.g., active immunisation with Abeta or Tau or parts thereof or passive immunisation with humanised anti-Abeta or anti-Tau antibodies or nanobodies) for the treatment of the above-mentioned diseases and conditions.

The dosage for the combination partners mentioned above is usefully 1/5 of the lowest dose normally recommended up to 1/1 of the normally recommended dose (e.g. 1/4, 1/3, or 1/2).

The use of the compound according to the invention in combination with another active substance may take place simultaneously or at staggered times, but particularly within a short space of time. If they are administered simultaneously, the two active substances are given to the patient together; while if they are used at staggered times the two active substances are given to the patient within a period of less than or equal to 12 hours (e.g. 1 hour, 2 hours, 3 hours, 4 hours, 5 hours, 6 hours, 7 hours, 8 hours, 8 hours, 9 hours, 10 hours, or 11 hours), but particularly less than or equal to 6 hours.

In another aspect, this invention relates to the use of a compound according to the invention or a pharmaceutically acceptable salt thereof combined with at least one of the active substances described above as a combination partner, for preparing a pharmaceutical composition which is suitable for the treatment and/or prevention of diseases or conditions which can be affected by agonists of GPR52. These are preferably pathologies related to insufficient GPR52 activity, particularly one of the diseases or conditions listed above.

In another aspect, this invention relates to a pharmaceutical composition which comprises a compound of general formula (I) according to the invention, or a pharmaceutically acceptable salt thereof, and at least one of the active substances described above as combination partners, optionally together with at least one inert adjuvant, diluent and/or carrier.

The compound of general formula (I) according to the invention and at least one of the active substances described above may both be present together in one formulation, for example a tablet or capsule, or separately in two identical or different formulations, for example as a so-called kit-of-parts.

EXPERIMENTAL SECTION

List of Abbreviations

Bn benzyl
tBu tert-butyl
RT room temperature
ESI-MS electrospray ionization mass spectrometry
CIP 2-chloro-4,5-dihydro-1,3-dimethyl-1H-imidazolium hexafluorophosphate
aq. aqueous
dppf 1,1'-bis(diphenylphosphanyl)ferrocene
MS mass spectrum
MeOH methanol
EtOH ethanol
EA ethyl acetate
DMA N,N-dimethylacetamide
4-DMAP 4-dimethylamino-pyridine
DMF N,N-dimethylformamide
DMSO dimethylsulfoxide
DCM dichloromethane
TCFH chloro-N,N,N',N'-tetramethylformamidinium hexafluorophosphate
THF tetrahydrofuran
DEAD diethyl azodicarboxylate
DIAD diisopropyl azodicarboxylate
DIPEA N,N-diisopropylethylamine
HATU 1-[bis(dimethylamino)methylene]-1H-1,2,3-triazolo[4,5-b]pyridinium 3-oxide hexafluorophosphate
HOBt 1-hydroxybenzotriazole
TBTU O-(benzotriazol-1-yl)-N,N,N',N'-tetramethyl-uronium tetrafluoroborate
Rt retention time
RT room temperature
d day(s)
RuPhos 2-dicyclohexylphosphino-2',6'-diisopropoxybiphenyl
h hour(s)
min minutes
sat. saturated
ACN acetonitrile
TFA trifluoroacetic acid
TBAF tetrabutyl ammonium fluoride
M molarity
MPLC medium-pressure liquid chromatography
N normality
n.d. not determined
$NH_3$ ammonia
NMP N-methylpyrrolidinone
HPLC high-performance liquid chromatography
HPLC-MS high-performance liquid chromatography-mass spectrometry
LC-MS liquid chromatography mass spectrometry
SFC supercritical fluid chromatography
TLC thin layer chromatography
TEA triethylamine
PPA propylphosphonic acid anhydride, cyclic trimer

HPLC-Methods

Mobile Phase Preparations:
The mobile phase "$H_2O$ 0.1% TFA" was prepared by adding 1 ml of a commercially available TFA solution to 999 ml water. The mobile phase "$H_2O$ 0.1% $NH_3$" was prepared by adding 4 ml of a commercially available concentrated ammonium hydroxide solution (25 wt %) to 996 ml water.

Method Name: A
Device description: Waters Acquity with DA- and MS-Detector
Column: XBridge, BEH C18, 2.1×30 mm, 2.5 μm
Column Supplier: Waters

| Gradient/Solvent Time [min] | % Sol [$H_2O$, 0.1% $NH_3$] | % Sol [ACN] | Flow [mL/min] | Temp [° C.] |
|---|---|---|---|---|
| 0.0 | 95.0 | 5.0 | 1.3 | 60.0 |
| 0.02 | 95.0 | 5.0 | 1.3 | 60.0 |
| 1.0 | 0.0 | 100.0 | 1.3 | 60.0 |
| 1.1 | 0.0 | 100.0 | 1.3 | 60.0 |

Method Name: B
Device description: Waters Acquity with DA- and MS-Detector
Column: XBridge, BEH C18, 2.1×30 mm, 2.5 μm
Column Supplier: Waters

| Gradient/Solvent Time [min] | % Sol [$H_2O$, 0.1% $NH_3$] | % Sol [ACN] | Flow [mL/min] | Temp [° C.] |
|---|---|---|---|---|
| 0.0 | 95.0 | 5.0 | 1.3 | 60.0 |
| 0.02 | 95.0 | 5.0 | 1.3 | 60.0 |
| 1.0 | 0.0 | 100.0 | 1.3 | 60.0 |
| 1.3 | 0.0 | 100.0 | 1.3 | 60.0 |

Method Name: C
Device description: Agilent 1200 with DA- and MS-Detector
Column: XBridge C18, 3.0×30 mm, 2.5 μm
Column Supplier: Waters

| Gradient/Solvent Time [min] | % Sol [$H_2O$ + 0.1% $NH_3$] | % Sol [ACN] | Flow [mL/min] | Temp [° C.] |
|---|---|---|---|---|
| 0.0 | 97 | 3 | 2.2 | 60 |
| 0.2 | 97 | 3 | 2.2 | 60 |
| 1.2 | 0 | 100 | 2.2 | 60 |
| 1.25 | 0 | 100 | 3.0 | 60 |
| 1.4 | 0 | 100 | 3.0 | 60 |

Method Name: D
Device description: Waters Acquity with DA- and MS-Detector
Column: Sunfire, C18, 3.0×30 mm, 2.5 μm
Column Supplier: Waters

| Gradient/Solvent Time [min] | % Sol [$H_2O$, 0.1% TFA] | % Sol [ACN] | Flow [mL/min] | Temp [° C.] |
|---|---|---|---|---|
| 0.0 | 95.0 | 5.0 | 1.5 | 60.0 |
| 1.3 | 0.0 | 100.0 | 1.5 | 60.0 |
| 1.5 | 0.0 | 100.0 | 1.5 | 60.0 |

Method Name: E
Device description: Agilent 1200 with DA- and MS-Detector
Column: Sunfire C18, 3.0×50 mm, 2.5 μm
Column Supplier: Waters

| Gradient/Solvent Time [min] | % Sol [$H_2O$, 0.1% TFA] | % Sol [ACN] | Flow [mL/min] | Temp [° C.] |
|---|---|---|---|---|
| 0.0 | 97 | 3 | 2.2 | 60 |
| 0.2 | 97 | 3 | 2.2 | 60 |

Method Name: F
Device description: Waters Acquity with DA- and MS-Detector
Column: XBridge BEH C18, 2.1×30 mm, 1.7 μm
Column Supplier: Waters

| Gradient/Solvent Time [min] | % Sol [H$_2$O, 0.1% TFA] | % Sol [ACN] | Flow [mL/min] | Temp [° C.] |
|---|---|---|---|---|
| 1.2 | 0 | 100 | 2.2 | 60 |
| 1.25 | 0 | 100 | 2.2 | 60 |
| 1.4 | 0 | 100 | 2.2 | 60 |

| Gradient/Solvent Time [min] | % Sol [H$_2$O, 0.1% TFA] | % Sol [ACN] | Flow [mL/min] | Temp [° C.] |
|---|---|---|---|---|
| 0.0 | 99 | 1 | 1.6 | 60 |
| 0.02 | 99 | 1 | 1.6 | 60 |
| 1.0 | 0 | 100 | 1.6 | 60 |
| 1.1 | 0 | 100 | 1.6 | 60 |

Method Name: G
Device description: Agilent 1260 SFC with DA- and MS-Detector, Back pressure 2175 psi
Column: CHIRAL ART® Cellulose SB, 4.6×250 mm, 5 μm
Column Supplier: YMC

| Gradient/Solvent Time [min] | % Sol [supercritical CO$_2$] | % Sol [MeOH, 20 mM NH$_3$] | Flow [mL/min] | Temp [° C.] |
|---|---|---|---|---|
| 0.0 | 75 | 25 | 4.0 | 40 |
| 10.0 | 75 | 25 | 4.0 | 40 |

Method Name: H
Device description: Agilent 1260 Infinity II SFC with DA-Detector, Back pressure 2175 psi
Column: Lux® Cellulose-4, 3×100 mm, 3 μm
Column Supplier: Phenomenex

| Gradient/Solvent Time [min] | % Sol [supercritical CO$_2$] | % Sol [MeOH, 20 mM NH$_3$] | Flow [mL/min] | Temp [° C.] |
|---|---|---|---|---|
| 0.0 | 80 | 20 | 2.0 | 40 |
| 4.0 | 80 | 20 | 2.0 | 40 |

Method Name: I
Device description: Agilent 1260 SFC with DA- and MS-Detector, Back pressure 2175 psi
Column: CHIRAL ART® Cellulose SB, 4.6×250 mm, 5 μm
Column Supplier: YMC

| Gradient/Solvent Time [min] | % Sol [supercritical CO$_2$] | % Sol [MeOH, 20 mM NH$_3$] | Flow [mL/min] | Temp [° C.] |
|---|---|---|---|---|
| 0.0 | 80 | 20 | 4.0 | 40 |
| 10.0 | 80 | 20 | 4.0 | 40 |

Method Name: J
Device description: Agilent 1260 Infinity II SFC with DA-Detector, Back pressure 2175 psi
Column: Lux® Cellulose-3, 3×100 mm, 3 μm
Column Supplier: Phenomenex

| Gradient/Solvent Time [min] | % Sol [supercritical CO$_2$] | % Sol [MeOH, 20 mM NH$_3$] | Flow [mL/min] | Temp [° C.] |
|---|---|---|---|---|
| 0.0 | 85 | 15 | 2.0 | 40 |
| 4.0 | 85 | 15 | 2.0 | 40 |

Method Name: K
Device description: Agilent 1260 Infinity II SFC with DA-Detector, Back pressure 2175 psi
Column: CHIRAL ART® Amylose-SA, 3×100 mm, 3 μm
Column Supplier: YMC

| Gradient/Solvent Time [min] | % Sol [supercritical CO$_2$] | % Sol [MeOH, 20 mM NH$_3$] | Flow [mL/min] | Temp [° C.] |
|---|---|---|---|---|
| 0.0 | 75 | 25 | 2.0 | 40 |
| 4.0 | 75 | 25 | 2.0 | 40 |

Method Name: L
Device description: Agilent 1260 Infinity II SFC with DA-Detector, Back pressure 2175 psi
Column: Lux® Cellulose-2, 4.6×250 mm, 5 μm
Column Supplier: Phenomenex

| Gradient/Solvent Time [min] | % Sol [supercritical CO$_2$] | % Sol [EtOH, 20 mM NH$_3$] | Flow [mL/min] | Temp [° C.] |
|---|---|---|---|---|
| 0.0 | 70 | 30 | 4.0 | 40 |
| 10.0 | 70 | 30 | 4.0 | 40 |

Method Name: M
Device description: Agilent 1260 Infinity II SFC with DA-Detector, Back pressure 2175 psi
Column: Lux® Cellulose-2, 3×100 mm, 3 μm
Column Supplier: Phenomenex

| Gradient/Solvent Time [min] | % Sol [supercritical CO$_2$] | % Sol [MeOH, 20 mM NH$_3$] | Flow [mL/min] | Temp [° C.] |
|---|---|---|---|---|
| 0.0 | 65 | 35 | 2.0 | 40 |
| 4.0 | 65 | 35 | 2.0 | 40 |

General Comment Concerning the Presentation of the Structures:

Compounds with stereogenic centre(s): the structures depicted in the experimental section will not necessarily show all the stereochemical possibilities of the compounds.

The structural presentation of the compounds in the experimental section will show a stereochemical bond only in case where the absolute stereochemistry is known.

The structural presentation of the compounds in the experimental section with unknown absolute stereochemistry will show a planar bond plus an additional comment that indicates if the described compound is a racemic mixture, a single stereoisomer and where applicable the relative stereochemistry.

Two examples are given below.

Example I: the presented chemical structure is depicted as follow

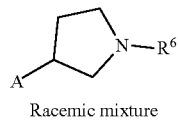

Racemic mixture

The added term 'racemic mixture' (in the FIGURE or in the experiment description) points to the two stereochemical options and thus the manufactured compound is a mixture of:

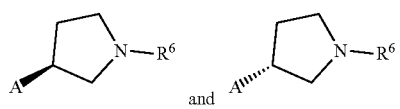

and

When racemic mixtures of above depicted structures are separated, the single stereoisomers are depicted accordingly to the absolute stereochemistry if it is known; alternatively, the single stereoisomers are depicted as:

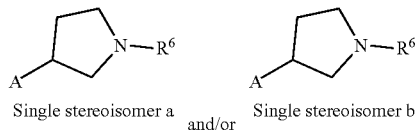

Single stereoisomer a and/or Single stereoisomer b

The added term 'single stereoisomer' and the planar bond indicates that the absolute configuration is unknown. The term 'single stereoisomer a' is assigned to the first eluting isomer in chiral HPLC, and 'single stereoisomer b' is assigned to the second eluting isomer in chiral HPLC.

Example II: the presented chemical structure is depicted as follow

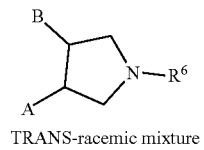

TRANS-racemic mixture

The added term 'TRANS-racemic mixture' (in the FIGURE or in the experiment description) points to the two stereochemical options and thus the manufactured compounds is a mixture of:

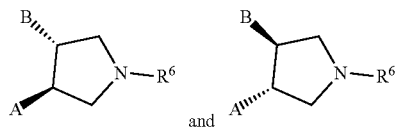

and

When racemic mixtures of above depicted structures are separated, the single stereoisomers are depicted as:

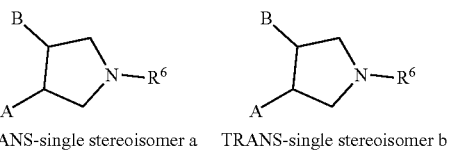

TRANS-single stereoisomer a    TRANS-single stereoisomer b

The added term 'TRANS-single stereoisomer' indicates a relative configuration known (trans) and the planar bond indicates the unknown absolute configuration. 'TRANS-single stereoisomer a' is assigned to the first eluting isomer in chiral HPLC, and 'TRANS-single stereoisomer b' is assigned to the second eluting isomer in chiral HPLC.

The same principles apply to the terms 'CIS-racemic mixture', 'CIS-single stereoisomer a' and 'CIS-single stereoisomer b'.

The absolute configuration of Example 8a, 8b, 10a, 10b, 11a, 11b, 13a, 13b, 15a and 15b was assigned by asymmetric synthesis of Example 8b, 10a, 11b, 13b and 15a starting from an optically pure precursor and following comparison via chiral chromatography for each couple of enantiomers between the single enantiomer obtained by the above-mentioned asymmetric synthesis and the two single enantiomers obtained by separation via chiral chromatography of the racemate thereof (see experimental section).

It will be understood from those skilled in the art that the absolute configuration of a compound of the present invention may be determined or further confirmed by X-ray crystallography, for example by single crystal X-ray diffraction of their crystalline products or their crystalline intermediates which are derivatized if necessary.

PREPARATION OF INTERMEDIATES AND EXAMPLES

The following examples and intermediates are intended to illustrate the invention, without restricting its scope.

Intermediate A-1

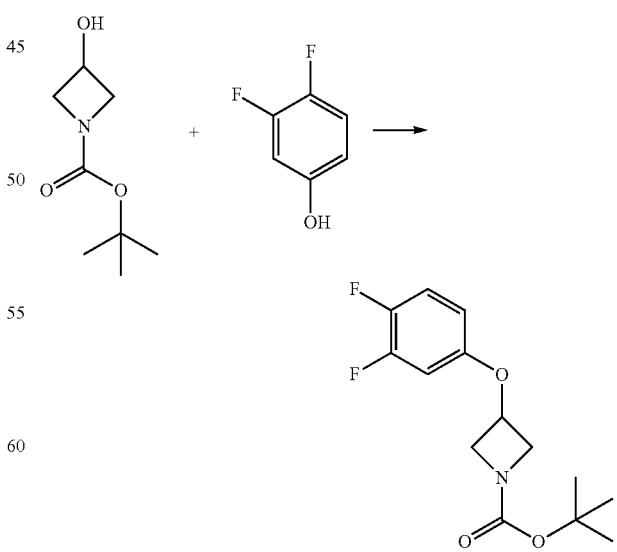

A-1

A mixture of 3,4-difluoro-phenol (10.0 g, 76.9 mmol) and cesium carbonate (37.6 g, 115.3 mmol) in DMA (558 mL) was stirred for 5 min at RT, then tert-butyl-3-methanesulfonyloxy)azetidine-1-carboxylate (19.3 g, 76.9 mmol) was added. After stirring at 100° C. for 5 h the mixture was cooled to RT and concentrated under reduced pressure. Water and ethyl acetate were added. Phases were separated. The aqueous phase was extracted 3× with ethyl acetate. The combined organic phases were dried over Na$_2$SO$_4$ and concentrated under reduced pressure. The remainder was purified by MPLC (silica gel, petrol ether/ethyl acetate 9:1) to provide the product A-1.

ESI-MS: 286 [M+H]$^+$; HPLC (Rt): 0.72 min (method A)

Intermediate A-2

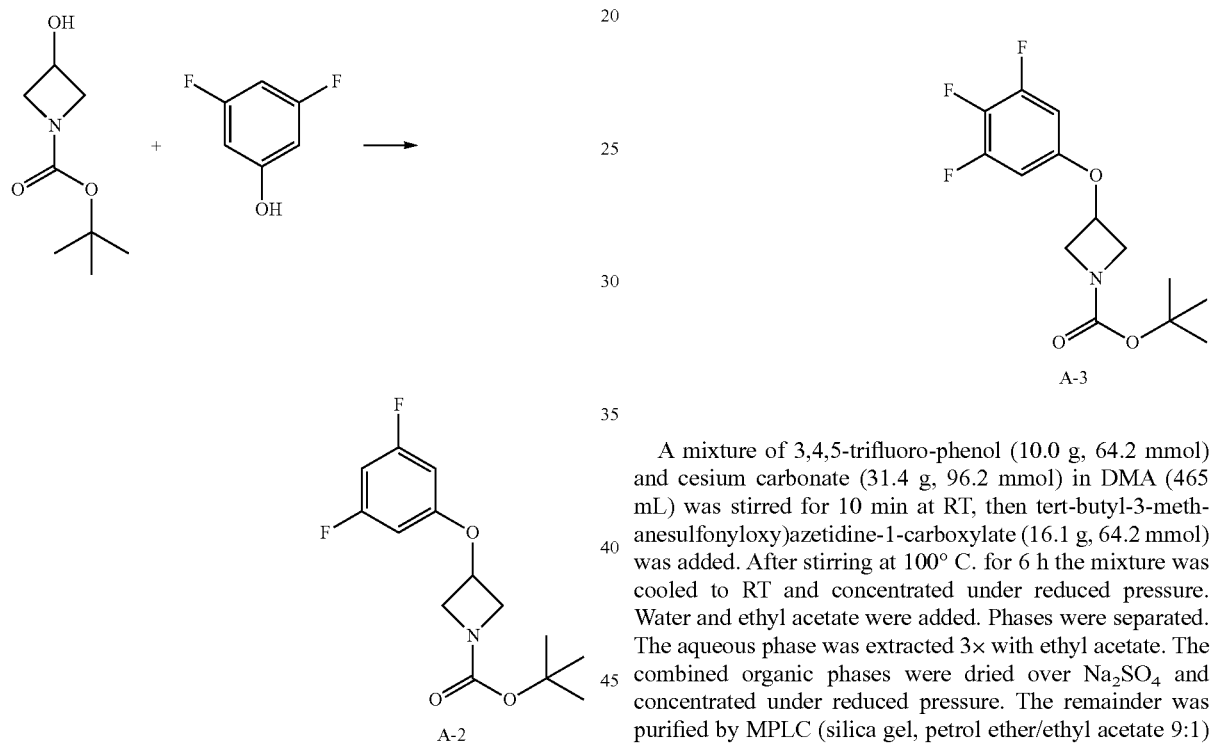

A-2

A mixture of 3,5-difluoro-phenol (1.0 g, 8.0 mmol) and cesium carbonate (5.2 g, 15.9 mmol) in DMA (5 mL) was stirred for 10 min at RT, then tert-butyl-3-methanesulfonyloxy)azetidine-1-carboxylate (2.0 g, 8.0 mmol) was added. After stirring at 90° C. for 16 h the mixture was cooled to RT and water and ethyl acetate were added. Phases were separated. The combined organic phases were washed with brine, dried over Na$_2$SO$_4$ and concentrated under reduced pressure. The remainder was purified by preparative HPLC to provide the product A-2.

ESI-MS: 286 [M+H]$^+$; HPLC (Rt): 1.02 min (method D)

Intermediate A-3

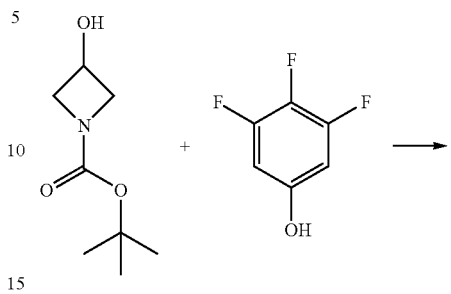

A-3

A mixture of 3,4,5-trifluoro-phenol (10.0 g, 64.2 mmol) and cesium carbonate (31.4 g, 96.2 mmol) in DMA (465 mL) was stirred for 10 min at RT, then tert-butyl-3-methanesulfonyloxy)azetidine-1-carboxylate (16.1 g, 64.2 mmol) was added. After stirring at 100° C. for 6 h the mixture was cooled to RT and concentrated under reduced pressure. Water and ethyl acetate were added. Phases were separated. The aqueous phase was extracted 3× with ethyl acetate. The combined organic phases were dried over Na$_2$SO$_4$ and concentrated under reduced pressure. The remainder was purified by MPLC (silica gel, petrol ether/ethyl acetate 9:1) to provide the product A-3.

ESI-MS: 304 [M+H]$^+$; HPLC (Rt): 0.75 min (method A)

Intermediate A-4

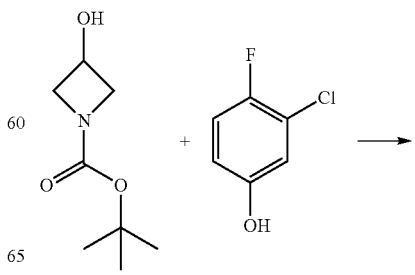

-continued

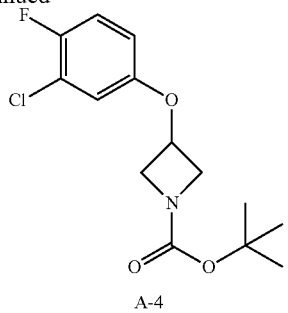

A-4

A mixture of 3-chloro-4-fluoro-phenol (1.5 g, 10.2 mmol) and cesium carbonate (6.7 g, 20.5 mmol) in DMA (10 mL) was stirred for 10 min at RT, then tert-butyl-3-methanesulfonyloxy)azetidine-1-carboxylate (2.6 g, 10.2 mmol) was added. After stirring at 100° C. for 16 h the mixture was cooled to RT. Water and DCM were added. Phases were separated. The organic phase was dried over $Na_2SO_4$ and concentrated under reduced pressure. The remainder was purified by preparative HPLC to provide the product A-4.

ESI-MS: 302/304 [M+H]$^+$; HPLC (Rt): 0.78 min (method A)

Intermediate A-5

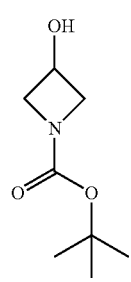 + 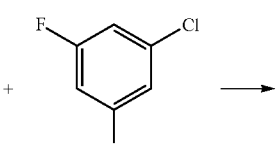 →

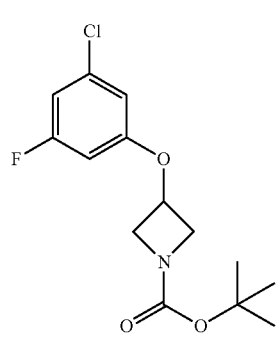

A-5

A mixture of 3-chloro-5-fluoro-phenol (4.8 g, 33.0 mmol) and cesium carbonate (21.5 g, 66.1 mmol) in DMF (20 mL) was stirred for 10 min at RT, then tert-butyl-3-methanesulfonyloxy)azetidine-1-carboxylate (2.5 g, 10.1 mmol) was added. After stirring at 90° C. for 16 h the mixture was cooled to RT and water and ethyl acetate were added. Phases were separated and the aqueous phase was extracted 3× with ethyl acetate. The combined organic phases were dried over $Na_2SO_4$ and concentrated under reduced pressure. The remainder was purified by preparative HPLC to provide the product A-5.

ESI-MS: 302/304 [M+H]$^+$; HPLC (Rt): 0.77 min (method A)

Intermediate A-6

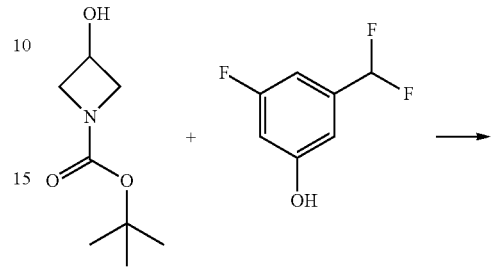 →

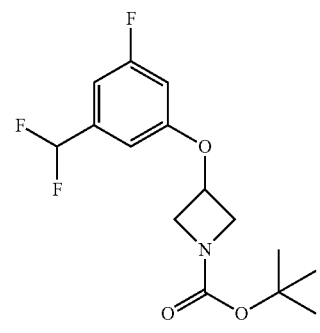

A-6

A mixture of 3-fluoro-5-(difluoromethyl)-phenol (2.5 g, 10.0 mmol) and cesium carbonate (6.5 g, 20.0 mmol) in DMA (10 mL) was stirred for 10 min at RT, then tert-butyl-3-methanesulfonyloxy)azetidine-1-carboxylate (2.5 g, 10.0 mmol) was added. After stirring at 90° C. for 16 h the mixture was cooled to RT and water and ethyl acetate were added. Phases were separated. The aqueous phase was extracted 3× with ethyl acetate. The combined organic phases were washed with brine, dried over $Na_2SO_4$ and concentrated under reduced pressure. The remainder was purified by preparative HPLC to provide the product A-6.

ESI-MS: 318 [M+H]$^+$, 262 [M+H-isobuten]$^+$; HPLC (Rt): 1.03 min (method D)

Intermediate A-7

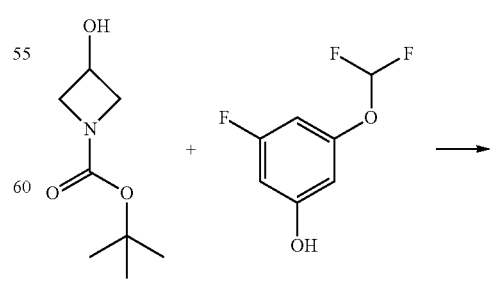 →

-continued

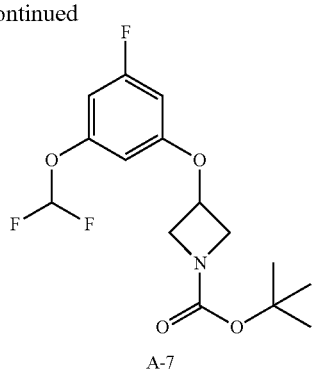

A-7

A mixture of 3-(difluoromethoxy)-5-fluoro-phenol (0.4 g, 2.2 mmol) and cesium carbonate (1.4 g, 4.4 mmol) in DMA (2.5 mL) was stirred for 10 min at RT, then tert-butyl-3-methanesulfonyloxy)azetidine-1-carboxylate (0.6 g, 2.2 mmol) was added. After stirring at 90° C. for 16 h the mixture was cooled to RT and water and ethyl acetate were added. Phases were separated. The aqueous phase was extracted 3× with ethyl acetate. The combined organic phases were washed with brine, dried over $Na_2SO_4$ and concentrated under reduced pressure. The remainder was purified by preparative HPLC to provide the product A-7.

ESI-MS: 334 $[M+H]^+$, 278 $[M+H-isobuten]^+$; HPLC (Rt): 1.05 min (method D)

Intermediate B-1

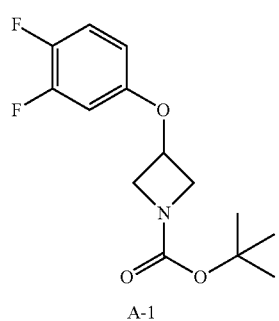

A-1

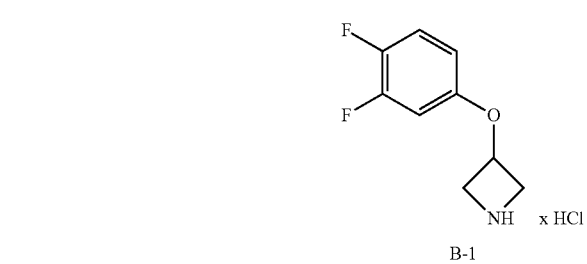

B-1

To a mixture of intermediate A-1 (19.0 g, 66.6 mmol) in diisopropyl ether (200 mL) was added a solution of HCl in dioxane (4N, 83.3 mL, 333.0 mmol). After stirring for 16 h at RT the mixture was concentrated under reduced pressure. The precipitate was washed with diethyl ether and dried to give product B-1 as HCl salt.

ESI-MS: 186 $[M+H]^+$; HPLC (Rt): 0.38 min (method A)

Intermediate B-2

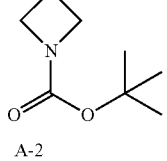

A-2

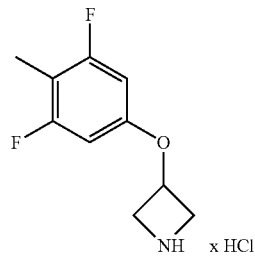

B-2

To intermediate A-2 (1.85 g, 6.49 mmol) was added a solution of HCl in dioxane (4N, 15.0 mL, 60.0 mmol). After stirring for 1 h at RT the mixture was concentrated under reduced pressure to give product B-2 as HCl salt.

ESI-MS: 186 $[M+H]^+$; HPLC (Rt): 0.38 min (method D)

Intermediate B-3

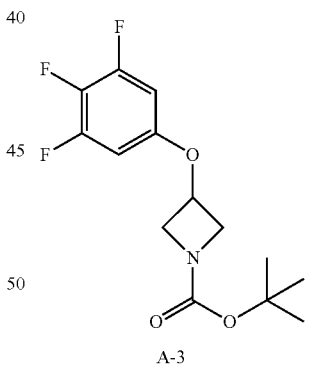

A-3

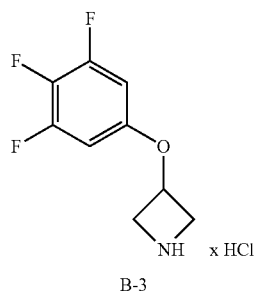

B-3

To intermediate A-3 (3.24 g, 10.68 mmol) was added a solution of HCl in dioxane (4N, 25.0 mL, 100.0 mmol).

After stirring for 1 h at RT the mixture was concentrated under reduced pressure to give product B-3 as HCl salt.

ESI-MS: 204 [M+H]$^+$; HPLC (Rt): 0.45 min (method A)

Intermediate B-4

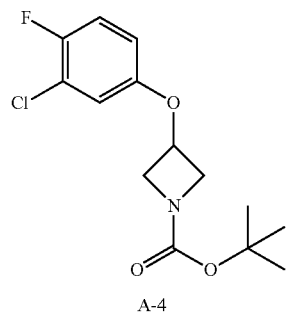

A-4

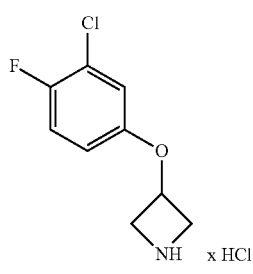

B-4

To intermediate A-4 (2.3 g, 7.6 mmol) was added a solution of HCl in dioxane (4N, 9.5 mL, 37.9 mmol). After stirring for 45 min at RT the mixture was concentrated under reduced pressure to give product B-4 as HCl salt.

ESI-MS: 202/204 [M+H]$^+$; HPLC (Rt): 0.51 min (method B)

Intermediate B-5

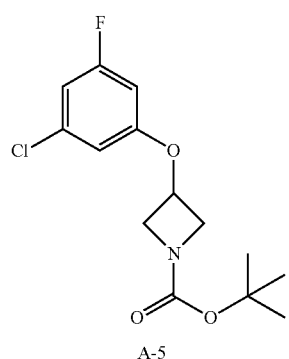

A-5

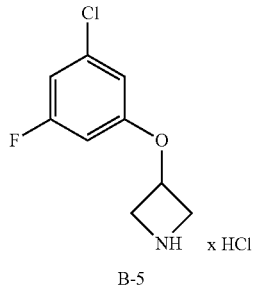

B-5

To intermediate A-5 (8.3 g, 27.5 mmol) was added a solution of HCl in dioxane (4N, 34.4 mL, 137.5 mmol). After stirring for 1 h at RT the mixture was concentrated under reduced pressure to give product B-5 as HCl salt.

ESI-MS: 202/204 [M+H]$^+$; HPLC (Rt): 0.52 min (method A)

Intermediate B-6

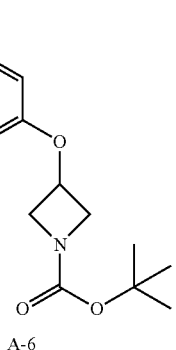

A-6

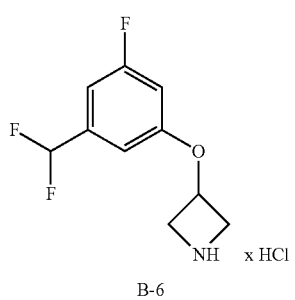

B-6

To intermediate A-6 (2.6 g, 8.0 mmol) was added a solution of HCl in dioxane (4N, 12.1 mL, 48.2 mmol). After stirring for 1 h at RT the mixture was concentrated under reduced pressure to give product B-6 as HCl salt.

ESI-MS: 218 [M+H]$^+$; HPLC (Rt): 0.45 min (method D)

Intermediate B-7

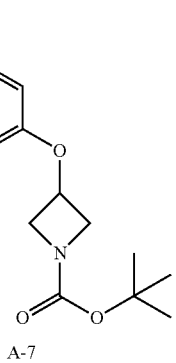

A-7

-continued

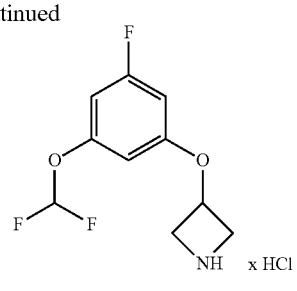

B-7

To intermediate A-7 (625.0 mg, 1.9 mmol) was added a solution of HCl in dioxane (4N, 5.0 mL, 20.0 mmol). After stirring for 1 h at RT the mixture was concentrated under reduced pressure to give product B-7 as HCl salt.

ESI-MS: 234 [M+H]$^+$; HPLC (Rt): 0.45 min (method D)

Intermediate C-1.1

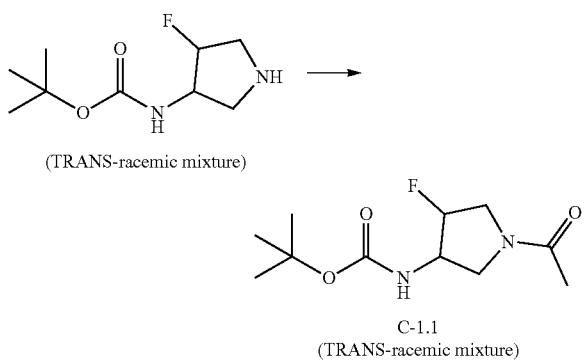

To a mixture of trans-(3-tert.-butyloxycarbonyl-amino)-4-fluoropyrrolidine (500.0 mg, 244.8 μmol and DIPEA (2.12 mL, 12.24 mmol) in acetonitrile (2 mL) was added acetyl chloride (261.1 μL, 367.2 μmol. After stirring at RT for 10 min the reaction mixture was concentrated under reduced pressure and the remainder was purified by preparative HPLC to give intermediate C-1.1 as TRANS-racemic mixture.

ESI-MS: 247 [M+H]$^+$; HPLC (Rt): 0.44 min (method B)

Intermediate C-1

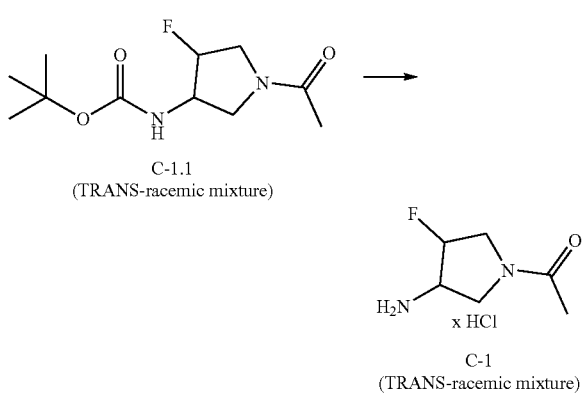

To a mixture of intermediate C-1.1 (550.0 mg, 223.3 μmol, TRANS-racemic mixture) in 1,4-dioxane (2.2 mL) was added a solution of hydrochloric acid (4N in 1,4-dioxane, 4.47 mL, 17.87 mmol). After stirring at RT for 16h the reaction mixture was diluted with diethyl ether. The precipitate was collected by filtration, washed with diethyl ether, dissolved in acetonitrile/water mixture and lyophilized to give intermediate C-1 as HCl salt as TRANS-racemic mixture.

ESI-MS: 147 [M+H]$^+$; HPLC (Rt): 0.13 min (method B)

Intermediate C-2.1

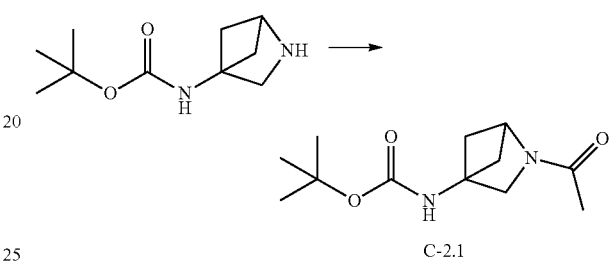

C-2.1

To a mixture of tert.-butyl N-(2-azabicyclo[2.1.1]hexan-4-yl)carbamate (200.0 mg, 1.0 mmol) and DIPEA (0.87 mL, 5.04 mmol) in a mixture of acetonitrile (1.6 mL) and DMF (0.8 mL) was added acetyl chloride (107.59 μL, 1.51 mmol). After stirring at RT for 15 min the reaction mixture, saturated aqueous NaHCO3 solution was added, and the mixture was extracted with ethyl acetate. The aqueous phase was extracted with ethyl acetate. The combined organic phases were washed with brine solution, dried over sodium sulfate and concentrated under reduced pressure to give intermediate C-2.1.

ESI-MS: 241 [M+H]$^+$; HPLC (Rt): 0.54 min (method D)

Intermediate C-2

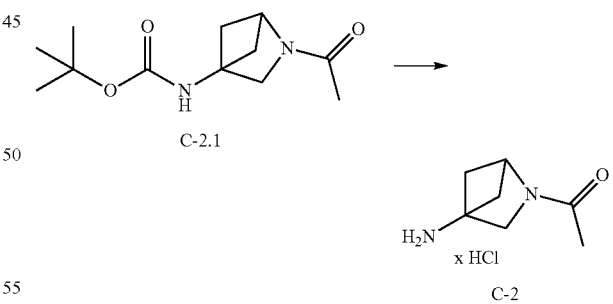

C-2

To intermediate C-2.1 (211.4 mg, 880.0 μmol was added a solution of hydrochloric acid (4N in 1,4-dioxane, 0.88 mL, 3.52 mmol) and a few drops of methanol. After stirring at RT for 1.5 h additional 0.45 mL of the hydrochloric acid solution (4N in 1,4-dioxane, 0.45 mL, 1.80 mmol) was added and stirring was continued for 30 min. The reaction mixture was concentrated under reduced pressure. The remainder was triturated with diethyl ether and dried to give intermediate C-2 as HCl salt.

ESI-MS: 141 [M+H]$^+$; HPLC (Rt): 0.12 min (method D)

Intermediate D-1

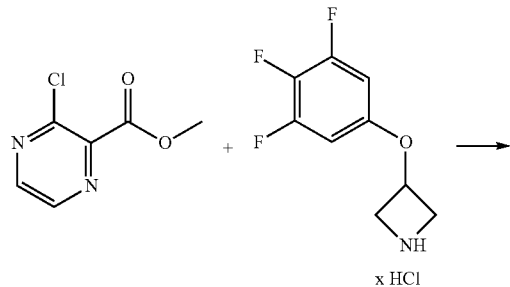

B-3

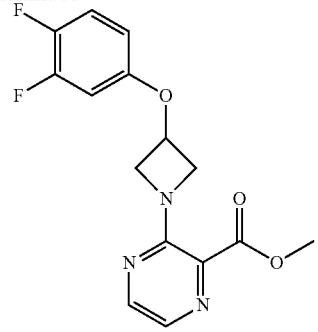

D-2

A mixture of methyl 3-chloropyrazine-2-carboxylate (1.0 g, 5.8 mmol), intermediate B-1 (HCl salt, 1.5 g, 7.0 mmol) and TEA (1.95 mL, 13.91 mmol) in DMA (10 mL) was stirred for 1 h at RT. The reaction mixture was diluted with water. The precipitate was collected by suction filtration and dried at 50° C. to give intermediate D-2.

ESI-MS: 322 [M+H]$^+$; HPLC (Rt): 0.60 min (method A)

Intermediate D-3

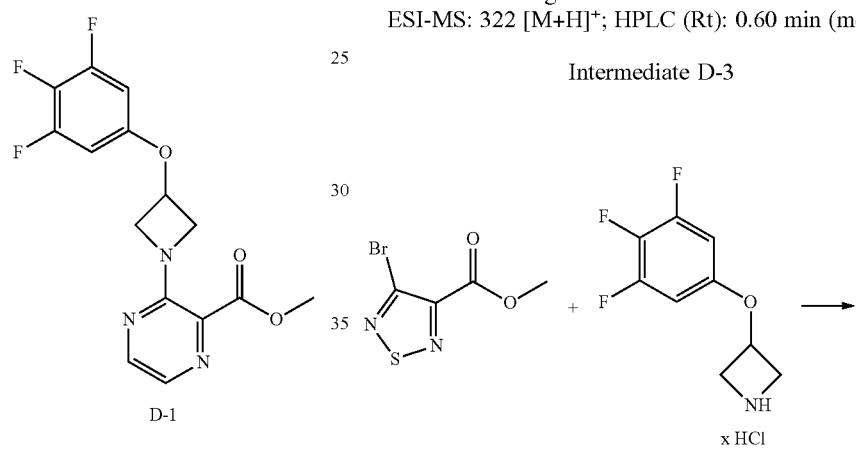

D-1

A mixture of methyl 3-chloropyrazine-2-carboxylate (1.5 g, 8.7 mmol), intermediate B-3 (HCl salt, 2.5 g, 10.4 mmol) and TEA (2.93 mL, 20.86 mmol) in DMF (9.2 mL) was stirred for 1 h at RT. The reaction mixture was diluted with water. The precipitate was collected by suction filtration and dried at 50° C. to give intermediate D-1.

ESI-MS: 340 [M+H]$^+$; HPLC (Rt): 0.63 min (method A)

Intermediate D-2

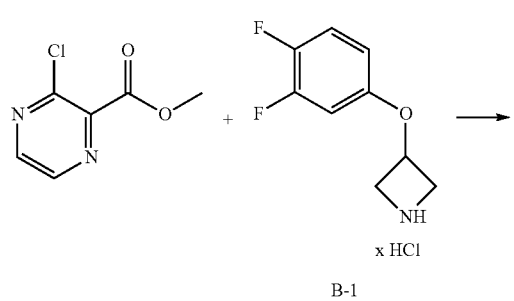

B-1

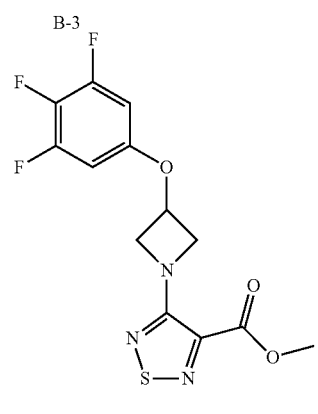

D-3

A mixture of methyl 4-bromo-1,2,5-thiadiazole-3-carboxylate (300.0 mg, 1.3 mmol), intermediate B-3 (HCl salt, 322.3 mg, 1.3 mmol), cesium carbonate (525.9 mg, 1.6 mmol) and sodium iodide (302.4 mg, 2.0 mmol) in DMF (8 mL) was stirred for 2.5 h at 80° C. After cooling to RT the reaction mixture was diluted with water. The mixture was extracted with ethyl acetate. The combined organic phases were washed with water and with brine, then were dried over sodium sulfate and concentrated under reduced pressure.

The remainder was purified by preparative MPLC (gradient petrol ether/ethyl acetate 95:5 to 65:35) to give intermediate D-3.

ESI-MS: 346 [M+H]$^+$; HPLC (Rt): 1.11 min (method C)

Intermediate D-4

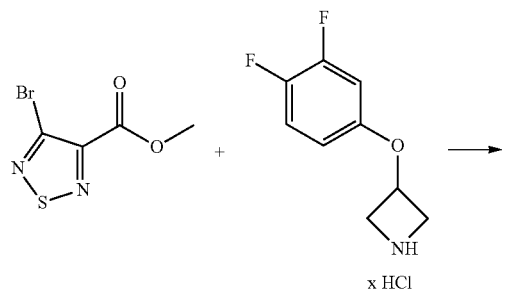

B-1

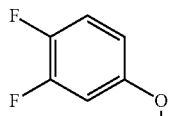

D-4

A mixture of methyl 4-bromo-1,2,5-thiadiazole-3-carboxylate (2.0 g, 9.0 mmol), intermediate B-1 (HCl salt, 2.0 g, 9.0 mmol), cesium carbonate (3.5 g, 10.8 mmol) and sodium iodide (2.0 g, 13.5 mmol) in DMF (45 mL) was stirred for 1.5 h at 80° C. After cooling to RT the reaction mixture was diluted with water. The precipitate was filtered off and dried under reduced pressure to give crude intermediate D-4.

ESI-MS: 328 [M+H]$^+$; HPLC (Rt): 1.01 min (method D)

Intermediate D-5

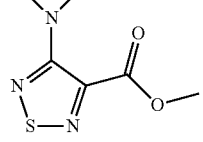

B-2

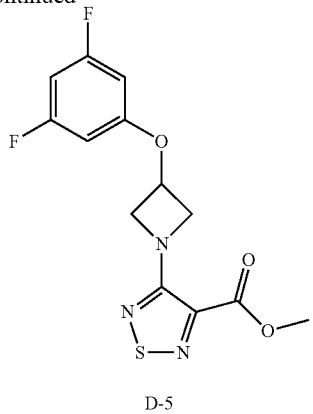

D-5

A mixture of methyl 4-bromo-1,2,5-thiadiazole-3-carboxylate (2.0 g, 9.0 mmol), intermediate B-2 (HCl salt, 2.0 g, 9.0 mmol), cesium carbonate (3.5 g, 10.8 mmol) and sodium iodide (2.0 g, 13.5 mmol) in DMF (45 mL) was stirred for 1.5 h at 80° C. After cooling to RT the reaction mixture was diluted with water. The precipitate was filtered off and dried under reduced pressure to give crude intermediate D-5.

ESI-MS: 328 [M+H]$^+$; HPLC (Rt): 1.00 min (method D)

Intermediate E-1

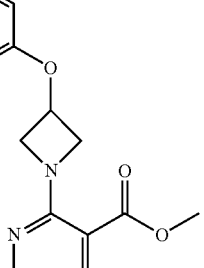

D-1

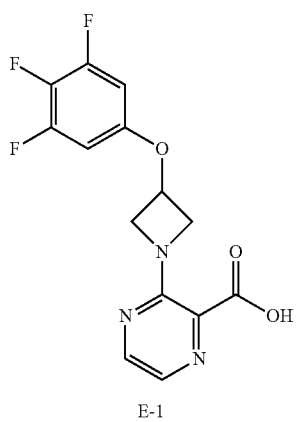

E-1

To a mixture of intermediate D-1 (4.15 g, 12.23 mmol) in acetone (40 mL) was added an aq. solution of lithium hydroxide (585.9 mg, 24.5 mmol, in 40 mL water). The reaction mixture was stirred for 2 h, then diluted with water and was acidified with hydrochloric acid (4N) to pH 4. The precipitate was collected by suction filtration and dried at 50° C. to give intermediate E-1.

ESI-MS: 326 [M+H]⁺; HPLC (Rt): 0.31 min (method A)

Intermediate E-2

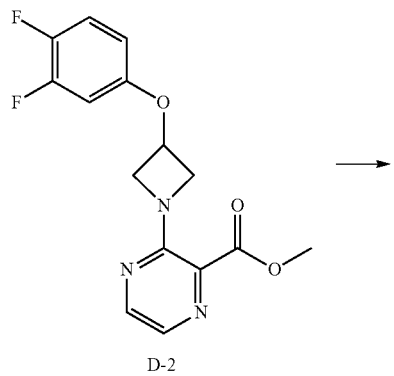

To a mixture of intermediate D-2 (1.6 g, 4.9 mmol) in acetone (15 mL) was added an aq. solution of lithium hydroxide (230.0 mg, 9.8 mmol, in 15 mL water). The reaction mixture was stirred for 1.5 h at RT, then diluted with water and was acidified with hydrochloric acid (4N) to pH 4. The precipitate was collected by suction filtration and dried at 50° C. to give intermediate E-2.

ESI-MS: 308 [M+H]⁺; HPLC (Rt): 0.27 min (method A)

Intermediate E-3

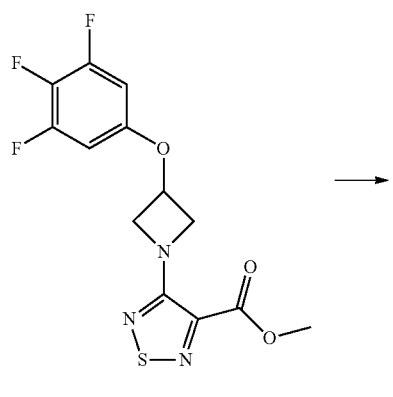

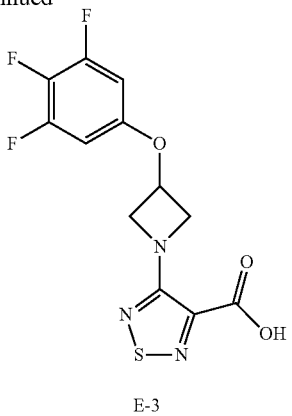

To a mixture of intermediate D-3 (438.0 mg, 1.3 mmol) in THF (10 mL) was added a solution of lithium hydroxide (135.0 mg, 5.6 mmol) in water (5 mL). The mixture was stirred for 2 h at RT, then was acidified with 4N hydrochloric acid. The mixture was extracted with ethyl acetate and the organic phase was washed with brine, dried over sodium sulfate and concentrated under reduced pressure to give crude intermediate E-3.

ESI-MS: 332 [M+H]⁺; HPLC (Rt): 1.03 min (method E)

Intermediate E-4

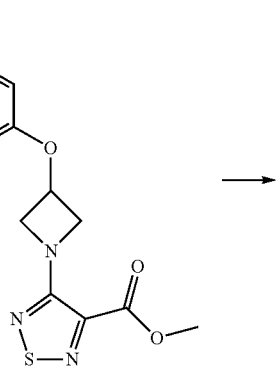

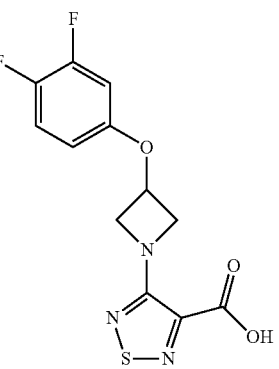

To a mixture of intermediate D-4 (2.2 g, 6.7 mmol) in THF (60 mL) and water (35 mL) was added lithium hydroxide (858.9 mg, 35.9 mmol). The mixture was stirred for 16 h at RT, then concentrated under reduced pressure to remove THF. The aqueous remainder was acidified with 4N hydrochloric acid. Precipitate was formed, collected by filtration and dried under reduced pressure at 40° C. to give crude intermediate E-4.

ESI-MS: 314 [M+H]$^+$; HPLC (Rt): 0.85 min (method D)

Intermediate E-5

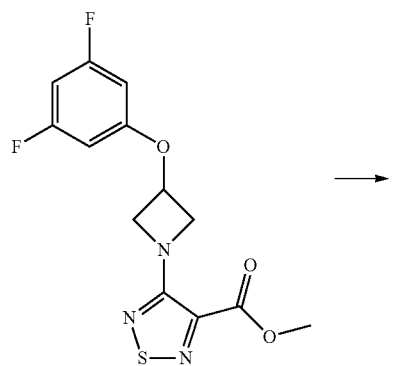

D-5

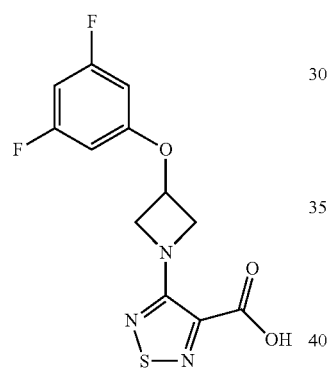

E-5

To a mixture of intermediate D-5 (2.3 g, 6.9 mmol) in THF (60 mL) and water (35 mL) was added lithium hydroxide (858.9 mg, 35.9 mmol). The mixture was stirred for 16 h at RT, then concentrated under reduced pressure to remove THF. The aqueous remainder was acidified with 4N hydrochloric acid. Precipitate was formed, collected by filtration and dried under reduced pressure at 40° C. to give crude intermediate E-5.

ESI-MS: 314 [M+H]$^+$; HPLC (Rt): 0.84 min (method D)

Intermediate F-1.1

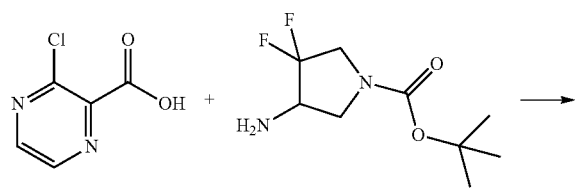

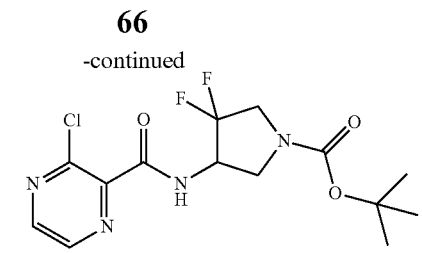

F-1.1

To a mixture of 3-chloropyrazine-2-carboxylic acid (380.0 mg, 2.4 mmol), tert-butyl-4-amino-3,3-difluoropyrrolidine-1-carboxylate (532.7 mg, 2.4 mmol) and 1-methylimidazole (386.0 μL, 4.8 mmol) in acetonitrile (3 mL) was added TCFH (739.8 mg, 2.6 mmol). The mixture was stirred for 15 min at RT. The mixture was concentrated to half its volume and was purified directly by preparative HPLC to give intermediate F-1.1 as racemic mixture.

ESI-MS: 307/309 [M+H-tert-butyl]$^+$; HPLC (Rt): 0.81 min (method D)

Intermediate (S)-F-1.1

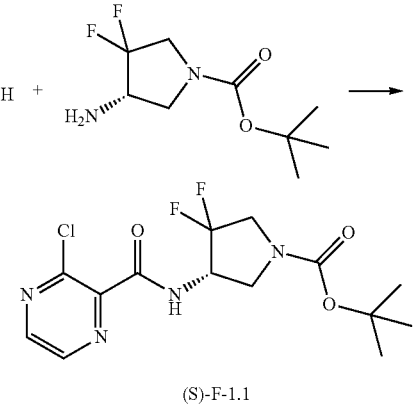

(S)-F-1.1

To a mixture of 3-chloropyrazine-2-carboxylic acid (300.0 mg, 1.9 mmol), (S)-tert-butyl-4-amino-3,3-difluoropyrrolidine-1-carboxylate (CAS-No. 2381400-91-3, 420.5 mg, 1.9 mmol) and 1-methylimidazole (304.7 μL, 3.8 mmol) in acetonitrile (5 mL) was added TCFH (584.0 mg, 2.1 mmol). After stirring for 3 d at RT, water and aqueous ammonia solution were added. The mixture was filtered and purified directly by preparative HPLC to give intermediate (S)-F-1.1.

ESI-MS: 307/309 [M+H-tert-butyl]$^+$; HPLC (Rt): 0.80 min (method D)

Intermediate F-1.2

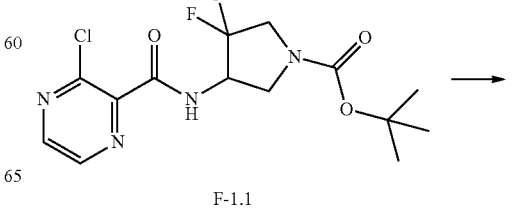

F-1.1

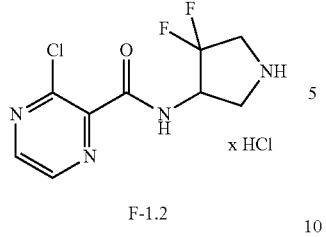

F-1.2

To a mixture of intermediate F-1.1 (736.0 mg, 2.0 mmol) in 1,4-dioxane (2.9 mL) was added hydrochloric acid (4N in 1,4-dioxane, 8.0 mL, 32.0 mmol). After stirring for 16 h at RT the mixture was diluted with diethyl ether. The precipitate was collected by filtration, washed with diethyl ether and dried to provide intermediate F-1.2 as racemic mixture.

ESI-MS: 263/265 [M+H]⁺; HPLC (Rt): 0.28 min (method D)

Intermediate (S)-F-1.2

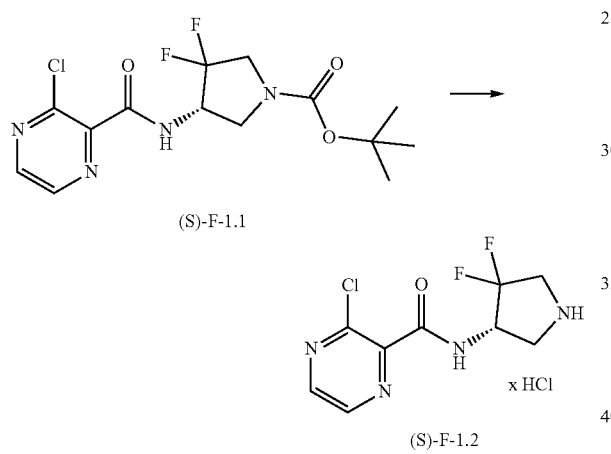

To a mixture of intermediate (S)-F-1.1 (570.0 mg, 1.6 mmol) in 1,4-dioxane (1.5 mL) was added hydrochloric acid (4N in 1,4-dioxane, 1.6 mL, 6.3 mmol). After stirring for 16 h at RT, methanol (3 mL) was added and stirring was continued for 2 h at RT. The mixture was concentrated under reduced pressure, and the remainder was triturated with tert.-butyl methyl ether, collected by filtration and and dried to provide intermediate (S)-F-1.2.

ESI-MS: 263/265 [M+H]⁺; HPLC (Rt): 0.28 min (method D)

Intermediate F-1

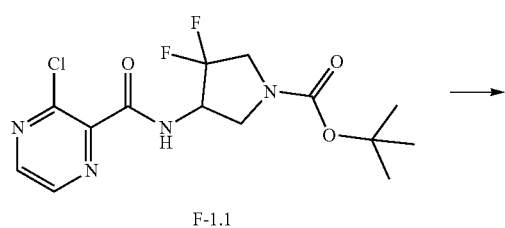

F-1.1

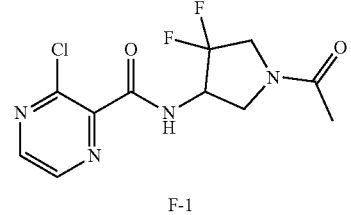

F-1

To a mixture of intermediate F-1.1 (1.3 g, 3.6 mmol) and methanol (287.3 µL, 7.2 mmol) in dichloromethane (30 mL) was dropwise added a solution of acetyl bromide (1.06 mL, 14.34 mmol) in dichloromethane (7 mL) at RT. After stirring for 30 min, the reaction mixture was cooled to 0-5° C. A solution of triethylamine (1.51 mL, 10.75 mmol) in dichloromethane (5 mL) was added dropwise. After stirring for 5 min the reaction mixture was concentrated under reduced pressure. The remainder was taken up in a mixture of water/methanol (v/v 5/5 mL), then acidified with TFA and purified by preparative HPLC to give intermediate F-1 as racemic mixture.

ESI-MS: 305/307 [M+H]⁺; HPLC (Rt): 0.43 min (method D)

Intermediate (S)-F-1

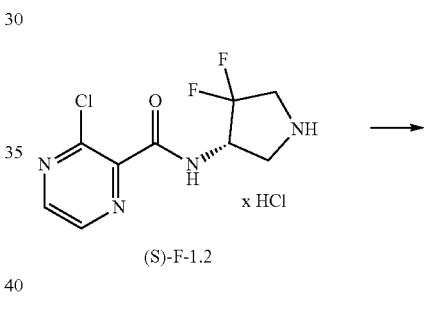

(S)-F-1.2

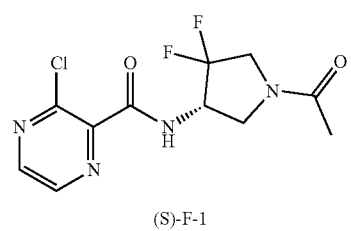

(S)-F-1

To a mixture of intermediate (S)-F-1.2 (455.0 mg, 1.5 mmol) and triethylamine (640.7 µL, 4.6 mmol) in acetonitrile (4 mL) was added acetyl chloride (162.2 µL, 2.3 mmol). After stirring for 16 h at RT, water was added. The mixture was filtered and purified directly by preparative HPLC to give intermediate (S)-F-1.

ESI-MS: 305/307 [M+H]⁺; HPLC (Rt): 0.44 min (method D)

Intermediate F-2

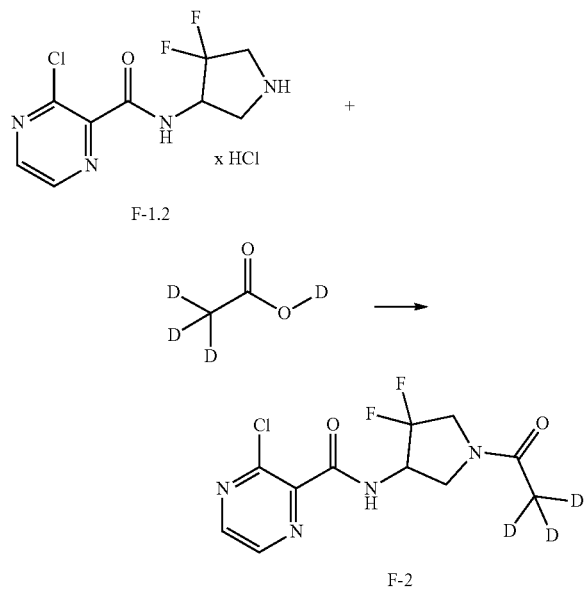

To a mixture of intermediate F-1.2 (50.0 mg, 167.0 µmol, D4-acetic acid (10.5 µL, 184.0 µmol, HATU (66.7 mg, 176.0 µmol in DMF (2 mL) was added DIPEA (57.5 µL, 334.0 µmol at RT. After stirring for 1 h at RT the reaction mixture was purified directly by preparative HPLC to give intermediate F-2 as racemic mixture.

ESI-MS: 308/310 [M+H]⁺; HPLC (Rt): 0.28 min (method B)

Intermediate G-1

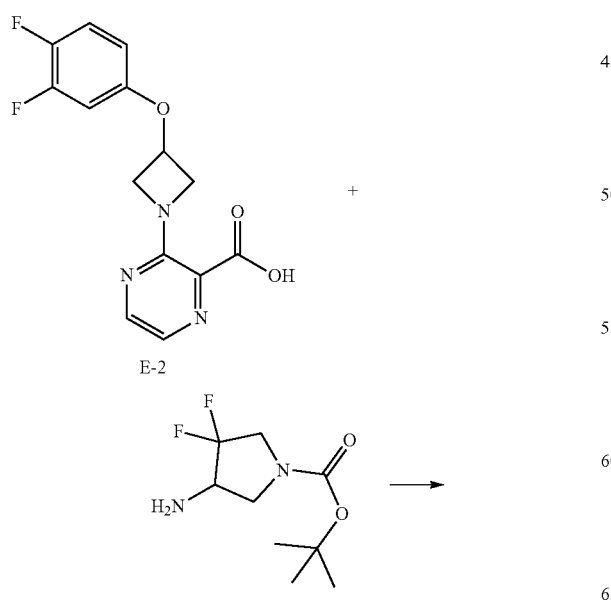

To a mixture of intermediate E-2 (300.0 mg, 976.0 µmol, tert-butyl-4-amino-3,3-difluoropyrrolidine-1-carboxylate (227.8 mg, 1.0 mmol) and DIPEA (663.9 µL, 3.9 mmol) in acetonitrile (5 mL) was added CIP (299.2 mg, 1.1 mmol). After stirring for 16 h at RT, the reaction mixture was diluted with water. The organic phase was separated and purified directly by preparative HPLC to provide intermediate G-1 as racemic mixture.

ESI-MS: 512 [M+H]⁺; HPLC (Rt): 1.05 min (method D)

Intermediate G-2

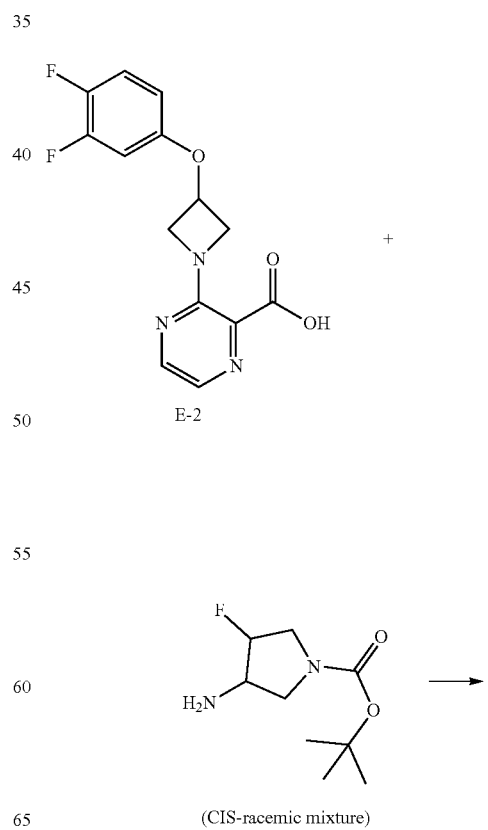

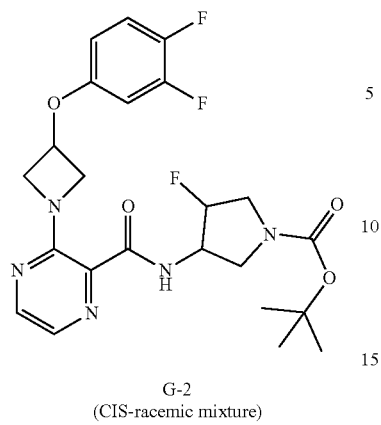

G-2
(CIS-racemic mixture)

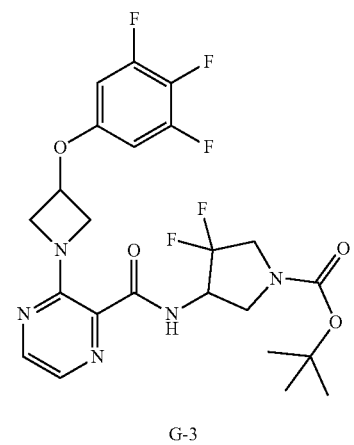

G-3

To a mixture of intermediate E-2 (250.0 mg, 814.0 µmol, cis-tert-butyl-4-amino-3-fluoropyrrolidine-1-carboxylate (174.5 mg, 854.0 µmol and DIPEA (553.3 µL, 3.3 mmol) in acetonitrile (4 mL) was added CIP (249.3 mg, 895.0 µmol. After stirring for 2 h at RT, the reaction mixture was diluted with water. The organic phase was separated and purified directly by preparative HPLC to provide intermediate G-2 as CIS-racemic mixture.

ESI-MS: 494 [M+H]$^+$; HPLC (Rt): 1.01 min (method D)

Intermediate G-3

To a mixture of intermediate E-1 (250.0 mg, 715.0 µmol, tert-butyl-4-amino-3,3-difluoropyrrolidine-1-carboxylate (166.8 mg, 751.0 µmol and DIPEA (486.1 µL, 2.9 mmol) in acetonitrile (4 mL) was added CIP (219.0 mg, 786.0 µmol. After stirring for 2 h at RT, the reaction mixture was diluted with water. The organic phase was separated and purified directly by preparative HPLC to provide intermediate G-3 as racemic mixture.

ESI-MS: 530 [M+H]$^+$; HPLC (Rt): 1.11 min (method D)

Intermediate G-4

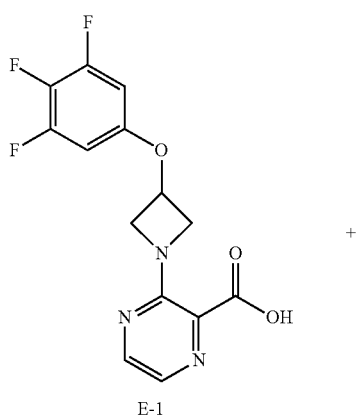

E-1

+

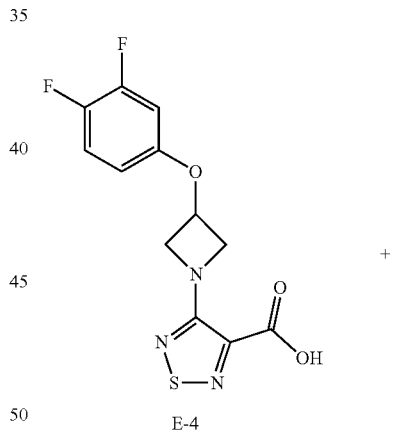

E-4

+

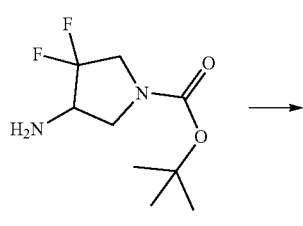

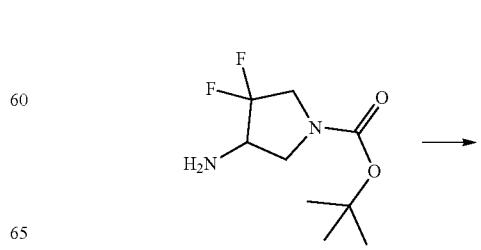

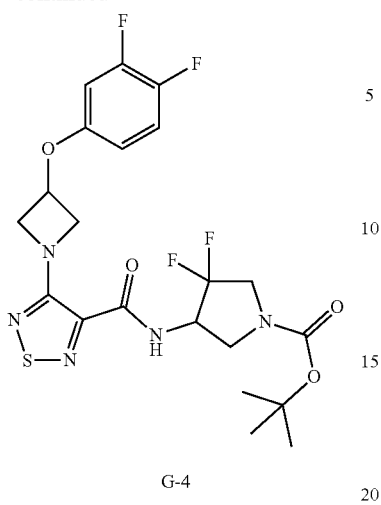

G-4

To a mixture of intermediate E-4 (150.0 mg, 479.0 μmol, tert.-butyl-4-amino-3,3-difluoropyrrolidine-1-carboxylate (117.1 mg, 527.0 μmol and DIPEA (248.5 μL, 1.4 mmol) in acetonitrile (5 mL) was added CIP (146.7 mg, 1.4 mmol). After stirring for 16 h at RT aqueous 1N sodium hydroxide solution was added, and the mixture was extracted 2× with DCM. The combined organic phases were washed with water, dried over sodium sulfate, filtered, and concentrated under reduced pressure. The remainder was purified by preparative HPLC to provide intermediate G-4 as racemic mixture.

ESI-MS: 518 [M+H]$^+$; HPLC (Rt): 0.88 min (method B)

Intermediate (S)-G-4

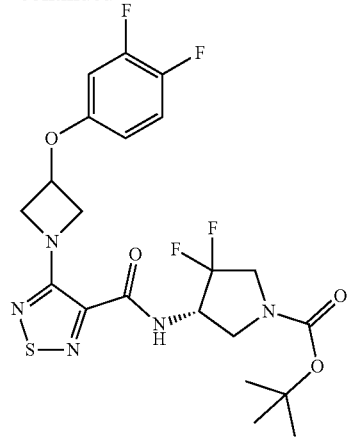

(S)-G-4

To a mixture of intermediate E-4 (150.0 mg, 479.0 μmol, (S)-tert.-butyl-4-amino-3,3-difluoropyrrolidine-1-carboxylate (CAS No. 2381400-91-3, 123.2 mg, 527.0 μmol and DIPEA (331.3 μL, 1.9 mmol) in acetonitrile (2 mL) was added CIP (146.7 mg, 527.0 μmol. After stirring for 16 h at RT water was added, and the mixture was extracted with DCM. The organic phase was dried over sodium sulfate, filtered and concentrated under reduced pressure. The remainder was purified by preparative HPLC to provide chiral intermediate (S)-G-4.

ESI-MS: 518 [M+H]$^+$; HPLC (Rt): 1.14 min (method D)

Intermediate H-1

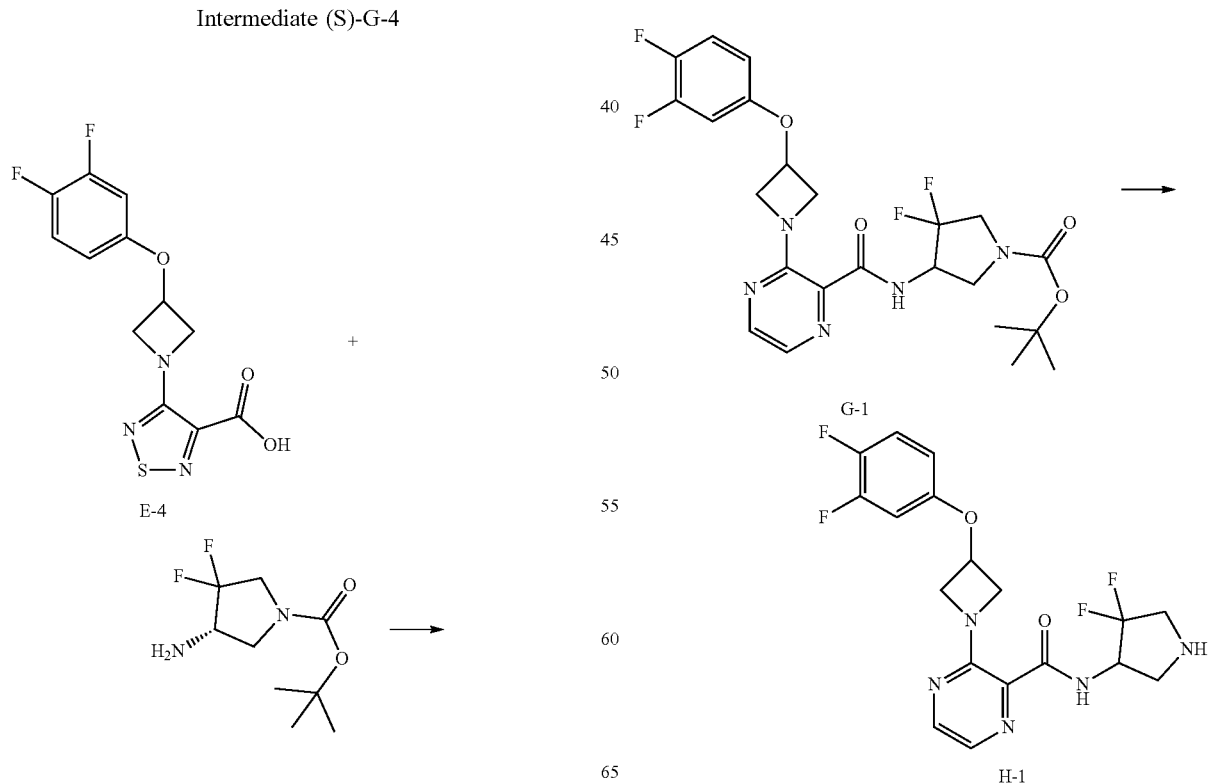

To a mixture of intermediate G-1 (358.0 mg, 700.0 µmol in dichloromethane (4 mL) was added TFA (1.0 mL, 13.0 mmol). After stirring for 2 h at RT the reaction mixture was concentrated under reduced pressure. To the remainder was added a mixture of acetonitrile and water. Lyophilization of the mixture provided crude intermediate H-1 as TFA salt as racemic mixture.

ESI-MS: 412 [M+H]⁺; HPLC (Rt): 0.57 min (method D)

Intermediate H-2

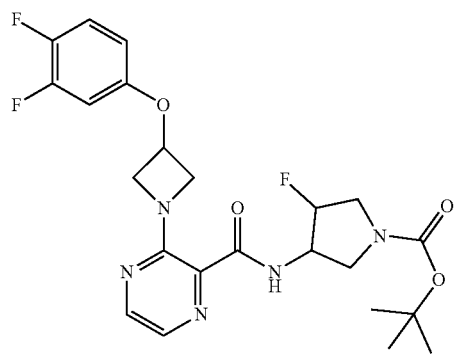

G-2
(CIS-racemic mixture)

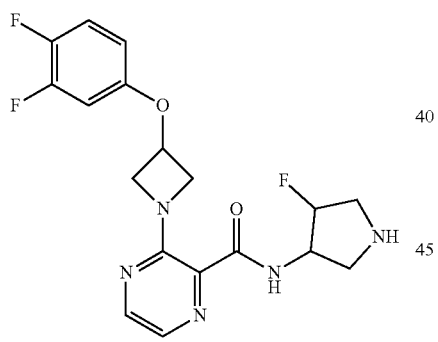

H-2
(CIS-racemic mixture)

To a mixture of intermediate G-2 (283.0 mg, 573.0 µmol, CIS-racemic mixture) in dichloromethane (3.5 mL) was added TFA (0.8 mL, 10.3 mmol). After stirring for 2.5 h at RT the reaction mixture was concentrated under reduced pressure to provide crude intermediate H-2 as TFA salt as CIS-racemic mixture.

ESI-MS: 394 [M+H]⁺; HPLC (Rt): 0.54 min (method D)

Intermediate H-3

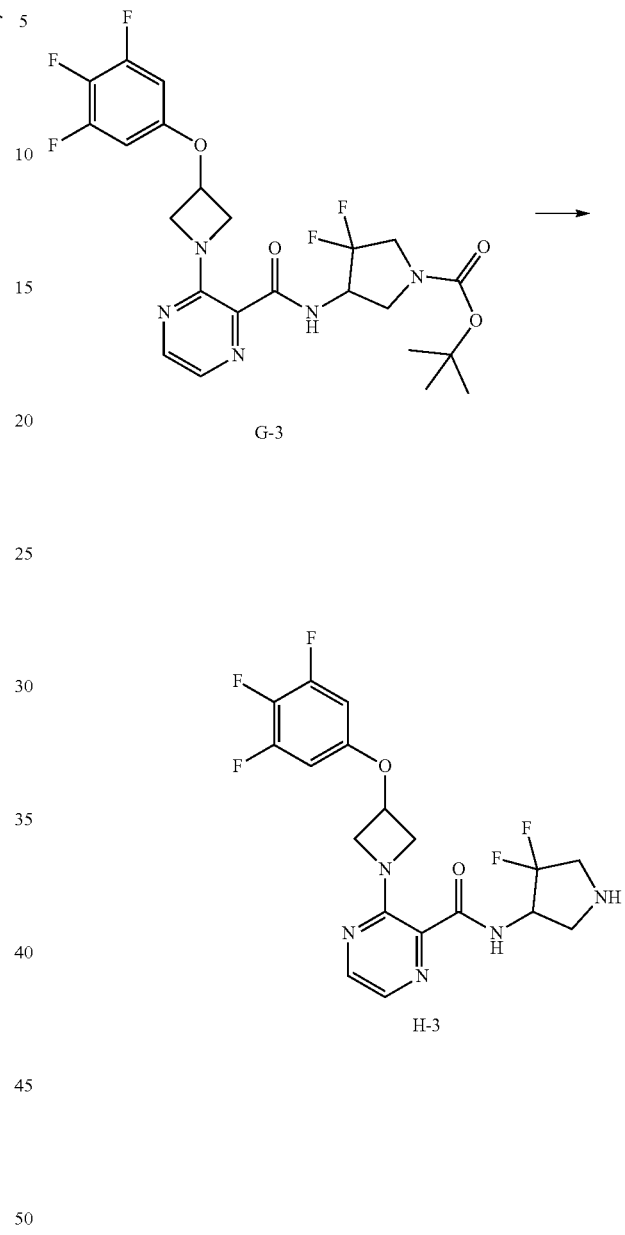

G-3

H-3

To a mixture of intermediate G-3 (161.0 mg, 304.0 µmol) in dichloromethane (4 mL) was added TFA (0.45 mL, 5.78 mmol). After stirring for 1.5 h at RT the reaction mixture was concentrated under reduced pressure. The remained was dissolved in a mixture of dichloromethane/methanol (9:1 v/v) and washed with saturated aqueous NaHCO₃ solution. The organic phase was separated via a phase separation cartridge and was concentrated under reduced pressure. A fraction this material was purified by HPLC (basic conditions) to provide intermediate H-3 as racemic mixture.

ESI-MS: 430 [M+H]⁺; HPLC (Rt): 0.59 min (method B)

Intermediate H-4

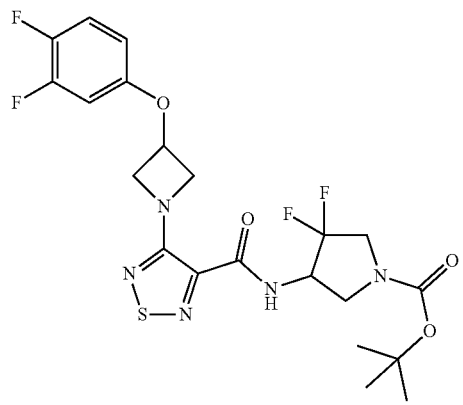

G-4

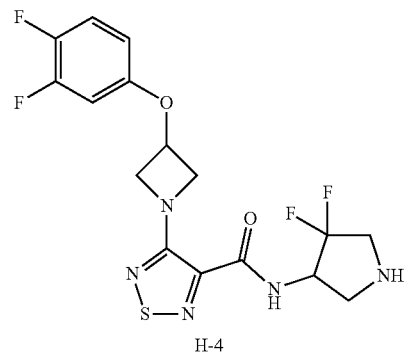

H-4

A mixture of intermediate G-4 (200.0 mg, 386.0 µmol) and p-toluenesulfonic acid monohydrate (257.3 mg, 1.4 mmol) in acetonitrile (4 mL) was stirred for 3 h. Water and aqueous ammonia solution was added, filtered and purified by preparative HPLC to give intermediate H-4 as racemic mixture.

ESI-MS: 418 [M+H]$^+$; HPLC (Rt): 0.64 min (method D)

Intermediate (S)-H-4

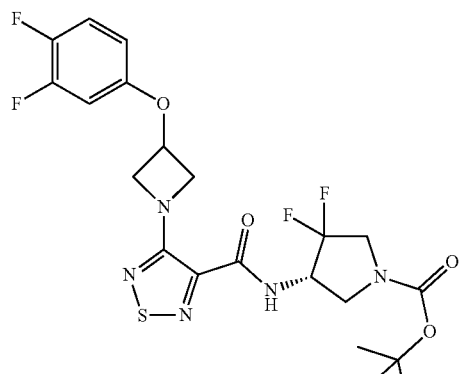

(S)-G-4

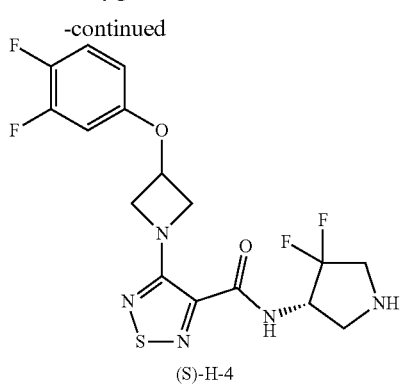

(S)-H-4

A mixture of intermediate (S)-G-4 (155.0 mg, 300.0 µmol) and p-toluenesulfonic acid monohydrate (199.4 mg, 1.1 mmol) in acetonitrile (3 mL) was stirred for 16 h at RT. Water and aqueous ammonia solution was added, the mixture was filtered and purified by preparative HPLC to give intermediate (S)-H-4.

ESI-MS: 418 [M+H]$^+$; HPLC (Rt): 0.64 min (method D)

Example 1

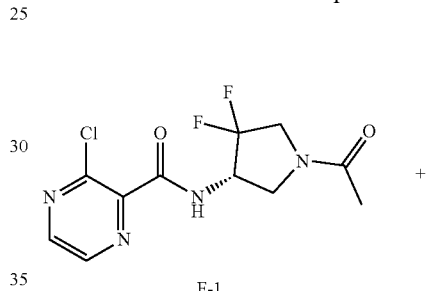

F-1

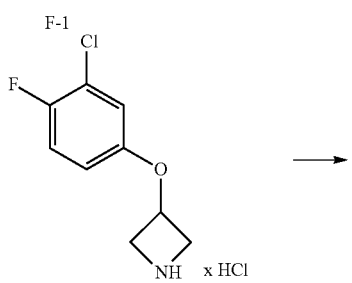

B-4

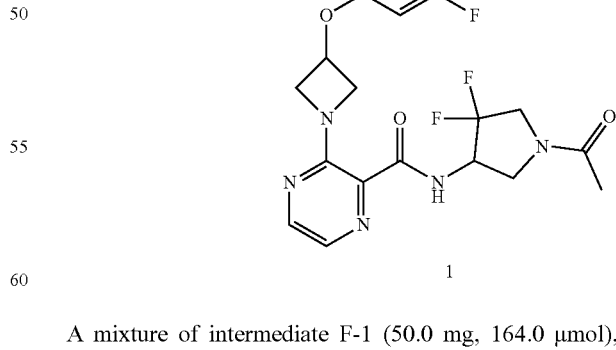

1

A mixture of intermediate F-1 (50.0 mg, 164.0 µmol), intermediate B-4 (46.9 mg, 197.0 µmol) and triethylamine (49.8 mg, 492.0 µmol) in DMA (2 mL) was stirred at 85° C. for 1 h. After cooling to RT the reaction mixture was directly purified by preparative HPLC to provide example 1 as racemic mixture.

ESI-MS: 470/472 [M+H]+; HPLC (Rt): 0.65 min (method B)

Example 2

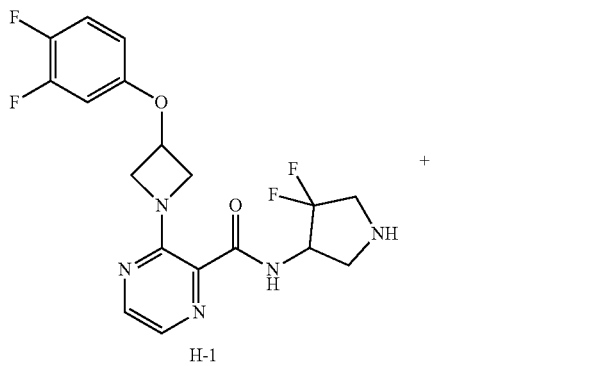

H-1

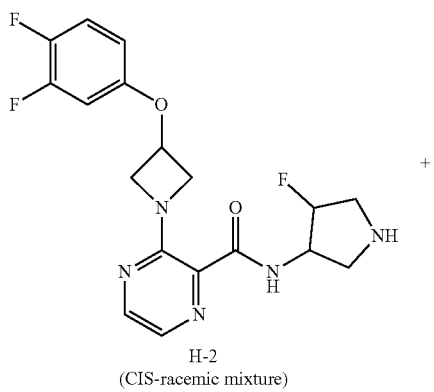

2

To a mixture of intermediate H-1 (crude TFA salt, 100.0 mg, 129.0 µmol and DIPEA (56.0 µL, 324.0 µmol in acetonitrile (1 mL) was added propionyl chloride (13.6 µL, 155.0 µmol. After stirring for 30 min at RT the mixture was made alkaline by addition of aqueous ammonia and water. The mixture was filtered and purified directly by preparative HPLC to provide example 2 as racemic mixture.

ESI-MS: 468 [M+H]+; HPLC (Rt): 0.86 min (method D)

Example 3

H-2
(CIS-racemic mixture)

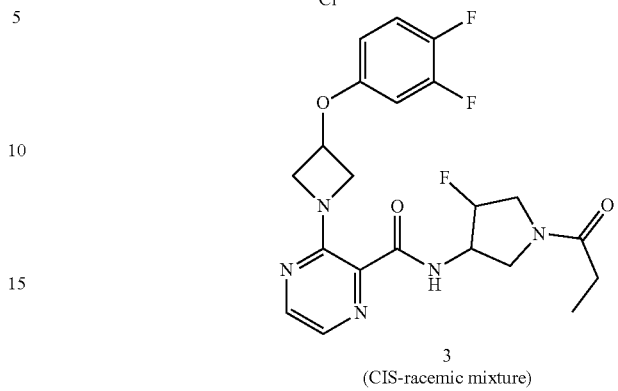

3
(CIS-racemic mixture)

To a mixture of intermediate H-2 (crude TFA salt, 548.0 mg, 573.0 µmol, CIS-racemic mixture) and DIPEA (0.4 mL, 2.3 mmol) in acetonitrile (3 mL) was added acetyl chloride (44.8 µL, 631.0 µmol at 0° C. After stirring for 30 min at 0° C. the mixture was made alkaline by addition of aqueous ammonia and water. The mixture was filtered and purified directly by preparative HPLC to provide example 3 as CIS-racemic mixture.

ESI-MS: 436 [M+H]+; HPLC (Rt): 0.75 min (method D)

Example 4

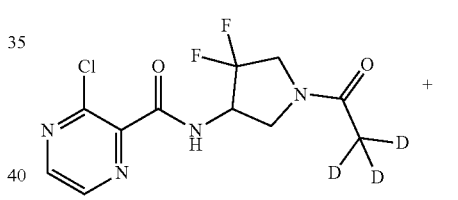

F-2

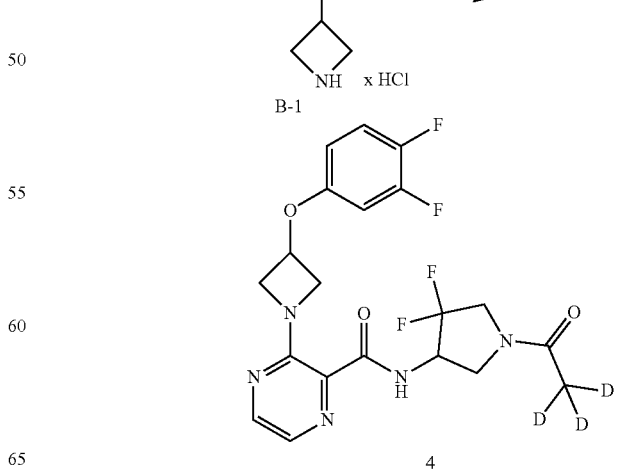

B-1

4

A mixture of intermediate F-1 (50.0 mg, 164.0 μmol, intermediate B-1 (46.9 mg, 197.0 μmol and triethylamine (49.8 mg, 492.0 μmol in DMA (2 mL) was stirred at 85° C. for 1 h. After cooling to RT the reaction mixture was directly purified by preparative HPLC to provide example 4 as racemic mixture.

ESI-MS: 457 [M+H]⁺; HPLC (Rt): 0.80 min (method D)

Example 5

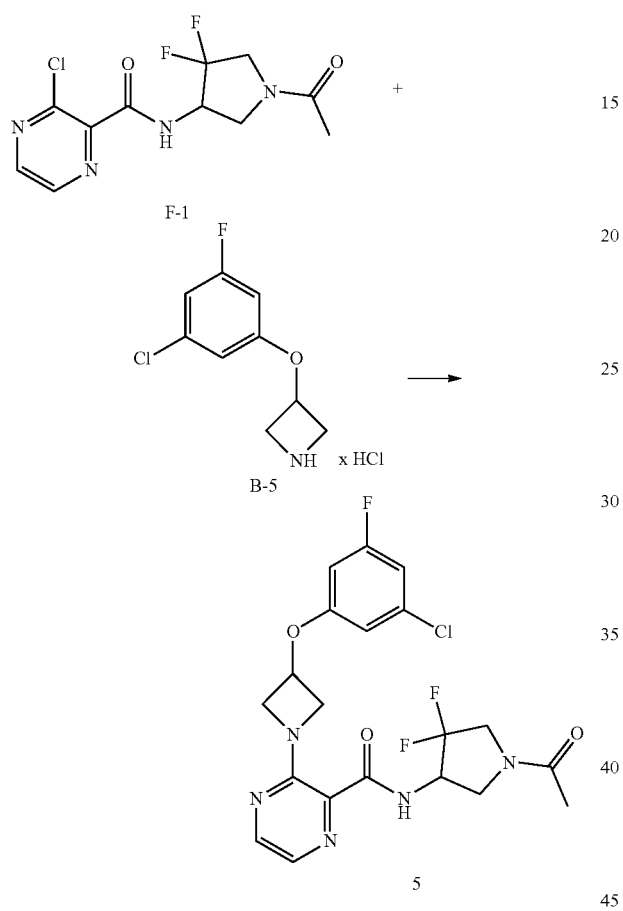

A mixture of intermediate F-1 (23.0 mg, 75.0 μmol, intermediate B-5 (19.8 mg, 83.0 μmol and triethylamine (21.2 μL, 151.0 μmol in DMA (0.5 mL) was stirred at 80° C. for 30 min. After cooling to RT the reaction mixture was directly purified by preparative HPLC to provide example 5 as racemic mixture.

ESI-MS: 470/472 [M+H]⁺; HPLC (Rt): 0.91 min (method D)

Example 6

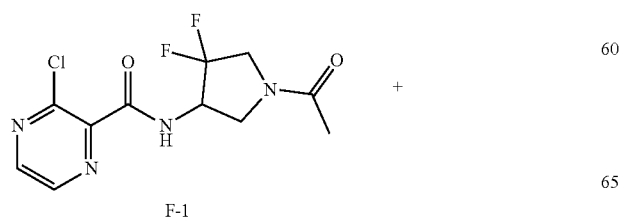

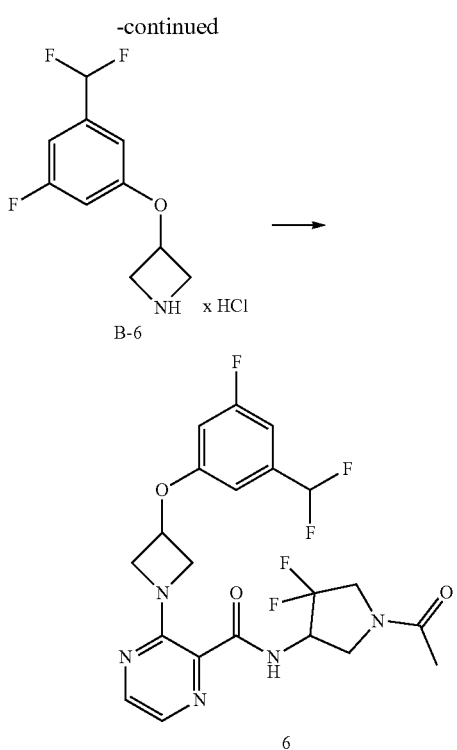

A mixture of intermediate F-1 (85.0 mg, 179.0 μmol, intermediate B-6 (58.4 mg, 214.0 μmol and triethylamine (50.1 μL, 357.0 μmol in DMA (1.5 mL) was stirred at 100° C. for 1.5 h. After cooling to RT the reaction mixture was directly purified by preparative HPLC to provide example 6 as racemic mixture.

ESI-MS: 486 [M+H]⁺; HPLC (Rt): 0.63 min (method B)

Example 7

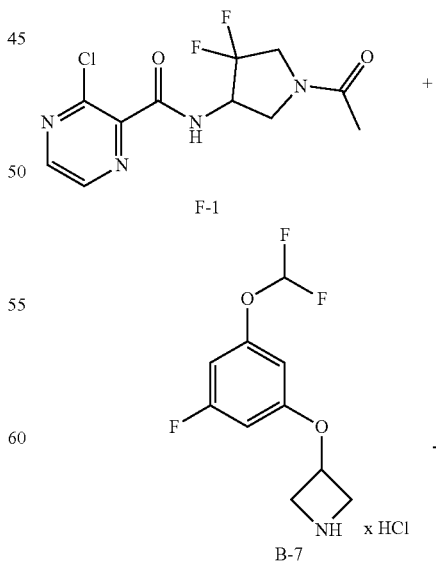

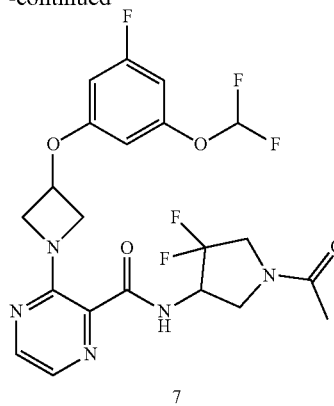

7

A mixture of intermediate F-1 (23.0 mg, 75.0 μmol, intermediate B-7 (22.4 mg, 83.0 μmol and triethylamine (21.2 μL, 151.0 μmol in DMA (0.5 mL) was stirred at 80° C. for 30 min. After cooling to RT the reaction mixture was directly purified by preparative HPLC to provide example 7 as racemic mixture.

ESI-MS: 502 [M+H]$^+$; HPLC (Rt): 0.87 min (method D)

Examples 8, 8a and 8b (73.7 μL, 525.0 μmol) in DMA (1.5 mL) was stirred at 100° C. for 1.5 h. After cooling to RT the reaction mixture was extracted 3× with ethyl acetate. The combined organic phases were dried over $Na_2SO_4$, filtered and concentrated under reduced pressure. The remainder was directly purified by preparative HPLC to provide example 8 as racemic mixture.

ESI-MS: 454 [M+H]$^+$; HPLC (Rt): 0.58 min (method B)

Preparative chiral separation: Racemic amide 8 (90.0 mg, 199.0 μmol) was submitted to preparative chiral SFC separation (Sepiatec basic, Chiralpak ART® Cellulose-SB, 10×250 mm, 5 μm, mobile phase: eluent A: supercritical $CO_2$, eluent B: methanol containing 20 mM conc aq ammonia, gradient A:B 75:25, flow rate 10 mL/min, temperature 40° C., wavelength 220 nm, system back pressure 150 bar, sample concentration 25 mg/mL, injection volume 200 μL) to provide:

Example 8a (single stereoisomer a): Rt=2.72 min (method G). Enantiomeric purity: 99.1% ee.

Example 8b (single stereoisomer b): Rt=3.42 min (method G). Enantiomeric purity: 96.8% ee.

Synthesis of Example 8b from Chiral Intermediate (S)-F-1

A mixture of intermediate (S)-F-1 (70.0 mg, 230.0 μmol, intermediate B-1 (61.1 mg, 276.0 μmol and triethylamine (80.6 μL, 574.0 μmol in DMA (0.5 mL) was stirred at 100°

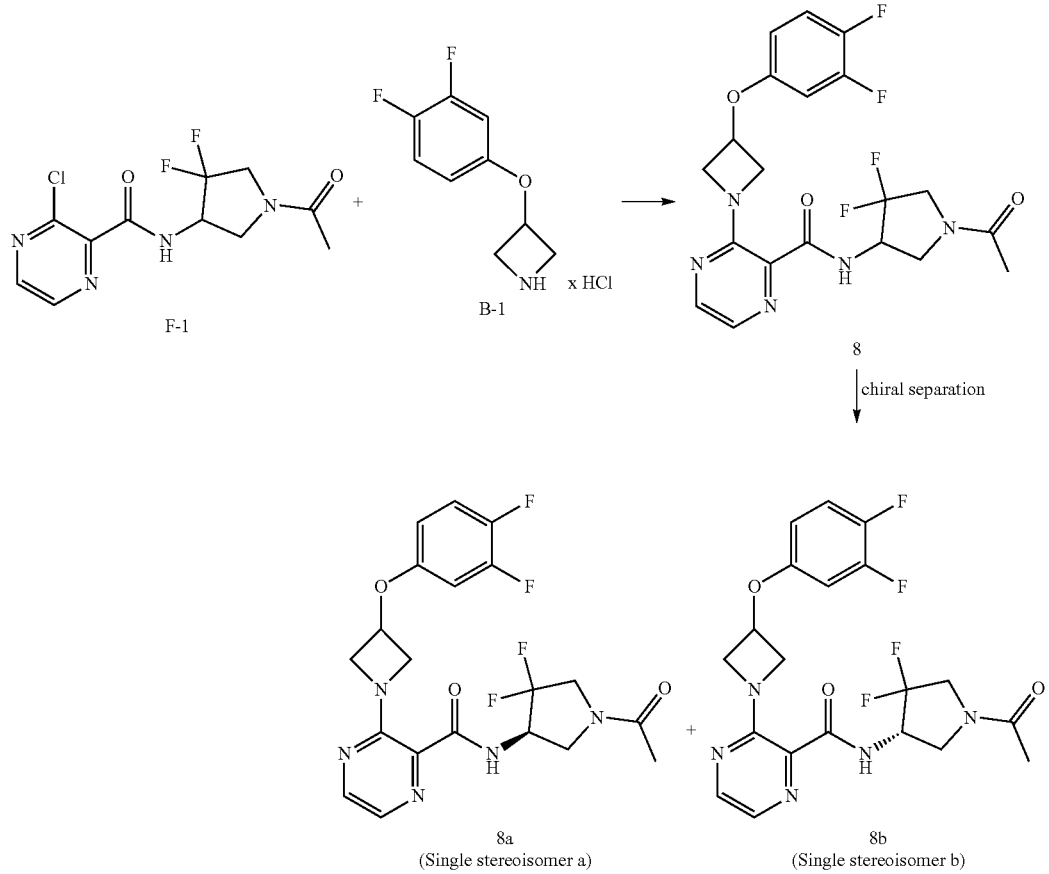

A mixture of intermediate F-1 (80.0 mg, 263.0 μmol), intermediate B-1 (69.8 mg, 315.0 μmol) and triethylamine C. for 1.5 h. After cooling to RT, the reaction mixture was diluted with acetonitrile/water mixture and aqueous ammonia solution. The mixture was filtered and purified directly by preparative HPLC to provide example 8b.

ESI-MS: 454 [M+H]+; HPLC (Rt): 0.81 min (method D)

Chiral HPLC: Rt=3.48 min (method G). Enantiomeric purity: >98% ee.

Example 9

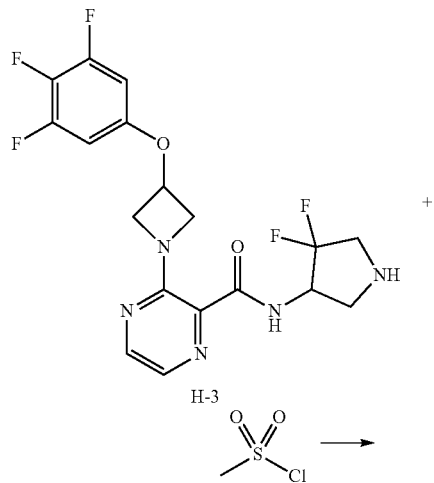

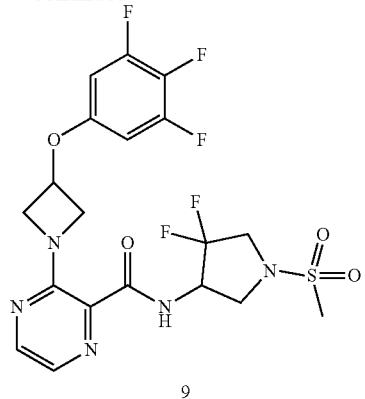

To a mixture of intermediate H-3 (crude TFA salt, 100.0 mg, 114.0 μmol and triethylamine (96.8 μL, 685.0 μmol in THF (2 mL) was added methanesulfonyl chloride (8.8 μL, 114.0 μmol at 0° C. After stirring for 2 h at 0° C. Water was added and the reaction mixture was extracted with dichloromethane. The organic phase was separated and concentrated under reduced pressure. The remainder was dissolved in a mixture of acetonitrile/water/conc. aqueous ammonia and was purified by preparative HPLC to provide example 9 as racemic mixture.

ESI-MS: 508 [M+H]+; HPLC (Rt): 0.93 min (method D)

Examples 10, 10a and 10b

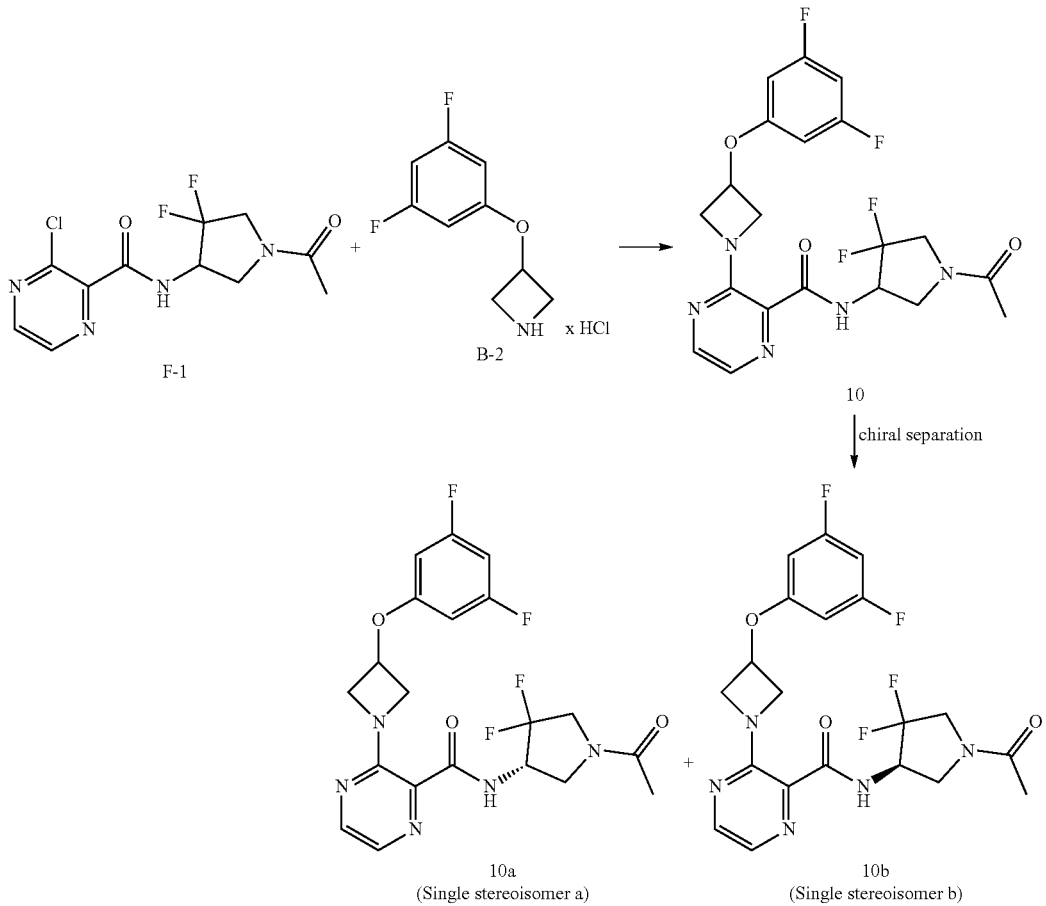

A mixture of intermediate F-1 (100.0 mg, 210.0 μmol), intermediate B-2 (60.1 mg, 252.0 μmol) and triethylamine (59.0 μL, 420.0 μmol) in DMA (1.5 mL) was stirred at 100° C. for 1.5 h. After cooling to RT the reaction mixture was directly purified by preparative HPLC to provide example 10 as racemic mixture.

ESI-MS: 454 [M+H]$^+$; HPLC (Rt): 0.63 min (method B)

Chiral HPLC: Rt=1.39 min (method H). Enantiomeric purity: >98% ee.

Examples 11, 11a and 11b

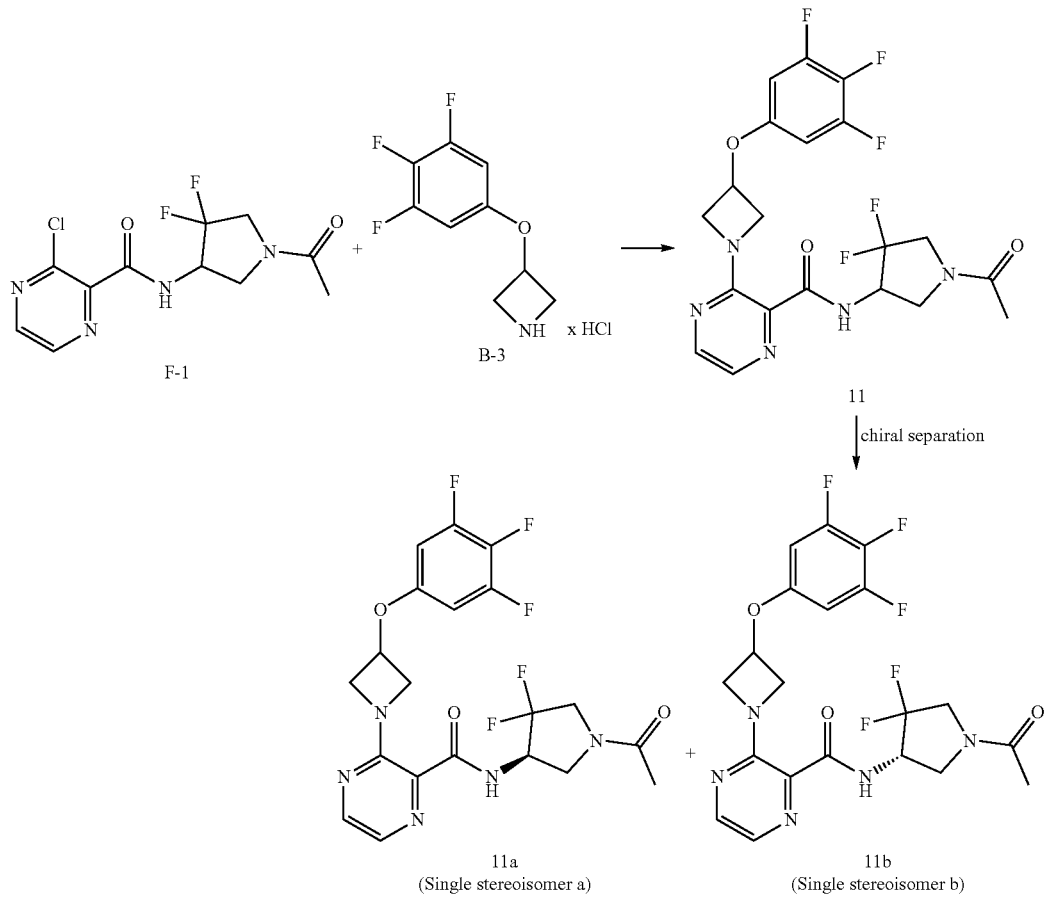

Preparative chiral separation: Racemic amide 10 (30.0 mg, 66.0 μmol) was submitted to preparative chiral SFC separation (Sepiatec basic, Lux® Cellulose-4, 10×250 mm, 5 μm, mobile phase: eluent A: supercritical $CO_2$, eluent B: methanol containing 20 mM conc aq ammonia, gradient A:B 80:20, flow rate 10 mL/min, temperature 40° C., wavelength 220 nm, system back pressure 150 bar, sample concentration 10 mg/mL, injection volume 100 μL) to provide:

Example 10a (single stereoisomer a): Rt=1.42 min (method H). Enantiomeric purity: 100.0% ee.

Example 10b (single stereoisomer b): Rt=1.62 min (method H). Enantiomeric purity: 96.0% ee.

Synthesis of Example 10a from Chiral Intermediate (S)-F-1

A mixture of intermediate (S)-F-1 (70.0 mg, 230.0 μmol), intermediate B-2 (61.1 mg, 276.0 μmol and triethylamine (80.6 μL, 574.0 μmol in DMA (0.5 mL) was stirred at 100° C. for 1.5 h. After cooling to RT, the reaction mixture was diluted with acetonitrile/water mixture and aqueous ammonia solution. The mixture was filtered and purified directly by preparative HPLC to provide example 10a.

ESI-MS: 454 [M+H]$^+$; HPLC (Rt): 0.83 min (method D)

A mixture of intermediate F-1 (85.0 mg, 179.0 μmol, intermediate B-3 (55.2 mg, 214.0 μmol and triethylamine (50.1 μL, 357.0 μmol in DMA (1.5 mL) was stirred at 100° C. for 1.5 h. After cooling to RT the reaction mixture was extracted 3× with ethyl acetate. The combined organic phases were dried over $Na_2SO_4$, filtered and concentrated under reduced pressure. The remainder was directly purified by preparative HPLC to provide example 11 as racemic mixture.

ESI-MS: 472 [M+H]$^+$; HPLC (Rt): 0.65 min (method B)

Preparative chiral separation: Racemic amide 11 (207.0 mg, 439.0 μmol was submitted to preparative chiral SFC separation (Sepiatec basic, Chiralpak ART® Cellulose-SB, 10×250 mm, 5 μm, mobile phase: eluent A: supercritical $CO_2$, eluent B: methanol containing 20 mM conc aq ammonia, gradient A:B 80:20, flow rate 10 mL/min, temperature 40° C., wavelength 220 nm, system back pressure 150 bar, sample concentration 25 mg/mL, injection volume 100 μL) to provide:

Example 11a (single stereoisomer a): Rt=3.33 min (method I). Enantiomeric purity: >98% ee.

Example 11b (single stereoisomer b): Rt=4.32 min (method I). Enantiomeric purity: n.d.

89

Synthesis of Example 11b from Chiral Intermediate (S)-F-1

A mixture of intermediate (S)-F-1 (70.0 mg, 230.0 µmol, intermediate B-3 (66.1 mg, 276.0 µmol and triethylamine (80.6 µL, 574.0 µmol in DMA (0.5 mL) was stirred at 100° C. for 1.5 h. After cooling to RT, the reaction mixture was diluted with acetonitrile/water mixture and aqueous ammonia solution. The mixture was filtered and purified directly by preparative HPLC to provide example 11b.

ESI-MS: 472 [M+H]$^+$; HPLC (Rt): 0.86 min (method D)

Chiral HPLC: Rt=4.33 min (method I). Enantiomeric purity: >98% ee.

Example 12

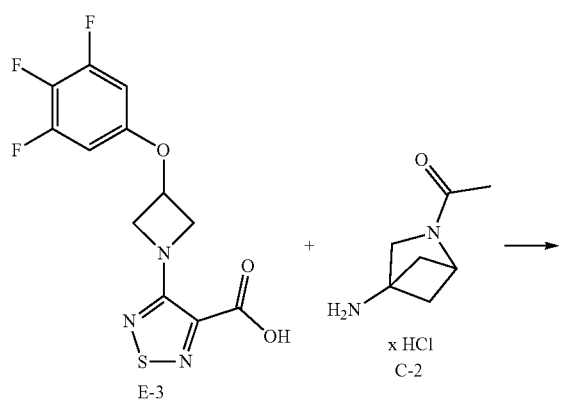

90

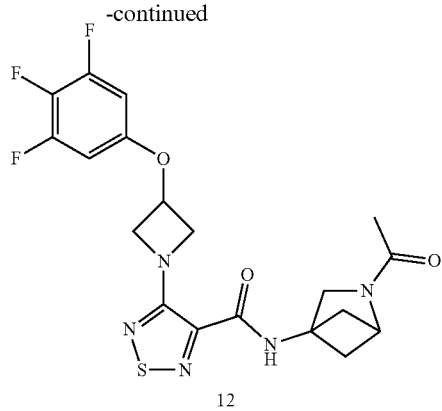

To a mixture of intermediate E-3 (50.0 mg, 151.0 µmol, DIPEA (104.4 µL, 604.0 µmol and intermediate C-2 (HCl salt, 30.9 mg, 166.0 µmol in acetonitrile (0.7 mL) was added CIP (46.3 mg, 166.0 µmol. After stirring for 2 h at RT the mixture was diluted with aq. ammonia solution and water. After filtration the mixture was purified directly by preparative HPLC to provide example 12.

ESI-MS: 454 [M+H]$^+$; HPLC (Rt): 0.66 min (method B)

Examples 13, 13a and 13b

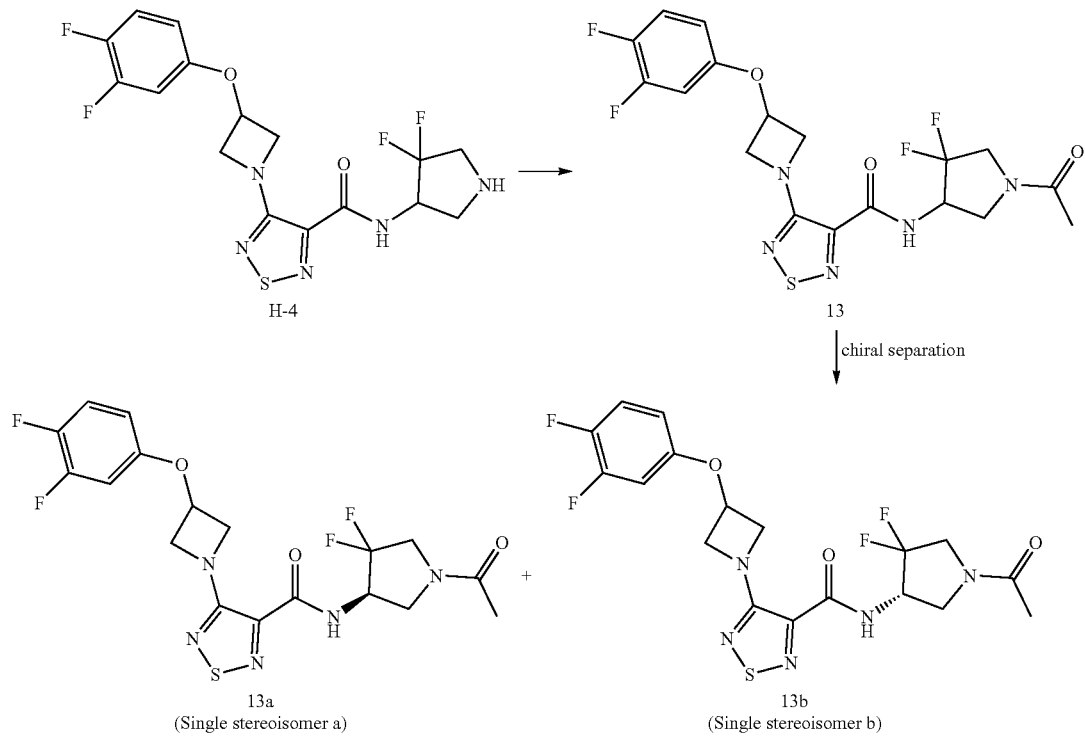

To a mixture of intermediate H-4 (75.0 mg, 180.0 µmol) and DIPEA (123.1 µL, 719.0 µmol) in acetonitrile (2 mL) was added acetyl chloride (18.4 µL, 270.0 µmol). After stirring for 1 h, an additional amount of acetyl chloride (9.0 µL) and DIPEA (30.8 µL) were added and stirring was continued for 30 min. Water was added and the reaction mixture was filtered and purified directly by HPLC to provide product 13 as racemic mixture.

ESI-MS: 460 [M+H]⁺; HPLC (Rt): 0.90 min (method D)

Preparative chiral separation: Racemic amide 13 (60.0 mg, 131.0 µmol) was submitted to preparative chiral SFC separation (Sepiatec basic, Lux® Cellulose-3, 10×250 mm, 5 µm, mobile phase: eluent A: supercritical CO$_2$, eluent B: methanol containing 20 mM conc aq ammonia, gradient A:B 85:15, flow rate 10 mL/min, temperature 40° C., wavelength 220 nm, system back pressure 150 bar, sample concentration 11 mg/mL, injection volume 200 µL) to provide:

Example 13a (single stereoisomer a): Rt=0.86 min (method J). Enantiomeric purity: >99% ee.

Example 13b (single stereoisomer b): Rt=1.07 min (method J). Enantiomeric purity: 99.2% ee.

Synthesis of Example 13b from Chiral Intermediate (S)-H-4

To a mixture of intermediate (S)-H-4 (30.0 mg, 68.0 µmol) and DIPEA (46.8 µL, 273.0 µmol) in acetonitrile (0.75 mL) was added acetyl chloride (7.0 µL, 102.0 µmol). After stirring for 2.5 h at RT, water was added, and the reaction mixture was filtered and purified directly by HPLC to provide example 13b.

ESI-MS: 460 [M+H]⁺; HPLC (Rt): 0.90 min (method D)
Chiral HPLC: Rt=1.10 min (method J). Enantiomeric purity: >98% ee.

Examples 14, 14a and 14b

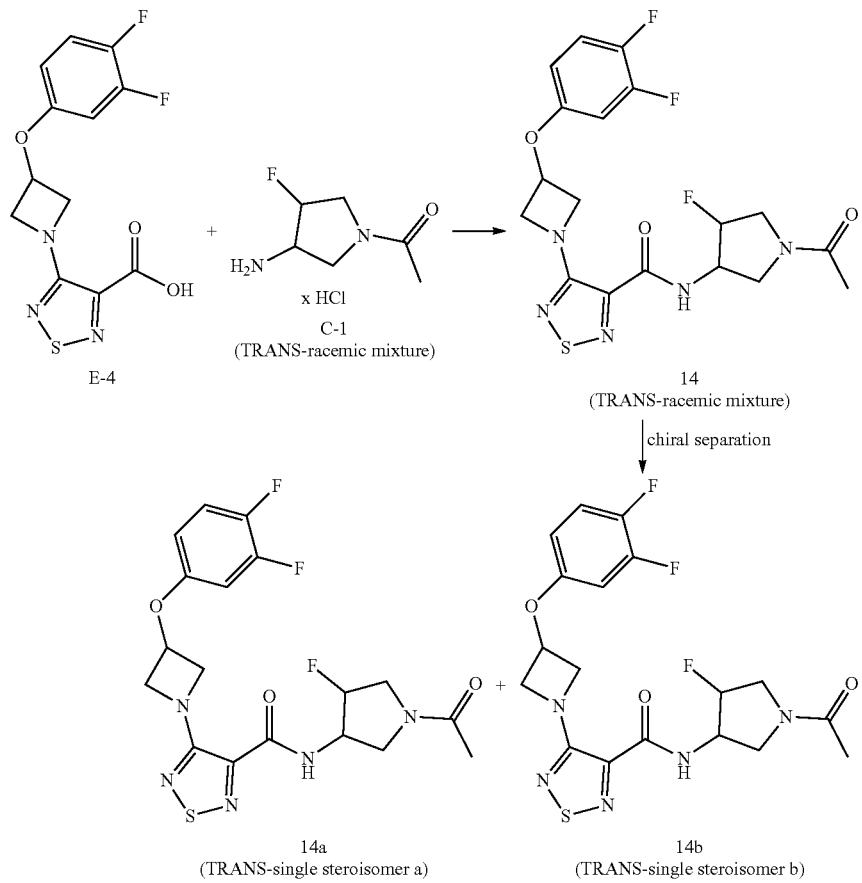

14a
(TRANS-single steroisomer a)

14b
(TRANS-single steroisomer b)

To a mixture of intermediate E-4 (150.0 mg, 479.0 µmol, DIPEA (248.5 µL, 1.4 mmol) and intermediate C-1 (HCl salt, 96.2 mg, 527.0 µmol, TRANS-racemic mixture) in acetonitrile (5 mL) was added CIP (146.7 mg, 527.0 µmol. After stirring for 16 h at RT the mixture was diluted with aq. 1N sodium hydroxide solution and extracted twice with DCM. The combined organic phases were washed with water, then dried and concentrated under reduced pressure. The remainder was purified by preparative HPLC to provide example 14 as TRANS-racemic mixture.

ESI-MS: 442 [M+H]⁺; HPLC (Rt): 0.65 min (method B)

Preparative chiral separation: TRANS-Racemic amide 14 (135.0 mg, 306.0 µmol) was submitted to preparative chiral SFC separation (Sepiatec 2 Prep SFC 100, CHIRAL ART® Amylose-SA, 20×250 mm, 5 µm, mobile phase: eluent A: supercritical CO$_2$, eluent B: methanol containing 20 mM conc aq ammonia, gradient A:B 75:25, flow rate 40 mL/min, temperature 40° C., wavelength 220 nm, system back pressure 150 bar, sample concentration 23 mg/mL, injection volume 100 µL) to provide:

Example 14a (TRANS-single stereoisomer a): Rt=0.93 min (method K). Enantiomeric purity: >98% ee.

Example 14b (TRANS-single stereoisomer b): Rt=1.24 min (method K). Enantiomeric purity: >98% ee.

Examples 15, 15a and 15b

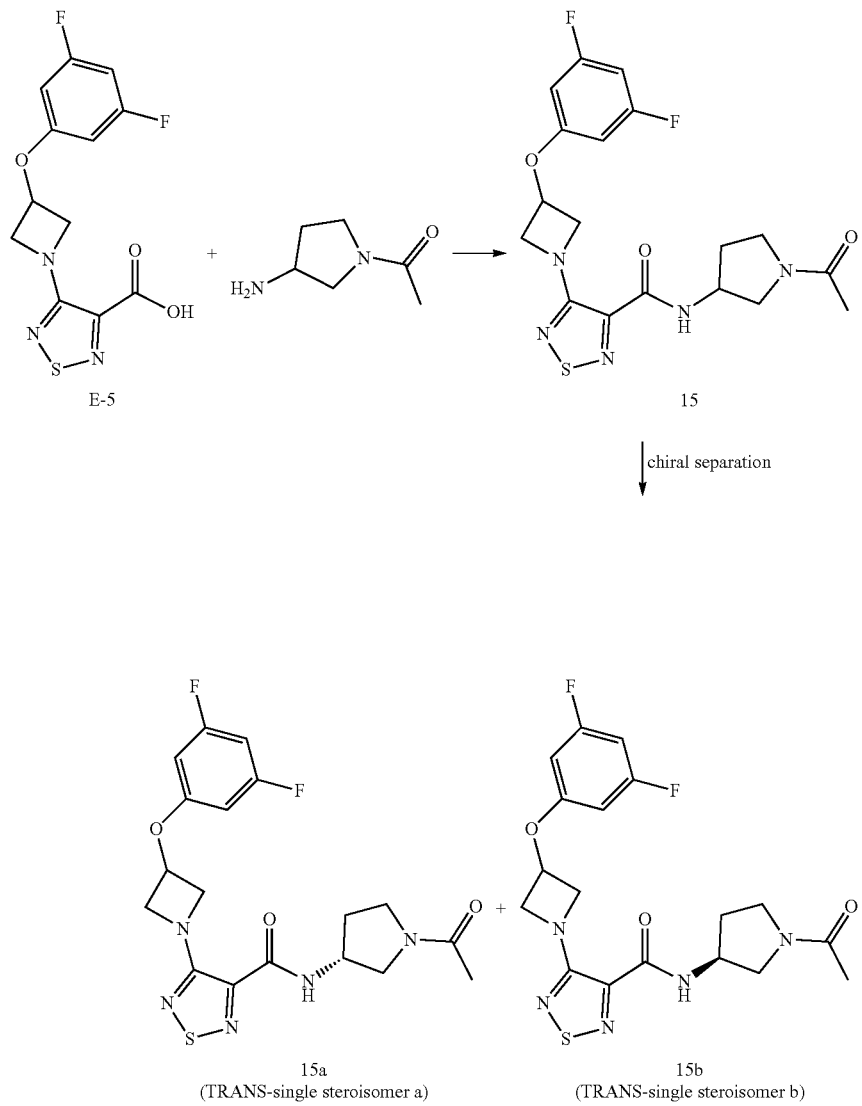

15a
(TRANS-single steroisomer a)

15b
(TRANS-single steroisomer b)

To a mixture of intermediate E-5 (200.0 mg, 575.0 µmol), DIPEA (248.5 µL, 1.4 mmol) and N-acetyl-pyrrolidin-3-ylamine (83.5 mg, 632.0 µmol) in acetonitrile (3 mL) was added CIP (176.1 mg, 632.0 µmol). After stirring for 16 h at RT the mixture was diluted with water and extracted twice with ethyl acetate. The aqueous phase was filtered and was purified by preparative HPLC to provide example 15 as racemic mixture.

ESI-MS: 424 [M+H]$^+$; HPLC (Rt): 0.84 min (method D)

Preparative chiral separation: Racemic amide 15 (128.6 mg, 304.0 µmol) was submitted to preparative chiral SFC separation (Sepiatec 1 Prep SFC 100, Lux® Cellulose-2, 21.2×250 mm, 5 µm, mobile phase: eluent A: supercritical $CO_2$, eluent B: ethanol containing 20 mM conc aq ammonia, gradient A:B 70:30, flow rate 60 mL/min, temperature 40° C., wavelength 220 nm, system back pressure 150 bar, sample concentration 20 mg/mL, injection volume 200 µL) to provide Example 15a (single stereoisomer a): Rt=3.74 min (method L). Enantiomeric purity: >98% ee.

Example 15b (single stereoisomer b): Rt=4.27 min (method L). Enantiomeric purity: 96.8% ee.

Synthesis of Example 15a from Chiral Starting Material

To a mixture of intermediate E-5 (2.5 g, 8.0 mmol), DIPEA (248.5 µL, 1.4 mmol) and (R)-1-acetyl-pyrrolidin-3-ylamine hydrochloride (CAS No. 1286208-55-6, 1.3 g, 8.0 mmol) in acetonitrile (60 mL) was added CIP (2.2g, 8.0 mmol). After stirring for 45 min at RT, the mixture was filtered and was purified directly by preparative HPLC to provide example 15a.

ESI-MS: 424 [M+H]$^+$; HPLC (Rt): 0.99 min (method C)

Chiral HPLC: Rt=3.73 min (method L). Enantiomeric purity: >98% ee.

Examples 16, 16a and 16b

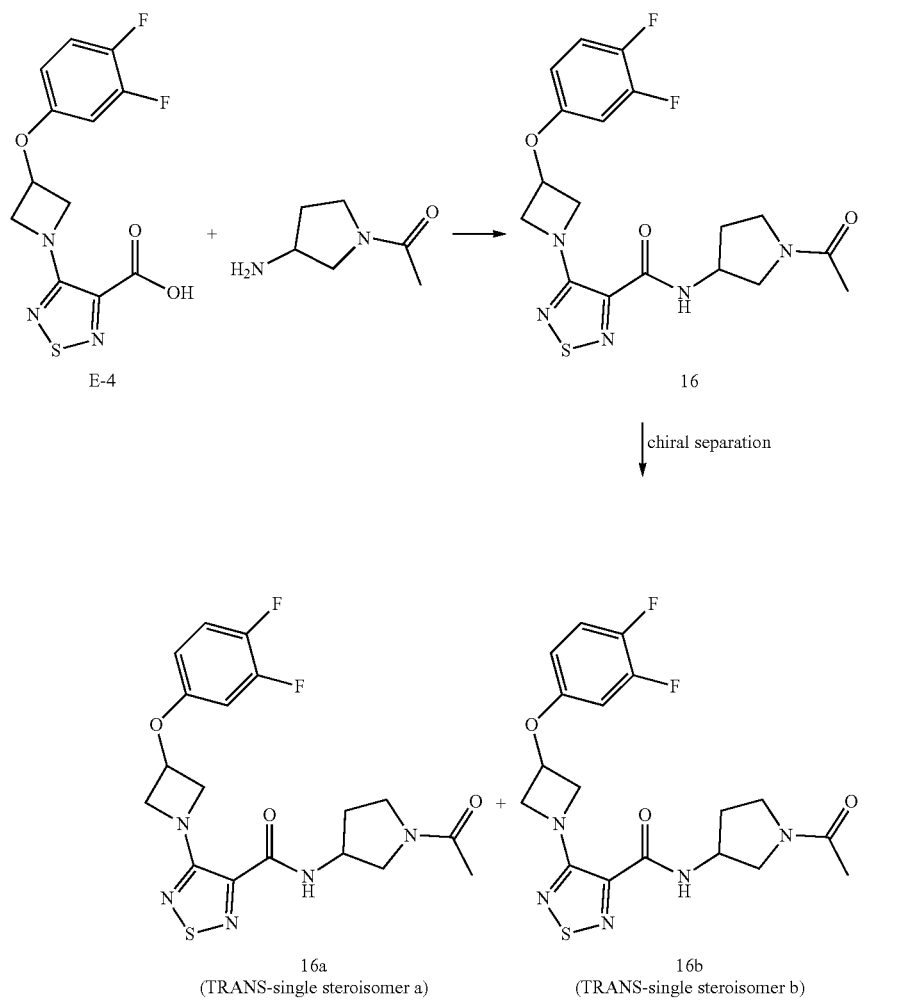

To a mixture of intermediate E-4 (220.0 mg, 702.0 μmol), DIPEA (303.7 μL, 1.8 mmol) and N-acetyl-pyrrolidin-3-ylamine (102.1 mg, 772.0 μmol) in acetonitrile (3 mL) was added CIP (215.2 mg, 772.0 μmol). After stirring for 2 h at RT the mixture was diluted with water, filtered and was purified directly by preparative HPLC to provide example 16 as racemic mixture.

ESI-MS: 424 [M+H]+; HPLC (Rt): 0.83 min (method D)

Preparative chiral separation: Racemic amide 16 (128.6 mg, 304.0 μmol) was submitted to preparative chiral SFC separation (Sepiatec 2 Prep SFC 100, Lux® Cellulose-2, 21.2×250 mm, 5 μm, mobile phase: eluent A: supercritical CO$_2$, eluent B: ethanol containing 20 mM conc aq ammonia, gradient A:B 65:35, flow rate 60 mL/min, temperature 40° C., wavelength 220 nm, system back pressure 150 bar, sample concentration 20 mg/mL, injection volume 250 μL) to provide:

Example 16a (single stereoisomer a): Rt=1.46 min (method M). Enantiomeric purity: >98% ee.

Example 16b (single stereoisomer b): Rt=1.65 min (method M). Enantiomeric purity: 96% ee.

The invention claimed is:

1. A compound of formula (I)

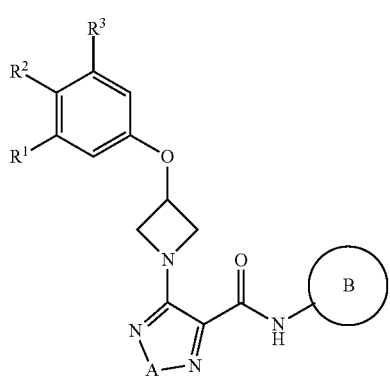

(I)

wherein

A is selected from the group consisting of
—CH=CH— and —S—;

B is selected from the group consisting of

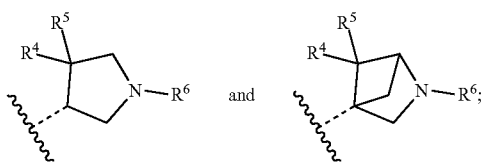

R¹ is selected from the group consisting of
  H— and F—;
R² is selected from the group consisting of
  H— and F—;
R³ is selected from the group consisting of
  F—, Cl—, F₂HCO—, F₃CO—, F₂HC— and F₃C—;
R⁴ is selected from the group consisting of
  H— and F—;
R⁵ is selected from the group consisting of
  H— and F—;
R⁶ is selected from the group consisting of
  H—, C$_{1-3}$-alkylcarbonyl- and C$_{1-3}$-alkylsulfonyl,
    wherein the C$_{1-3}$-alkylcarbonyl-group is selected from the group consisting of acetyl, ethanecarbonyl, propanecarbonyl, isopropanecarbonyl, and cyclopropanecarbonyl,
    wherein the C$_{1-3}$-alkylsulfonyl-group is selected from the group consisting of methanesulfonyl, ethanesulfonyl, propanesulfonyl, isopropanesulfonyl, and cyclopropanesulfonyl, and
    wherein the C$_{1-3}$-alkylcarbonyl-group and C$_{1-3}$-alkylsulfonyl-group are optionally substituted with 1 to 5 substituents independently selected from the group consisting of fluorine and deuterium;
or a pharmaceutically acceptable salt thereof.

2. The compound of claim 1, or a pharmaceutically acceptable salt thereof, wherein
A is —CH=CH—.

3. The compound of claim 1, or a pharmaceutically acceptable salt thereof, wherein
A is —S—.

4. The compound of claim 1, or a pharmaceutically acceptable salt thereof, wherein
B is

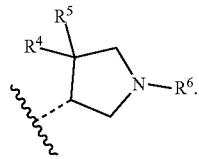

5. The compound of claim 1, or a pharmaceutically acceptable salt thereof, wherein
R³ is selected from the group consisting of F—, Cl—, and F₂HC—.

6. The compound of claim 1, or a pharmaceutically acceptable salt thereof, wherein
R³ is F—.

7. The compound of claim 1, or a pharmaceutically acceptable salt thereof, wherein
R⁶ is C$_{1-3}$-alkylcarbonyl-,
  wherein the C$_{1-3}$-alkylcarbonyl-group is selected from the group consisting of acetyl, ethanecarbonyl, propanecarbonyl, isopropanecarbonyl, and cyclopropanecarbonyl,
  wherein the C$_{1-3}$-alkylcarbonyl-group is optionally substituted with 1, 2 or 3 deuterium.

8. The compound of claim 1 selected from the group consisting of

| Structure |
|---|
| 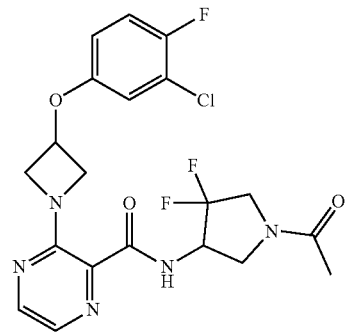 [SMILES: CC(=O)N1CC(NC(=O)c2nccnc2N2CC(Oc3ccc(F)c(Cl)c3)C2)C(F)(F)C1] |
| 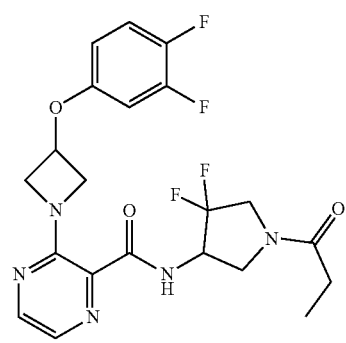 [SMILES: CCC(=O)N1CC(NC(=O)c2nccnc2N2CC(Oc3ccc(F)c(F)c3)C2)C(F)(F)C1] |
| 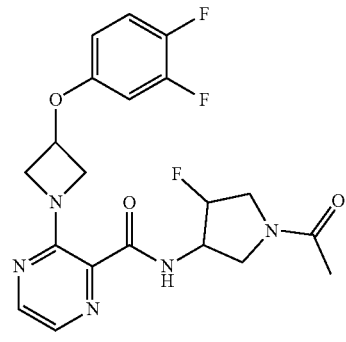 [SMILES: CC(=O)N1CC(F)C(NC(=O)c2nccnc2N2CC(Oc3ccc(F)c(F)c3)C2)C1] |
| 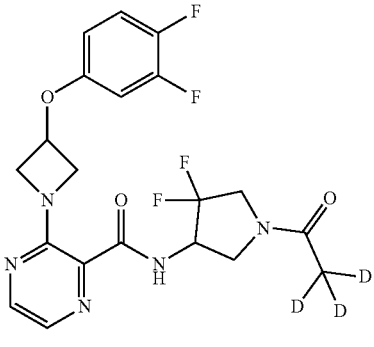 [SMILES: [2H]C([2H])([2H])C(=O)N1CC(NC(=O)c2nccnc2N2CC(Oc3ccc(F)c(F)c3)C2)C(F)(F)C1] |

| 99 -continued | 100 -continued |
|---|---|
| Structure | Structure |
| 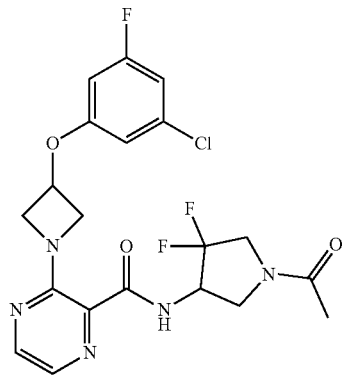 [SMILES: CC(=O)N1CC(NC(=O)c2nccnc2N2CC(Oc3cc(F)cc(Cl)c3)C2)C(F)(F)C1] | 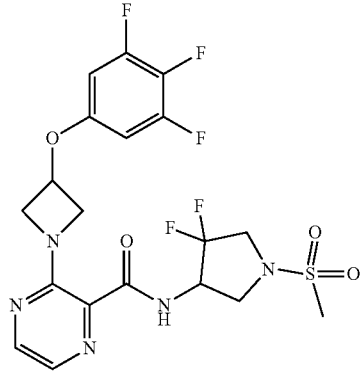 |
| 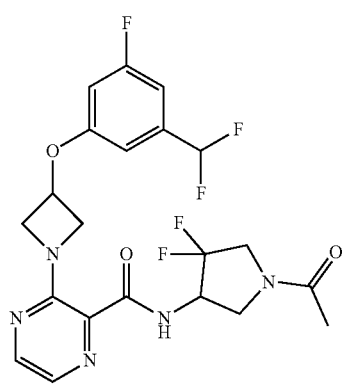 [SMILES: CC(=O)N1CC(NC(=O)c2nccnc2N2CC(Oc3cc(F)cc(C(F)F)c3)C2)C(F)(F)C1] | 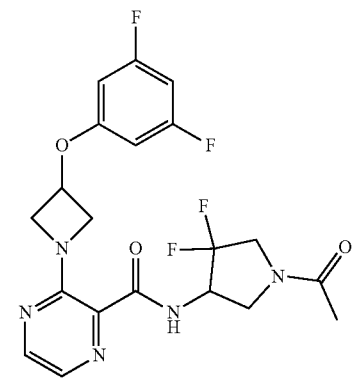 |
| 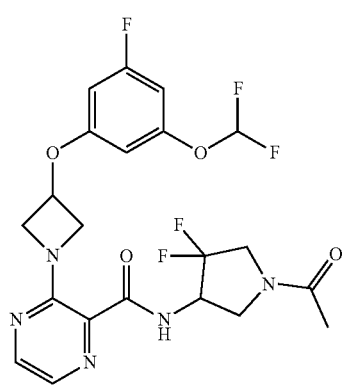 [SMILES: CC(=O)N1CC(NC(=O)c2nccnc2N2CC(Oc3cc(F)cc(OC(F)F)c3)C2)C(F)(F)C1] | 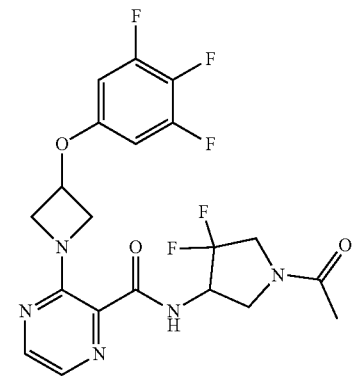 |
| 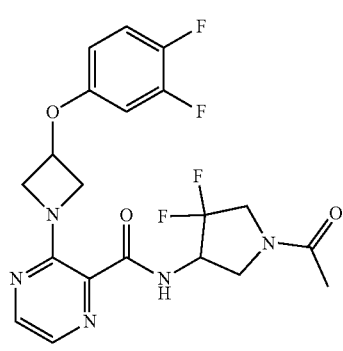 [SMILES: CC(=O)N1CC(NC(=O)c2nccnc2N2CC(Oc3ccc(F)c(F)c3)C2)C(F)(F)C1] | 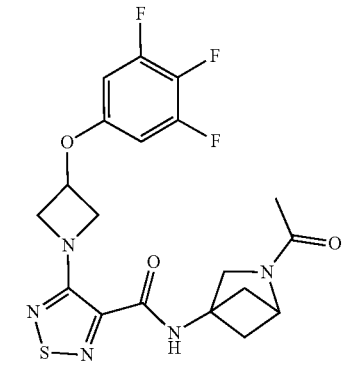 [SMILES: CC(=O)N1CC2(NC(=O)c3nsnc3N3CC(Oc4cc(F)c(F)c(F)c4)C3)CC1C2] |

| 101 -continued | 102 -continued |
|---|---|
| Structure | Structure |
| 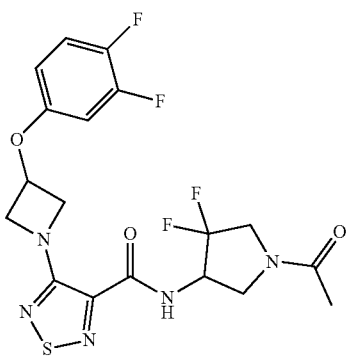 [SMILES: CC(=O)N1CC(NC(=O)c2nsnc2N2CC(Oc3ccc(F)c(F)c3)C2)C(F)(F)C1] | 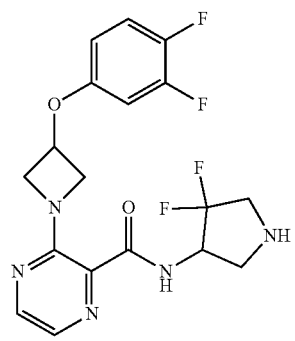 |
| 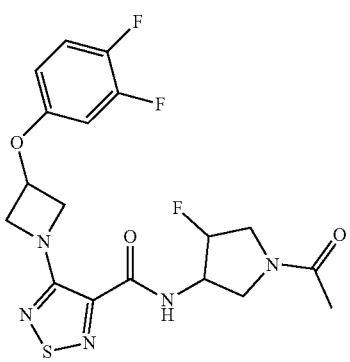 [SMILES: CC(=O)N1CC(F)C(NC(=O)c2nsnc2N2CC(Oc3ccc(F)c(F)c3)C2)C1] | 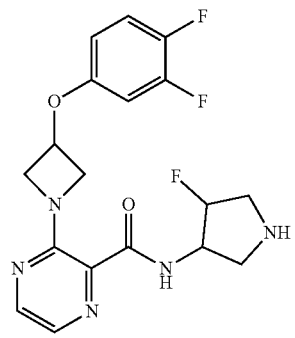 |
| 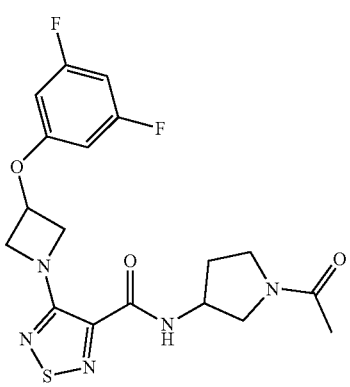 [SMILES: CC(=O)N1CCC(NC(=O)c2nsnc2N2CC(Oc3cc(F)cc(F)c3)C2)C1] | 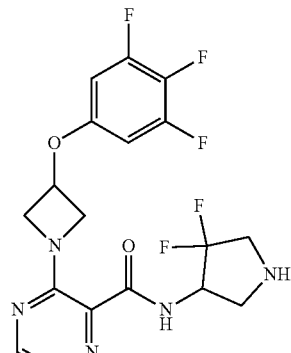 |
| 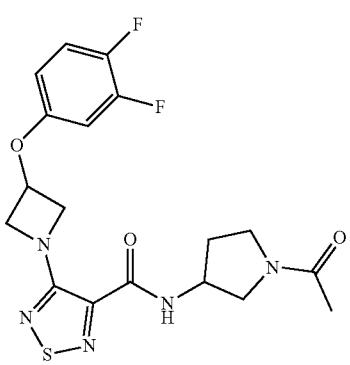 [SMILES: CC(=O)N1CCC(NC(=O)c2nsnc2N2CC(Oc3ccc(F)c(F)c3)C2)C1] | 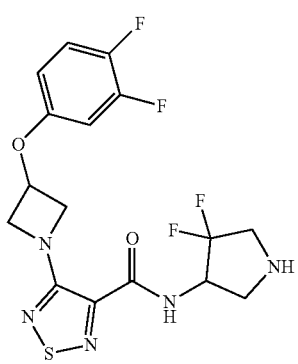 [SMILES: O=C(NC1CNCC1(F)F)c1nsnc1N1CC(Oc2ccc(F)c(F)c2)C1] | or a pharmaceutically acceptable salt thereof.

9. A pharmaceutically acceptable salt of a compound of claim 1.

10. A pharmaceutical composition comprising at least one compound of claim 1, or a pharmaceutically acceptable salt thereof, together with at least one pharmaceutically acceptable adjuvant, diluent and/or carrier.

11. The compound of claim 1, or a pharmaceutically acceptable salt thereof, for use as a medicament.

12. The compound of claim 1, or a pharmaceutically acceptable salt thereof, for use in the prevention and/or treatment of a disorder selected from the group consisting of:
schizophrenia; positive symptoms associated with schizophrenia, schizoaffective disorder, schizophreniform disorder, schizotypal disorder, treatment resistant schizophrenia, attenuated psychosis syndrome and autism-spectrum disorder; augmentation of antipsychotics to treat the positive symptoms associated with schizophrenia, schizoaffective disorder, schizophreniform disorders, schizotypal disorder, treatment resistant schizophrenia, attenuated psychosis syndrome and autism-spectrum disorder; negative symptoms associated with schizophrenia, schizoaffective disorder, schizophreniform disorder, schizotypal disorder, treatment resistant schizophrenia, attenuated psychosis syndrome and autism-spectrum disorder; cognitive impairment associated with schizophrenia (CIAS), schizoaffective disorder, schizophreniform disorder, schizotypal disorder, treatment resistant schizophrenia, attenuated psychosis syndrome and autism-spectrum disorder; treatment resistant schizophrenia; schizoaffective disorder; schizophreniform disorder; schizotypal disorder; drug-induced psychosis; dipolar disorders I and II; attenuated psychosis syndrome; neuropsychiatric symptoms associated with Alzheimer's Disease, Parkinson's Disease, vascular dementia, and frontotemporal dementia; autism spectral disorder (ASD); obsessive-compulsive disorder (OCD); impulse control disorder; gambling disorder; Tourette's syndrome; cognitive deficits associated with Alzheimer's disease, Parkinson's disease, vascular dementia and frontotemporal dementia; depression; attention deficit hyperactivity disorder; major depressive disorder; drug addiction; anxiety; mania in bipolar disorder; acute mania; agitation; detachment; hypothalamic disorders; prolactin-related disorders, hyperprolactinemia; symptoms associated with hypofrontality and hypofrontality associated with drug-abuse; and hyperkinetic symptoms.

13. The compound for use of claim 12, or a pharmaceutically acceptable salt thereof, characterized in that the compound is administered in addition to treatment with at least one antipsychotic drug.

14. A method of preventing and/or treating a disorder selected from the group consisting of:
schizophrenia; positive symptoms associated with schizophrenia, schizoaffective disorder, schizophreniform disorder, schizotypal disorder, treatment resistant schizophrenia, attenuated psychosis syndrome and autism-spectrum disorder; augmentation of antipsychotics to treat the positive symptoms associated with schizophrenia, schizoaffective disorder, schizophreniform disorders, schizotypal disorder, treatment resistant schizophrenia, attenuated psychosis syndrome and autism-spectrum disorder; negative symptoms associated with schizophrenia, schizoaffective disorder, schizophreniform disorder, schizotypal disorder, treatment resistant schizophrenia, attenuated psychosis syndrome and autism-spectrum disorder; cognitive impairment associated with schizophrenia (CIAS), schizoaffective disorder, schizophreniform disorder, schizotypal disorder, treatment resistant schizophrenia, attenuated psychosis syndrome and autism-spectrum disorder; treatment resistant schizophrenia; schizoaffective disorder; schizophreniform disorder; schizotypal disorder; drug-induced psychosis; dipolar disorders I and II; attenuated psychosis syndrome; neuropsychiatric symptoms associated with Alzheimer's Disease, Parkinson's Disease, vascular dementia, and frontotemporal dementia; autism spectral disorder (ASD); obsessive-compulsive disorder (OCD); impulse control disorder; gambling disorder; Tourette's syndrome; cognitive deficits associated with Alzheimer's disease, Parkinson's disease, vascular dementia and frontotemporal dementia; depression; attention deficit hyperactivity disorder; major depressive disorder; drug addiction; anxiety; mania in bipolar disorder; acute mania; agitation; detachment; hypothalamic disorders; prolactin-related disorders, hyperprolactinemia; symptoms associated with hypofrontality and hypofrontality associated with drug-abuse; and hyperkinetic symptoms; comprising administering to a subject in need thereof a therapeutically effective amount of the compound of claim 1, or a pharmaceutically acceptable salt thereof.

15. The method of claim 14, further comprising administering to the subject in need thereof a therapeutically effective amount of at least one antipsychotic drug.

* * * * *